(12) United States Patent
McKinnell et al.

(10) Patent No.: US 9,365,549 B2
(45) Date of Patent: Jun. 14, 2016

(54) HEPATITIS C VIRUS INHIBITORS

(71) Applicant: THERAVANCE BIOPHARMA R&D IP, LLC, South San Francisco, CA (US)

(72) Inventors: Robert Murray McKinnell, Millbrae, CA (US); Daniel D. Long, San Francisco, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 0 days.

(21) Appl. No.: 14/718,296

(22) Filed: May 21, 2015

(65) Prior Publication Data

US 2015/0252023 A1    Sep. 10, 2015

Related U.S. Application Data

(63) Continuation of application No. 13/869,228, filed on Apr. 24, 2013, now Pat. No. 9,066,944.

(60) Provisional application No. 61/773,977, filed on Mar. 7, 2013, provisional application No. 61/637,956, filed on Apr. 25, 2012.

(51) Int. Cl.
| | |
|---|---|
| *C07D 401/14* | (2006.01) |
| *A61K 31/496* | (2006.01) |
| *A61K 45/06* | (2006.01) |
| *C07D 405/14* | (2006.01) |
| *C07F 7/08* | (2006.01) |

(52) U.S. Cl.
CPC ............ *C07D 401/14* (2013.01); *A61K 31/496* (2013.01); *A61K 45/06* (2013.01); *C07D 405/14* (2013.01); *C07F 7/0816* (2013.01)

(58) Field of Classification Search
None
See application file for complete search history.

(56) References Cited

U.S. PATENT DOCUMENTS

| | | |
|---|---|---|
| 7,659,270 B2 | 2/2010 | Bachand et al. |
| 8,088,368 B2 | 1/2012 | Guo et al. |
| 8,147,818 B2 | 4/2012 | Bachand et al. |
| 8,303,944 B2 | 11/2012 | Bachand et al. |
| 8,921,372 B2 | 12/2014 | McKinnell et al. |
| 2008/0050336 A1 | 2/2008 | Bachand et al. |
| 2010/0215618 A1 | 8/2010 | Carter et al. |
| 2011/0064695 A1 | 3/2011 | Qiu et al. |
| 2011/0064698 A1 | 3/2011 | Or et al. |
| 2011/0223134 A1 | 9/2011 | Nair et al. |
| 2011/0224211 A1 | 9/2011 | Schmitz et al. |
| 2011/0286961 A1 | 11/2011 | Belema et al. |
| 2011/0300104 A1 | 12/2011 | Qiu et al. |
| 2012/0040977 A1 | 2/2012 | Li et al. |
| 2013/0115194 A1 | 5/2013 | Long et al. |

FOREIGN PATENT DOCUMENTS

| | | |
|---|---|---|
| WO | 2010/062821 A1 | 6/2010 |
| WO | 2011/091417 A1 | 7/2011 |
| WO | 2012/021704 A1 | 2/2012 |
| WO | 2012018325 | 9/2012 |

OTHER PUBLICATIONS

International Search Report for PCT/US2013/037934 dated Jul. 9, 2013.

*Primary Examiner* — Bong-Sook Baek
(74) *Attorney, Agent, or Firm* — Vasily A. Ignatenko; Fish & Richardson P.C.

(57) ABSTRACT

The invention provides compounds of formulas (I) or (II):

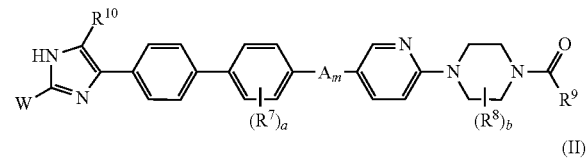

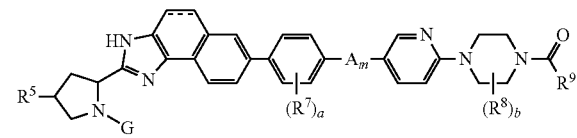

wherein the variables are defined in the specification, or a pharmaceutically-acceptable salt thereof, that are inhibitors of replication of the hepatitis C virus. The invention also provides pharmaceutical compositions comprising such compounds, methods of using such compounds to treat hepatitis C viral infections, and processes and intermediates useful for preparing such compounds.

15 Claims, No Drawings

HEPATITIS C VIRUS INHIBITORS

BACKGROUND OF THE INVENTION

1. Field of the Invention

The invention is directed to compounds useful as inhibitors of replication of the hepatitis C virus (HCV). The invention is also directed to pharmaceutical compositions comprising such compounds, methods of using such compounds to treat HCV infection, and processes and intermediates useful for preparing such compounds.

2. State of the Art

Recent estimates place the number of people infected with the hepatitis C virus (HCV) worldwide at more than 170 million, including 3 million people in the United States. The infection rate is thought to be roughly 4 to 5 times that of the human immunodeficiency virus (HIV). While in some individuals, the natural immune response is able to overcome the virus, in the majority of cases, a chronic infection is established, leading to increased risk of developing cirrhosis of the liver and hepatocellular carcinomas. Infection with hepatitis C, therefore, presents a serious public health problem.

Prior to mid-2011, the accepted standard of care for HCV involved the use of a pegylated interferon which is believed to act by boosting the body's immune response, together with ribavirin. Unfortunately, the course of treatment is lengthy, typically 48 weeks, often accompanied by serious adverse side effects, including depression, flu-like symptoms, fatigue, and hemolytic anemia, and ineffective in up to 50% of patients. In mid-2011, two HCV protease inhibitors were approved in the United States to be used in combination with interferon and ribavirin. Although better cure rates have been reported, the course of therapy is still lengthy and accompanied by undesirable side effects. Accordingly, there remains a serious unmet need in HCV treatment.

The virus responsible for HCV infection has been identified as a positive-strand RNA virus belonging to the family Flaviviridae. The HCV genome encodes a polyprotein that during the viral lifecycle is cleaved into ten individual proteins, including both structural and non-structural proteins. The six non-structural proteins, denoted as NS2, NS3, NS4A, NS4B, NS5A, and NS5B have been shown to be required for RNA replication. In particular, the NS5A protein appears to play a significant role in viral replication, as well as in modulation of the physiology of the host cell. Effects of NS5A on interferon signaling, regulation of cell growth and apoptosis have also been identified. (Macdonald et al., *Journal of General Virology* (2004), 85, 2485-2502.) Compounds which inhibit the function of the NS5A protein are expected to provide a new approach to HCV therapy.

SUMMARY OF THE INVENTION

In one aspect, the invention provides novel compounds which inhibit replication of the HCV virus.

Accordingly, the invention provides a compound of formula (I):

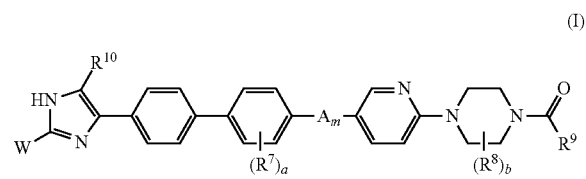

or of formula (II):

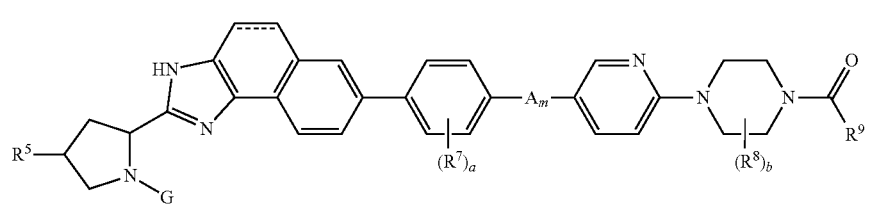

wherein the dashed bond in formula (II) may be present or absent;

W is selected from

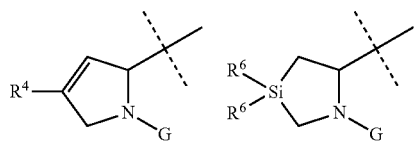

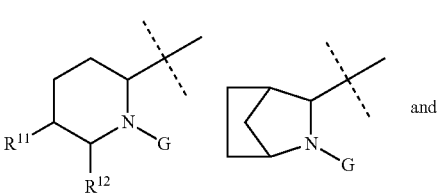 and

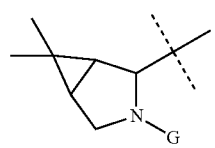

G is

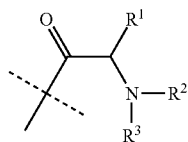

R¹ is selected from $C_{1-6}$alkyl, $C_{1-6}$alkoxy, phenyl, $C_{3-6}$cycloalkyl, heterocycle, and heteroaryl, wherein $C_{1-6}$alkyl is optionally substituted with —OR$^a$, amino, —SR$^e$, heterocycle, or heteroaryl, $C_{1-6}$alkoxy is optionally substituted with —OR$^a$, and heterocycle is optionally substituted with —OR$^a$, amino, or —C(O)OC$_{1-6}$alkyl, or with one or two $C_{1-3}$alkyl;

R² is selected from hydrogen and $C_{1-6}$alkyl;

R³ is selected from hydrogen, $C_{1-6}$alkyl, —C(O)OC$_{1-6}$alkyl, —C(O)NR$^b$R$^c$, —C(O)C$_{3-6}$cycloalkyl, and —S(O)$_2$C$_{1-3}$alkyl;

R⁴ is selected from $C_{1-6}$alkyl, $C_{3-6}$cycloalkyl, and halo;

R⁵ is selected from hydrogen, $C_{1-6}$alkyl, —OR$^d$, halo, —S(O)C$_{1-3}$alkyl, —S(O)$_2$C$_{1-3}$alkyl, NR$^b$R$^c$, —CN, and —C(O)NR$^b$R$^c$;

R⁶ is independently selected from hydrogen, $C_{1-6}$alkyl, and halo;

R⁷ is selected from halo, $C_{1-3}$alkyl, and $C_{1-3}$alkoxy wherein $C_{1-3}$alkyl and $C_{1-3}$alkoxy are optionally substituted with one, two, three, four, or five halo;

R⁸ is $C_{1-3}$alkyl, optionally substituted with —OR$^d$;

R⁹ is selected from $C_{1-6}$alkyl, $C_{3-6}$cycloalkyl, $C_{1-6}$alkoxy, —NR$^f$R$^g$, heteroaryl, heterocycle, and —CH$_2$-heteroaryl;

wherein:
$C_{1-6}$alkyl is optionally substituted with one or two substituents independently selected from —OR$^h$, —NR$^j$R$^k$, —NHC(O)C$_{1-3}$alkyl, —NHC(O)C$_{3-6}$cycloalkyl, and —NHC(O)OC$_{1-3}$alkyl;

$C_{1-6}$alkoxy is optionally substituted with —OR$^h$;

any $C_{3-6}$cycloalkyl is optionally substituted with one, two, or three substituents independently selected from $C_{1-3}$alkyl, halo, —OR$^h$, and —CD$_3$;

any heterocycle is optionally substituted with one, two, or three substituents independently selected from $C_{1-3}$alkyl, halo, —C(O)OC$_{1-3}$alkyl, —C(O)C$_{1-6}$alkyl, —C(O)C$_{3-6}$cycloalkyl, —C(O)NHC$_{1-6}$alkyl, and —C(O)NHC$_{3-6}$cycloalkyl;
wherein any —C(O)C$_{1-6}$alkyl is optionally substituted with —NHC(O)OC$_{1-3}$alkyl, —OR$^h$ or —NR$^j$R$^k$, any heteroaryl is optionally substituted with one or two $C_{1-3}$alkyl;

R$^a$, R$^b$, R$^c$, R$^d$, R$^e$, R$^f$, R$^h$, R$^j$, and R$^k$ are each independently hydrogen or $C_{1-3}$alkyl;

R$^g$ is selected from hydrogen, $C_{1-6}$alkyl, and $C_{3-6}$cycloalkyl;

R¹⁰ is hydrogen, halo, or $C_{1-3}$alkyl substituted with one, two, or three halo or with —OR$^d$;

R¹¹ is selected from hydrogen, $C_{1-6}$alkyl, and halo;

R¹² is hydrogen, or R¹¹ and R¹² taken together form —CH$_2$—;

A$_m$ is —NHC(O)— or —C(O)NH— a is 0, 1, or 2; and b is 0, 1 or 2;

or a pharmaceutically-acceptable salt or stereoisomer thereof.

As used hereinafter, the phrase "compound of formula (I)" means a compound of formula (I) or a pharmaceutically acceptable salt thereof; i.e., this phrase means a compound of formula (I) in free base form or in a pharmaceutically acceptable salt form unless otherwise indicated and similarly, for "compound of formula (II)".

The invention also provides a pharmaceutical composition comprising a compound of the invention and a pharmaceutically-acceptable carrier. In addition, the invention provides a pharmaceutical composition comprising a compound of the invention, a pharmaceutically-acceptable carrier and one or more other therapeutic agents useful for treating hepatitis C viral infections.

The invention also provides a method of treating a hepatitis C viral infection in a mammal, the method comprising administering to the mammal a therapeutically effective amount of a compound or of a pharmaceutical composition of the invention. In addition, the invention provides a method of treating a hepatitis C viral infection in a mammal, the method comprising administering to the mammal a compound or a pharmaceutical composition of the invention and one or more other therapeutic agents useful for treating hepatitis C viral infections. Further, the invention provides a method of inhibiting replication of the hepatitis C virus in a mammal, the method comprising administering a compound or a pharmaceutical composition of the invention.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a hepatitis C viral infection in a mammal.

DETAILED DESCRIPTION OF THE INVENTION

Among other aspects, the invention provides inhibitors of HCV replication of formula (I), pharmaceutically-acceptable salts thereof, and intermediates for the preparation thereof. The following substituents and values are intended to provide representative examples of various aspects of this invention. These representative values are intended to further define such aspects and are not intended to exclude other values or limit the scope of the invention.

In a specific aspect, R¹ is selected from $C_{1-6}$alkyl, $C_{1-6}$alkoxy, phenyl, $C_{3-6}$cycloalkyl, heterocycle, and heteroaryl, wherein $C_{1-6}$alkyl is optionally substituted with —OR$^a$, amino, —SR$^e$, heterocycle, or heteroaryl, $C_{1-6}$alkoxy is optionally substituted with —OR$^a$, and heterocycle is optionally substituted with —OR$^a$, amino, or —C(O)OC$_{1-6}$alkyl, or with one or two $C_{1-3}$alkyl.

In another specific aspect, R¹ is selected from $C_{1-6}$alkyl, phenyl, and heterocycle, wherein $C_{1-6}$alkyl is optionally substituted with —OR$^a$, and heterocycle has six ring atoms and is optionally substituted with —OR$^a$ or amino or with one or two methyl.

In another specific aspect, R¹ is selected from $C_{1-6}$alkyl, phenyl, and tetrahydropyranyl, wherein $C_{1-6}$alkyl is optionally substituted with —OR$^a$; wherein R$^a$ is hydrogen or $C_{1-3}$alkyl.

In a specific aspect, R¹ is $C_{1-3}$ alkyl.

In another specific aspect, R¹ is isopropyl.

In yet another specific aspect, R¹ is phenyl.

In still another specific aspect, R¹ is tetrahydropyranyl.

In still another specific aspect, R¹ is tetrahydropyran-4-yl.

In a specific aspect, R² is hydrogen or $C_{1-6}$alkyl.

In other specific aspects, R² is hydrogen or $C_{1-3}$alkyl; or R² is hydrogen.

In a specific aspect, $R^3$ is selected from hydrogen, $C_{1-6}$alkyl, —C(O)OC$_{1-6}$alkyl, —C(O)NR$^b$R$^c$, —C(O)C$_{3-6}$cycloalkyl, and —S(O)$_2$C$_{1-3}$alkyl; or $R^2$ and $R^3$ together with the nitrogen atom to which they are attached form a heterocycle;

In another specific aspect, $R^3$ is selected from hydrogen, $C_{1-6}$alkyl, —C(O)OC$_{1-6}$alkyl, —C(O)NR$^b$R$^c$, —C(O)C$_{3-6}$cycloalkyl, and —S(O)$_2$C$_{1-3}$alkyl;

In another specific aspect, $R^3$ is selected from hydrogen, $C_{1-6}$alkyl, and —C(O)OC$_{1-6}$alkyl.

In yet another specific aspect, $R^3$ is —C(O)OC$_{1-3}$alkyl.

In a specific aspect, $R^1$ is $C_{1-6}$alkyl, $R^2$ is hydrogen, and $R^3$ is —C(O)OC$_{1-6}$alkyl.

In another specific aspect, $R^1$ is isopropyl, $R^2$ is hydrogen, and $R^3$ is —C(O)OCH$_3$.

In yet other specific aspects, $R^1$ is phenyl and $R^2$ and $R^3$ are each $C_{1-3}$alkyl; or $R^1$ is phenyl, $R^2$ is hydrogen, and $R^3$ is —C(O)OC$_{1-3}$alkyl; or $R^1$ is tetrahydropyranyl, $R^2$ is hydrogen, and $R^3$ is —C(O)OC$_{1-3}$alkyl.

In a specific aspect, $R^4$ is selected from $C_{1-6}$alkyl, $C_{3-6}$cycloalkyl, and halo;

In another specific aspect, $R^4$ is $C_{1-6}$alkyl or $C_{3-6}$cycloalkyl;

In another specific aspect, $R^4$ is $C_{1-6}$alkyl.

In another specific aspect, $R^4$ is $C_{3-6}$cycloalkyl.

In another specific aspect, $R^4$ is methyl or cyclopropyl.

In a specific aspect, $R^5$ is selected from hydrogen, $C_{1-6}$alkyl, —OR$^d$, halo, —S(O)C$_{1-3}$alkyl, —S(O)$_2$C$_{1-3}$alkyl, NR$^b$R$^c$, —CN, and —C(O)NR$^b$R$^c$.

In another specific aspect, $R^5$ is selected from hydrogen, $C_{1-6}$alkyl, and —OR$^d$;

In a specific aspect, $R^5$ is hydrogen or $C_{1-3}$alkyl.

In another specific aspect, $R^5$ is methyl.

In a specific aspect, $R^6$ is independently selected from hydrogen, $C_{1-6}$alkyl, and halo.

In another specific aspect, $R^6$ is hydrogen or $C_{1-3}$alkyl.

In another specific aspect, $R^6$ is methyl.

In a specific aspect, $R^7$ is selected from halo, $C_{1-3}$alkyl, and $C_{1-3}$alkoxy wherein $C_{1-6}$alkyl and $C_{1-6}$alkoxy are optionally substituted with one, two, three, four, or five halo.

In another specific aspect $R^7$ is selected from halo, $C_{1-3}$alkyl, and $C_{1-3}$alkoxy wherein $C_{1-6}$alkyl and $C_{1-6}$alkoxy are substituted with one, two, or three halo.

In yet another specific aspect, $R^7$ is selected from fluoro, chloro, —CF$_3$, and —OCF$_3$.

In a specific aspect, $R^9$ is defined as in formulas (I) and (II).

In another specific aspect, $R^9$ is selected from $C_{1-6}$alkyl, $C_{3-6}$cycloalkyl, $C_{1-6}$alkoxy, —NR$^f$R$^g$, heteroaryl, and heterocycle; wherein any heteroaryl or heterocycle has 5 or 6 ring atoms; $C_{1-6}$alkyl is optionally substituted with one or two substituents independently selected from —OR$^h$, —NR$^j$R$^k$, —NHC(O)C$_{1-3}$alkyl, and —NHC(O)OC$_{1-3}$alkyl; any $C_{3-6}$cycloalkyl is optionally substituted with one or two substituents independently selected from $C_{1-3}$alkyl and halo; any heterocycle is optionally substituted with one, two, or three substituents independently selected from $C_{1-3}$alkyl, halo, —C(O)OC$_{1-3}$alkyl, —C(O)C$_{1-6}$alkyl, wherein any —C(O)C$_{1-6}$alkyl is optionally substituted with —NHC(O)OC$_{1-3}$alkyl or —OR$^h$.

In yet another aspect, $R^9$ is selected from $C_{1-6}$alkyl, optionally substituted with —OR$^h$ wherein R$^h$ is hydrogen or $C_{1-3}$alkyl, and $C_{3-4}$cycloalkyl, optionally substituted with one or two $C_{1-3}$alkyl.

In a still further aspect, $R^9$ is selected from cyclopropyl, 2,2-dimethylcyclopropyl, tert-butyl, and 3-hydroxy-2,2-dimethylpropyl.

In a specific aspect, $R^{10}$ is hydrogen, halo, or $C_{1-3}$alkyl, wherein $C_{1-3}$alkyl is optionally substituted with one, two, or three halo, or with —OR$^d$.

In a specific aspect, $R^{10}$ is hydrogen, halo, or $C_{1-3}$alkyl substituted with one, two, or three halo.

In other specific aspects, $R^{10}$ is hydrogen or halo; or $R^{10}$ is hydrogen, chloro, or fluoro.

In another specific aspect, $R^{10}$ is chloro.

In yet another specific aspect, $R^{10}$ is hydrogen.

In a specific aspect, $R^{11}$ is selected from hydrogen, $C_{1-6}$alkyl, and halo.

In another specific aspect, $R^{11}$ is hydrogen or $C_{1-6}$alkyl.

In yet another specific aspect, $R^{11}$ is methyl.

In a specific aspect $R^{12}$ is hydrogen.

In another specific aspect, $R^{11}$ and $R^{12}$ taken together form —CH$_2$—.

In a specific aspect, a is 0, 1, or 2.

In another specific aspect, a is 1 or 2.

In a specific aspect, b is 0, 1, or 2.

In other specific aspects, b is 1 or 2; or b is 1.

In one aspect, the invention provides compounds of formula (Ia):

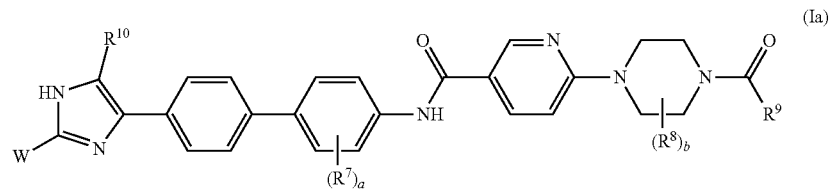

(Ia)

In a specific aspect, $R^8$ is $C_{1-3}$alkyl, optionally substituted with —OR$^d$; wherein R$^d$ is hydrogen or $C_{1-3}$alkyl.

In a specific aspect, $R^8$ is $C_{1-3}$alkyl.

In another specific aspect, $R^8$ is methyl.

wherein the variables of formula (Ia) are as defined herein.

In another aspect, the invention provides compounds of formula (Ib):

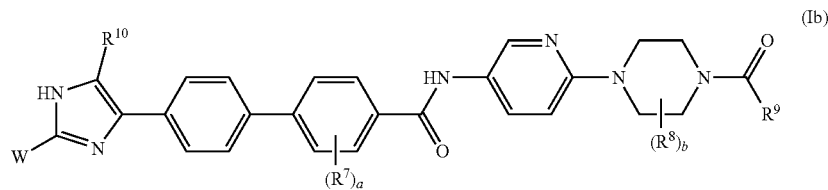

wherein the variables of formula (Ib) are as defined herein.

In yet another aspect, the invention provides compounds of formula (III):

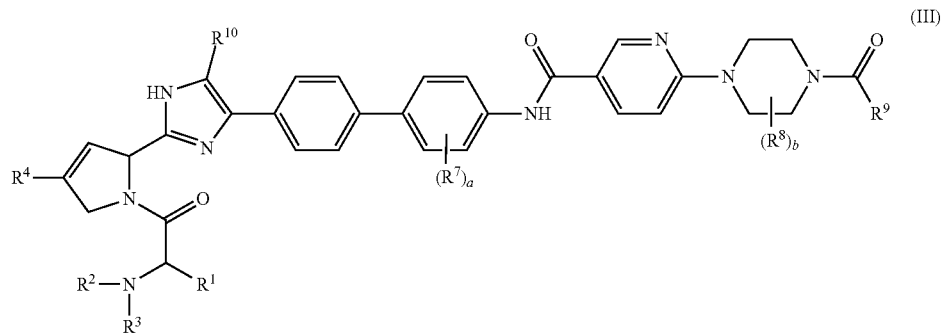

wherein the variables of formula (III) are as defined herein.

In another aspect, the invention provides compounds of formula (IV):

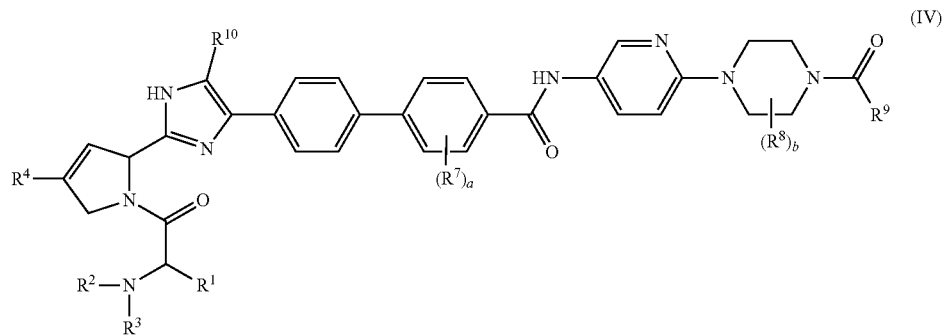

wherein the variables of formula (IV) are as defined herein.

In yet another aspect, the invention provides compounds of formula (V):

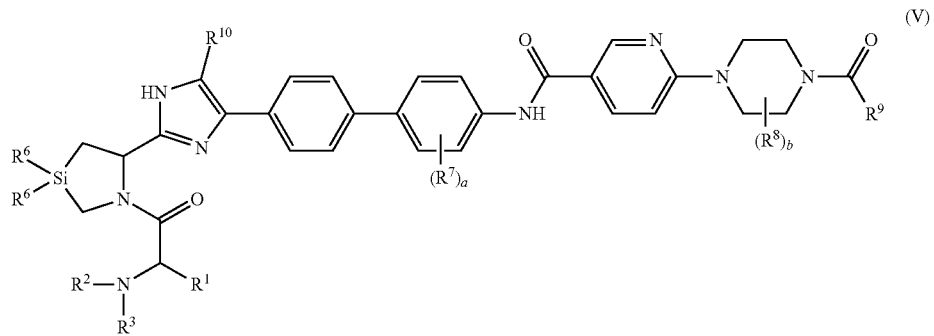

wherein the variables of formula (V) are as defined herein.

In another aspect, the invention provides compounds of formula (VI):

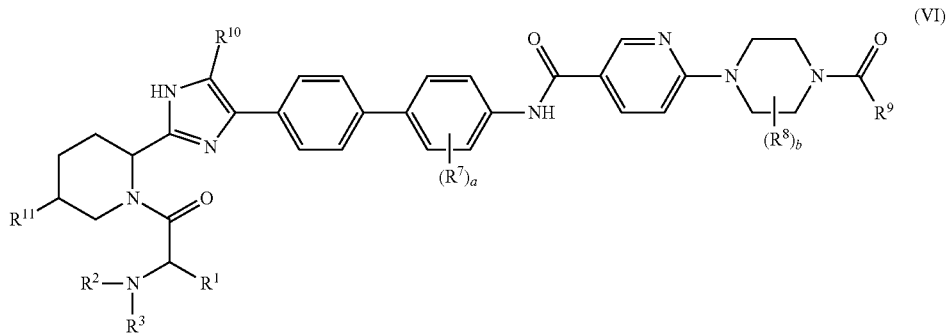

wherein the variables of formula (VI) are as defined herein.

In another aspect, the invention provides compounds of formula (VII):

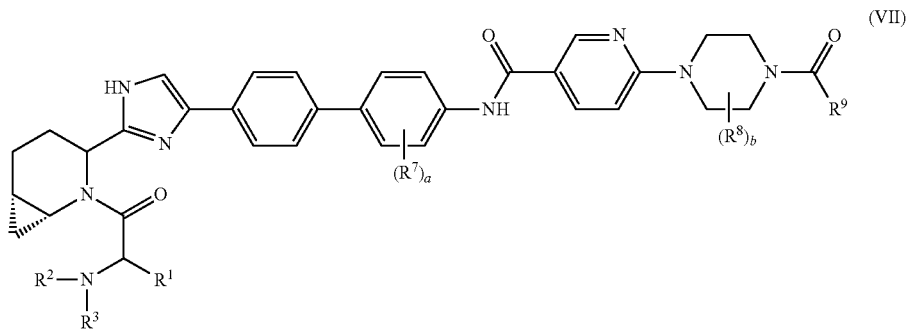

wherein the variables of formula (VII) are as defined herein.

In a further aspect, the invention provides compounds of formula (VIII):

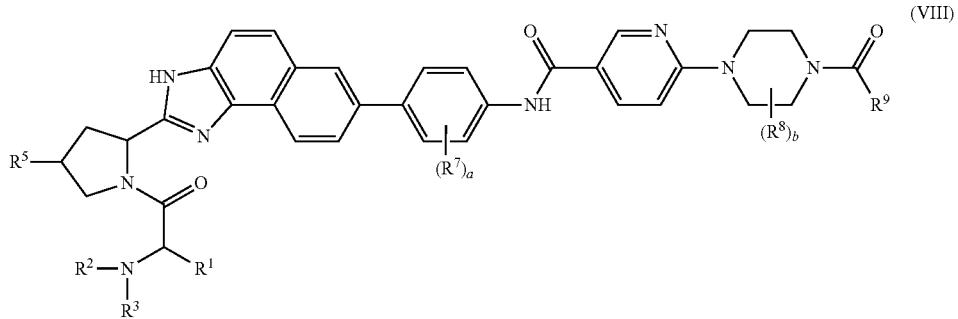

wherein the variables of formula (VIII) are as defined herein.

In a still further aspect, the invention provides compounds of formula (IX):

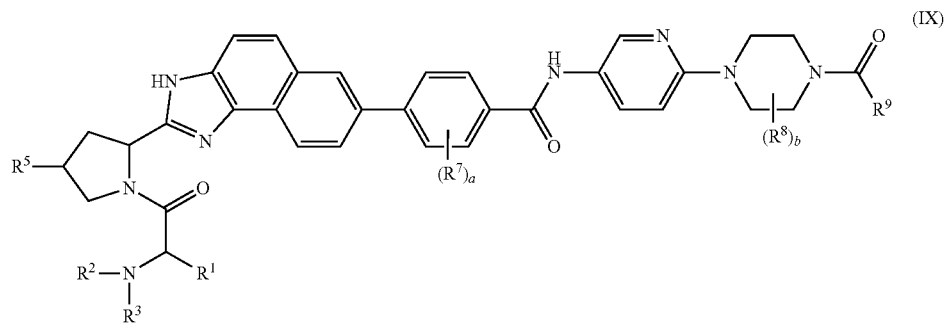

wherein the variables of formula (IX) are as defined herein.

In yet another aspect, the invention provides compounds of formula (X):

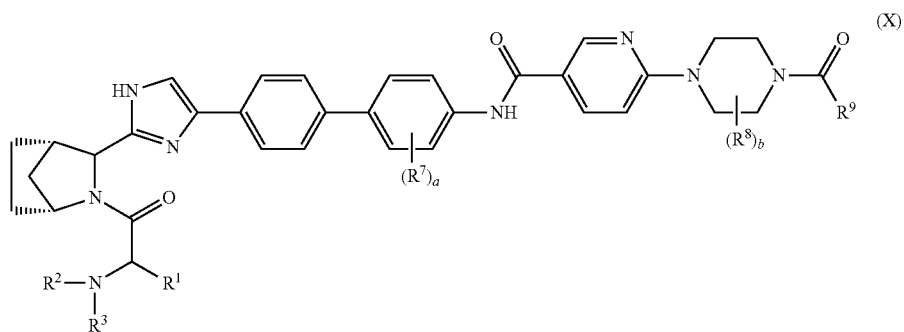

wherein the variables of formula (X) are as defined herein.

In still another aspect, the invention provides compounds of formula (XI):

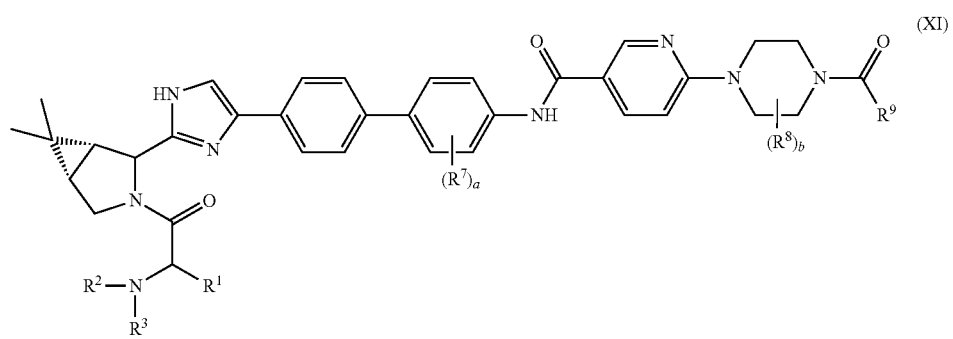

wherein the variables of formula (XI) are as defined herein.

In one aspect, the invention provides the compounds of Examples 1-15 and Tables 1-5 below The chemical naming convention used herein is illustrated for the compound of Example 1:

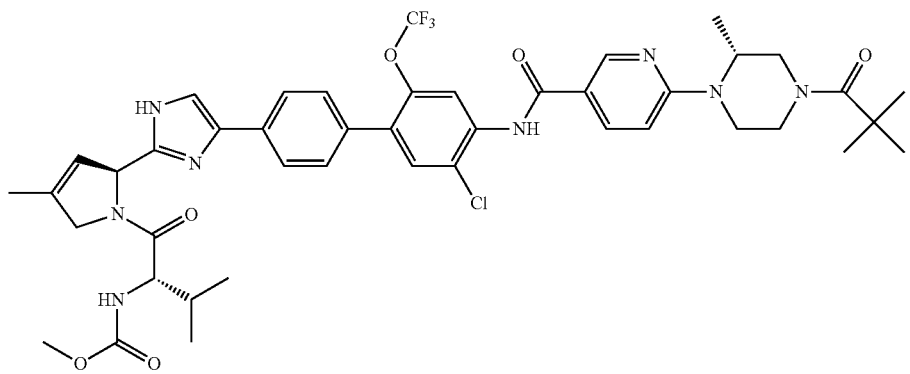 [SMILES: COC(=O)N[C@H](C(=O)N1CC(C)=C[C@H]1c1nc(-c2ccc(-c3cc(Cl)c(NC(=O)c4ccc(N5CCN(C(=O)C(C)(C)C)C[C@H]5C)nc4)cc3OC(F)(F)F)cc2)c[nH]1)C(C)C]

which is [(S)-1-((S)-2-{4-[5'-chloro-4'-({6-[(R)-4-(2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-4-methyl-2,5-dihydro-pyrrole-1-carbonyl)-2-methyl-propyl]-carbamic acid methyl ester according to the IUPAC conventions as implemented in AutoNom software, (MDL Information Systems, GmbH, Frankfurt, Germany).

The imidazole moiety in the structure of formula (I) exists in tautomeric forms, illustrated below for a fragment of the compound of Example 1

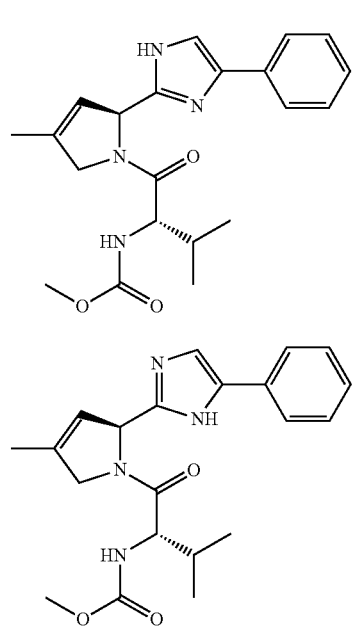

According to the IUPAC convention, these representations give rise to different numbering of the atoms of the imidazole moiety: {(S)-2-methyl-1-[(S)-4-methyl-2-(4-phenyl-1H-imidazol-2-yl)-2,5-dihydro-pyrrole-1-carbonyl]-propyl}-carbamic acid methyl ester (structure A) vs. {(S)-2-methyl-1-[(S)-4-methyl-2-(5-phenyl-1H-imidazol-2-yl)-2,5-dihydro-pyrrole-1-carbonyl]-propyl}-carbamic acid methyl ester (structure B).

Similarly, the napthimidazole structure of formula (II), illustrated for a fragment of the compound of Example 8, exists in tautomeric forms:

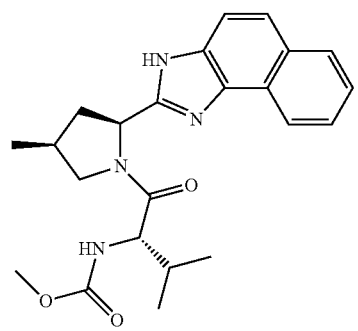

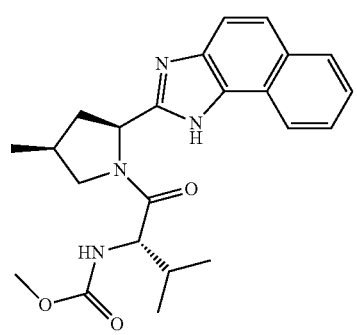

which also give rise to different numbering: {(S)-2-methyl-1-[(2S,4S)-4-methyl-2-(3H-naphtho[1,2-d]imidazol-2-yl)-pyrrolidine-1-carbonyl]-propyl}-carbamic acid methyl ester (structure C) vs. {(S)-2-methyl-1-[(2S,4S)-4-methyl-2-(1H-naphtho[1,2-d]imidazol-2-yl)-pyrrolidine-1-carbonyl]-propyl}-carbamic acid methyl ester (structure D). It will be understood that although structures are shown, or named, in a particular form, the invention also includes the tautomer thereof.

The compounds of the invention contain one or more chiral centers and therefore, such compounds (and intermediates thereof) can exist as racemic mixtures; pure stereoisomers (i.e., enantiomers or diastereomers); stereoisomer-enriched mixtures and the like. Chiral compounds shown or named herein without a defined stereochemistry at a chiral center are intended to include any or all possible stereoisomer variations at the undefined stereocenter unless otherwise indicated. The depiction or naming of a particular stereoisomer means the indicated stereocenter has the designated stereochemistry with the understanding that minor amounts of other stereoisomers may also be present unless otherwise indicated, provided that the utility of the depicted or named compound is not eliminated by the presence of another stereoisomer.

Compounds of formula (I) also contain several basic groups (e.g., amino groups) and therefore, such compounds can exist as the free base or in various salt forms, such a mono-protonated salt form, a di-protonated salt form, a tri-protonated salt form, or mixtures thereof. All such forms are included within the scope of this invention, unless otherwise indicated.

This invention also includes isotopically-labeled compounds of formula (I), i.e., compounds of formula (I) where an atom has been replaced or enriched with an atom having the same atomic number but an atomic mass different from the atomic mass that predominates in nature. Examples of isotopes that may be incorporated into a compound of formula (I) include, but are not limited to, $^2H$, $^3H$, $^{11}C$, $^{13}C$, $^{14}C$, $^{13}N$, $^{15}N$, $^{15}O$, $^{17}O$, $^{18}O$, $^{35}S$, $^{36}Cl$, and $^{18}F$. Of particular interest are compounds of formula (I) enriched in tritium or carbon-14, which compounds can be used, for example, in tissue distribution studies. Also of particular interest are compounds of formula (I) enriched in deuterium especially at a site of metabolism, which compounds are expected to have greater metabolic stability. Additionally of particular interest are compounds of formula (I) enriched in a positron emitting isotope, such as $^{11}C$, $^{18}F$, $^{15}O$ and $^{13}N$, which compounds can be used, for example, in Positron Emission Tomography (PET) studies.

DEFINITIONS

When describing this invention including its various aspects and embodiments, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl (Me), ethyl (Et), n-propyl (n-Pr) or (nPr), isopropyl (i-Pr) or (iPr), n-butyl (n-Bu) or (nBu), sec-butyl, isobutyl, tert-butyl (t-Bu) or (tBu), n-pentyl, n-hexyl, 2,2-dimethylpropyl, 2-methylbutyl, 3-methylbutyl, 2-ethylbutyl, 2,2-dimethylpentyl, 2-propylpentyl, and the like When a specific number of carbon atoms are intended for a particular term, the number of carbon atoms is shown preceding the term. For example, the term "$C_{1-3}$ alkyl" means an alkyl group having from 1 to 3 carbon atoms wherein the carbon atoms are in any chemically-acceptable configuration, including linear or branched configurations.

The term "alkoxy" means the monovalent group —O-alkyl, where alkyl is defined as above. Representative alkoxy groups include, by way of example, methoxy, ethoxy, propoxy, butoxy, and the like.

The term "cycloalkyl" means a monovalent saturated carbocyclic group which may be monocyclic or multicyclic. Unless otherwise defined, such cycloalkyl groups typically contain from 3 to 10 carbon atoms. Representative cycloalkyl groups include, by way of example, cyclopropyl (cPr), cyclobutyl, cyclopentyl, cyclohexyl, cycloheptyl, cyclooctyl, adamantyl, and the like.

The term "heterocycle", "heterocyclic", or "heterocyclic ring" means a monovalent saturated or partially unsaturated cyclic non-aromatic group, having from 3 to 10 total ring atoms, wherein the ring contains from 2 to 9 carbon ring atoms and from 1 to 4 ring heteroatoms selected from nitrogen, oxygen, and sulfur. Heterocyclic groups may be monocyclic or multicyclic (i.e., fused or bridged). Representative heterocyclic groups include, by way of example, pyrrolidinyl, piperidinyl, piperazinyl, imidazolidinyl, morpholinyl, thiomorpholyl, indolin-3-yl, 2-imidazolinyl, tetrahydropyranyl, 1,2,3,4-tetrahydroisoquinolin-2-yl, quinuclidinyl, 7-azanorbornanyl, nortropanyl, and the like, where the point of attachment is at any available carbon or nitrogen ring atom. Where the context makes the point of attachment of the heterocyclic group evident, such groups may alternatively be referred to as a non-valent species, i.e. pyrrolidine, piperidine, piperazine, imidazole, tetrahydropyran etc.

The term "heteroaryl" or "heteroaryl ring" means a monovalent aromatic group having from 5 to 10 total ring atoms, wherein the ring contains from 1 to 9 carbon ring atoms and from 1 to 4 ring heteroatoms selected from nitrogen, oxygen, and sulfur. Heteroaryl groups may be monocyclic or multicyclic. Representative heteroaryl groups include, by way of example, pyrroyl, isoxazolyl, isothiazolyl, pyrazolyl, oxazolyl, oxadiazolyl, thiadiazolyl, thiazolyl, imidazolyl, triazolyl, tetrazolyl, furanyl, triazinyl, thienyl, pyridyl (or, equivalently, pyridinyl), pyrimidyl, pyridazinyl, pyrazinyl, indolyl, benzofuranyl, benzothienyl, benzimidazolyl, benzthiazolyl, and the like, where the point of attachment is at any available carbon or nitrogen ring atom. Where the context makes the point of attachment of the heteroaryl group evident, such groups may alternatively be referred to as a non-valent species, i.e. pyrrole, isoxazole, isothiazole, pyrazole, imidazole, etc.

The term "halo" means fluoro, chloro, bromo or iodo.

The term "therapeutically effective amount" means an amount sufficient to effect treatment when administered to a patient in need of treatment.

The term "treatment" as used herein means the treatment of a disease, disorder, or medical condition in a patient (such as hepatitis C viral infection), such as a mammal (particularly a human) which includes one or more of the following:

(a) preventing the disease, disorder, or medical condition from occurring, i.e., preventing the reoccurrence of the disease or medical condition or prophylactic treatment of a patient that is pre-disposed to the disease or medical condition;

(b) ameliorating the disease, disorder, or medical condition, i.e., eliminating or causing regression of the disease, disorder, or medical condition in a patient, including counteracting the effects of other therapeutic agents;

(c) suppressing the disease, disorder, or medical condition, i.e., slowing or arresting the development of the disease, disorder, or medical condition in a patient; or (d) alleviating the symptoms of the disease, disorder, or medical condition in a patient.

The term "pharmaceutically acceptable salt" means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "salt thereof" means a compound formed when the hydrogen of an acid is replaced by a cation, such as a metal cation or an organic cation and the like. For example, the cation can be a protonated form of a compound of formula (I), i.e. a form where one or more amino groups have been protonated by an acid. Typically, the salt is a pharmaceutically acceptable salt, although this is not required for salts of intermediate compounds that are not intended for administration to a patient.

The term "amino-protecting group" means a protecting group suitable for preventing undesired reactions at an amino nitrogen. Representative amino-protecting groups include, but are not limited to, formyl; acyl groups, for example alkanoyl groups, such as acetyl and tri-fluoroacetyl; alkoxycarbonyl groups, such as tert butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS), tert-butyldimethylsilyl (TBDMS), [2-(trimethylsilyl)ethoxy]methyl (SEM); and the like. Numerous protecting groups, and their introduction and removal, are described in T. W. Greene and G. M. Wuts, *Protecting Groups in Organic Synthesis*, Third Edition, Wiley, New York General Synthetic Procedures Compounds of this invention, and intermediates thereof, can be prepared according to the following general methods and procedures using commercially-available or routinely-prepared starting materials and reagents. The substituents and variables (e.g., $R^1$, $R^2$, $R^3$, $R^4$, etc.) used in the following schemes have the same meanings as those defined elsewhere herein unless otherwise indicated. Additionally, compounds having an acidic or basic atom or functional group may be used or may be produced as a salt unless otherwise indicated (in some cases, the use of a salt in a particular reaction will require conversion of the salt to a non-salt form, e.g., a free base, using routine procedures before conducting the reaction).

Although a particular embodiment of the present invention may be shown or described in the following procedures, those skilled in the art will recognize that other embodiments or aspects of the present invention can also be prepared using such procedures or by using other methods, reagents, and starting materials know to those skilled in the art. In particular, it will be appreciated that compounds of the invention may be prepared by a variety of process routes in which reactants are combined in different orders to provide different intermediates en route to producing final products.

In one exemplary method of synthesis, compounds of formula (1-7) in which $A_m$ is defined as —NHC(O)— are prepared by a Suzuki coupling reaction in the presence of a palladium catalyst (Miyaura and Suzuki, *Chem. Rev.* 1995, 95, 2457-2483). As shown in Scheme 1A below, either coupling partner may bear the boronate moiety. Alternatively, a boronic acid reagent may be used in place of the boronate reagent, such as the pinacol boronate depicted in Scheme 1A.

Scheme 1A

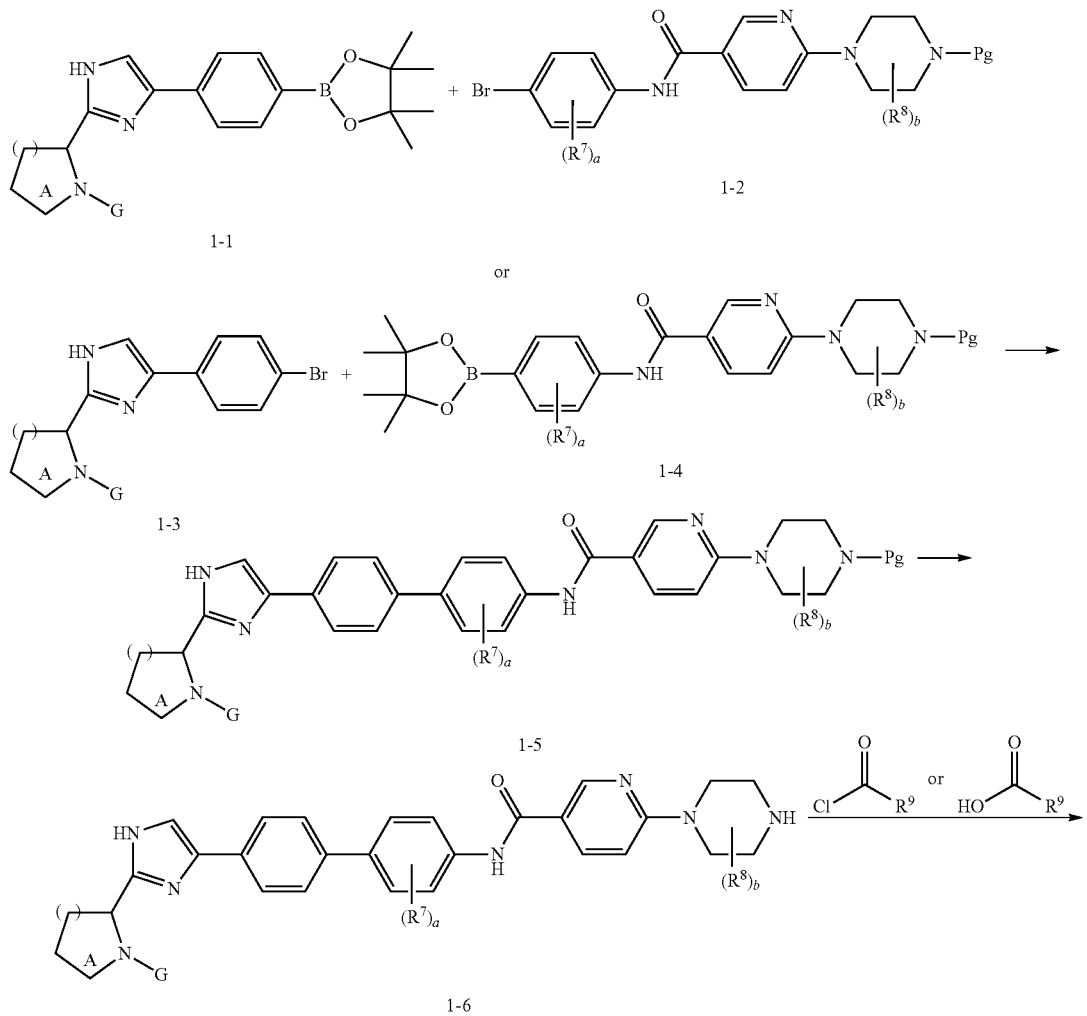

-continued

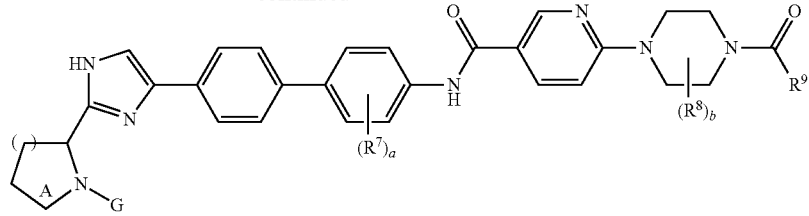

1-7 where 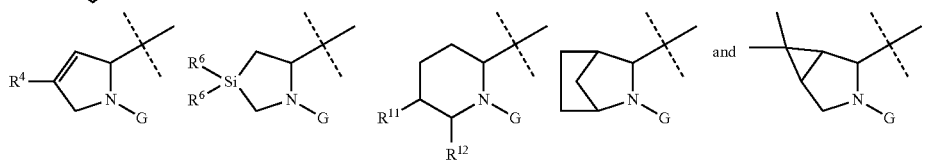 represents and Pg reprents an amino-protecting group. Protected intermediate 1-5 formed by the Suzuki coupling reaction, is then deprotected, for example, by treatment with an acid to provide compound 1-6 which is reacted with an acid chloride in the presence of base or with a carboxylic acid under amide bond formation conditions to prepare a compound of the invention of formula 1-7. When a carboxylic acid reagent HO—C(O)—$R^9$ is used for the amide bond formation reaction, a coupling agent such as N,N,N',N'-tetramethyl-O-(7-azabenzotriazol-1-yl)uronium hexafluorophosphate (HATU) or other coupling agents known in the art, is typically included in the reaction.

If protected intermediate 1-2 were replaced by an intermediate 1-2'

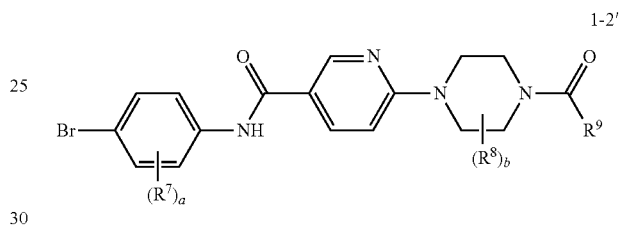

1-2' then the Suzuki coupling of the boronate 1-1 in the first step of Scheme 1A would directly provide a final compound of the invention.

Another useful sequence for preparing final compounds of the invention is illustrated in Scheme 1B:

Scheme 1B

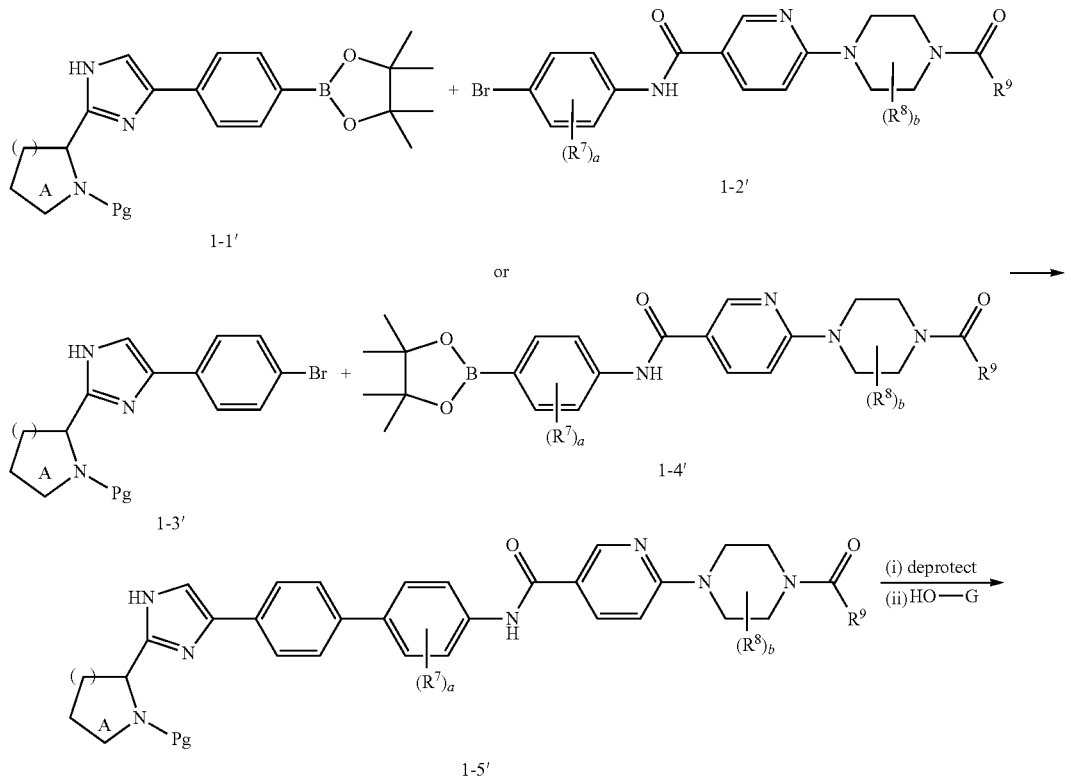

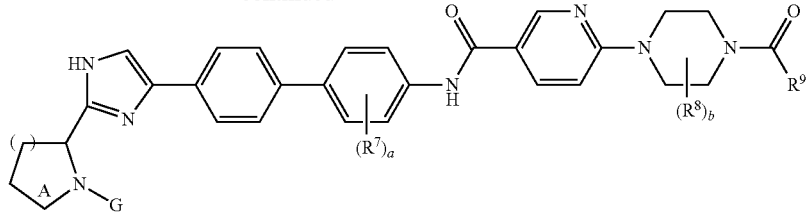

1-7 where a protected form of the Suzuki coupling partners 1-1' or 1-3' in which the nitrogen on the ring labeled as A bears a protecting group Pg, and intermediates 1-2' or 1-4' bearing the substituent $R^9$, are used in the first step to form a protected intermediate 1-5'. The protected intermediate 1-5' is (i) deprotected conventionally, and then (ii) reacted with a reagent HO-G to provide a compound of the invention.

The bromo intermediate 1-2 may be prepared, for example, by amide coupling of arylamine 2-1 with a fluoropyridine carbonyl chloride 2-2, followed by reaction with a protected piperazine 2-4 as shown in Scheme 2.

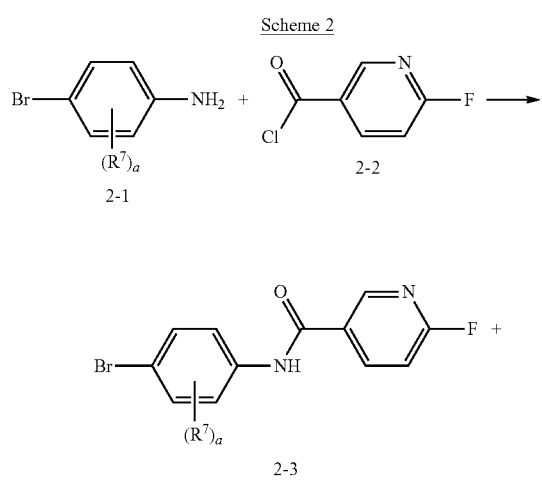

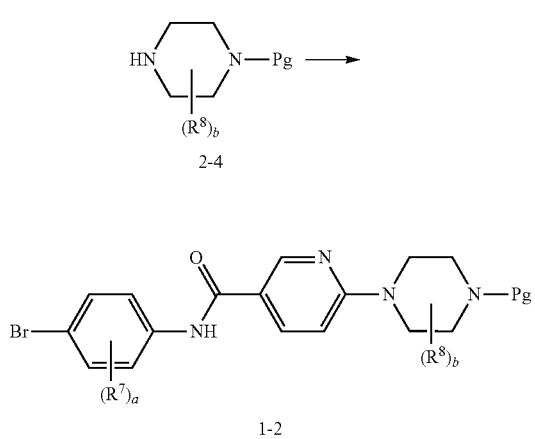

Alternatively, intermediate 1-2 may be prepared by the reaction of arylamine 2-1 with the carboxylic acid intermediate 3-1 as given in Scheme 3.

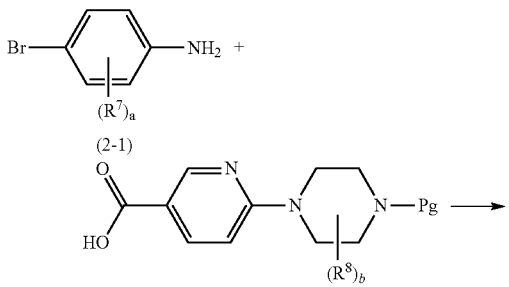

It will be readily understood that intermediates bearing the substituent $R^9$ may be prepared from the corresponding protected compound. For example, the bromo intermediate 1-2', may be prepared by deprotecting intermediate 1-2 and then reacting with an acid chloride or carboxylic acid as in Scheme 1A.

A process for the preparation of intermediate 3-1 is given in the following scheme.

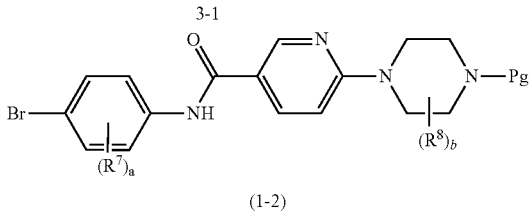

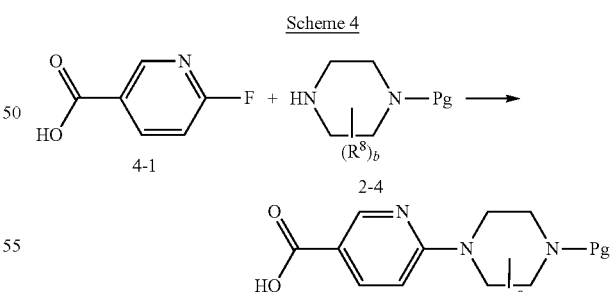

The reaction in Scheme 4 of a fluoronicotinic acid 4-1 with the protected piperazine 2-4 to provide intermediate 3-1 is typically performed using isopropylmagnesium chloride at a temperature below about −20° C.

Intermediates 1-1 and 1-3 used in the Suzuki reaction of Scheme 1 may be prepared, for example, as shown in Schemes 5 and 6.

Scheme 5

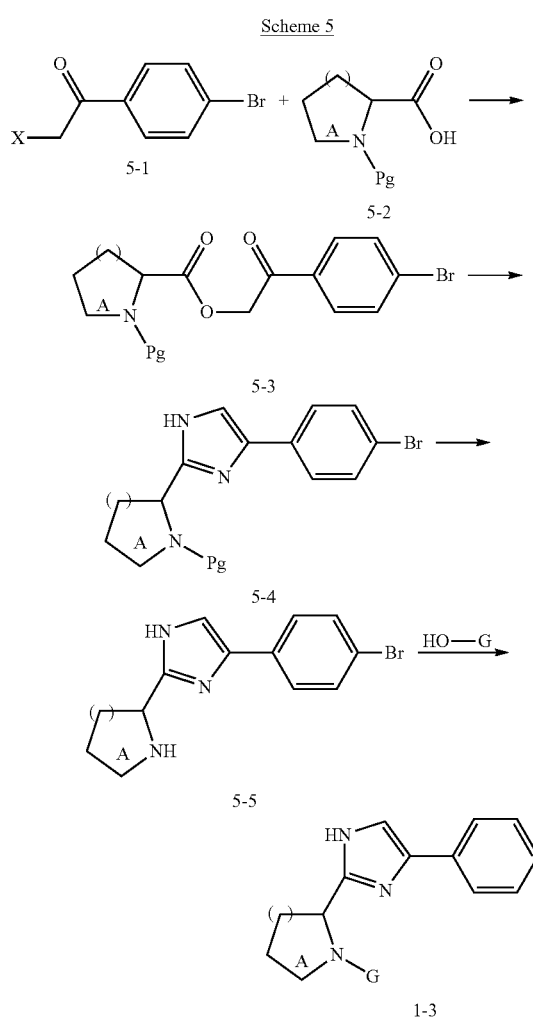

Reagent 5-1, where X represents bromo or chloro, is reacted with a protected proline or piperidine carboxylic acid 5-2 to provide intermediate 5-3 which is converted to intermediate 5-4 in the presence of an excess of ammonium acetate. The ring closure reaction typically is performed at a temperature between about 100° C. and about 120° C. for a period of about 4 to about 24 hours. To provide compound 1-3, intermediate 5-4 is typically deprotected and coupled with a reagent HO-G to provide compound 1-3.

Finally, to provide boronate intermediate 1-1, intermediate 1-3 is reacted with the di-boronate 6-1 in the presence of a palladium catalyst as shown in Scheme 6.

Scheme 6

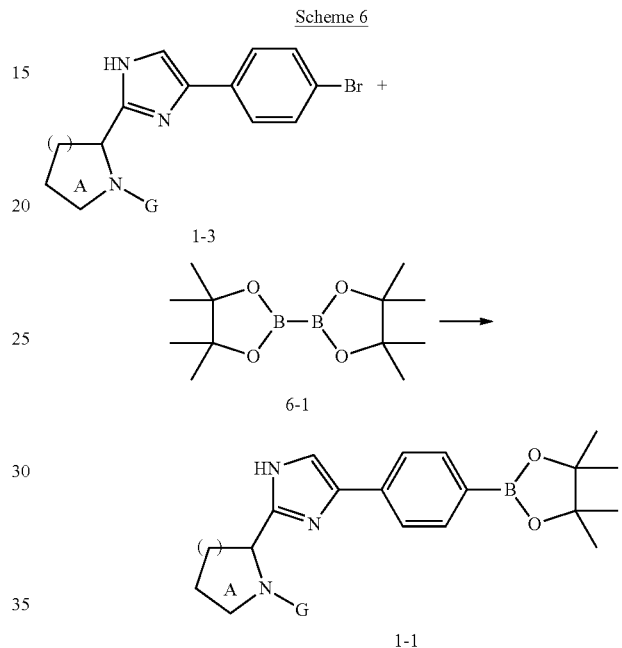

Compounds of Formula 7-5 in which the variable $A_m$ is defined as —C(O)NH— are prepared by processes analogous to those described above. One exemplary process for the preparation of compounds of Formula 7-5 is shown in Scheme 7.

Scheme 7

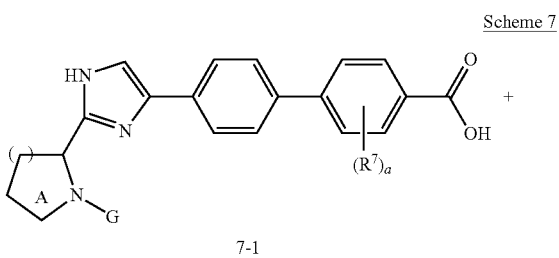

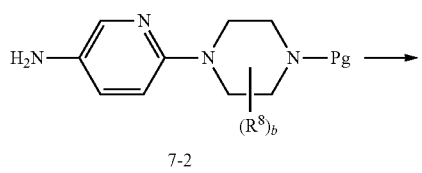

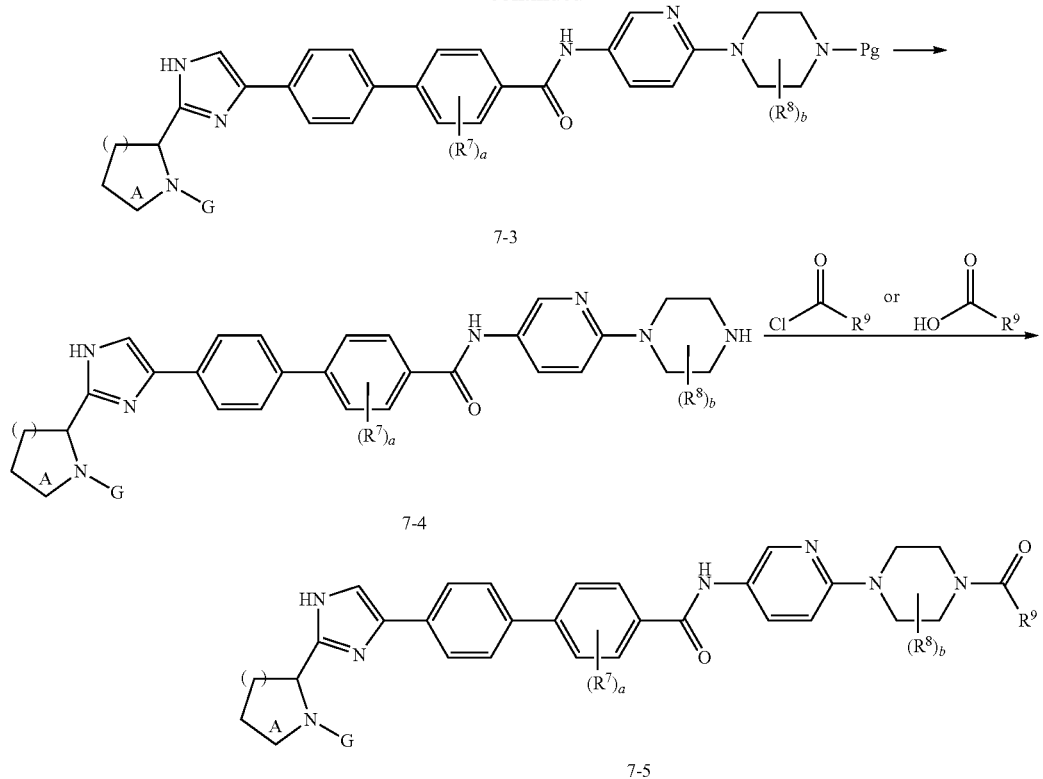

The acid 7-1 and aminopyridine 7-2 are reacted under amide bond formation conditions to provides a protected intermediate of formula 7-3 which is then deprotected and reacted with an acid chloride or carboxylic acid as in Scheme 1 to provide final compounds of the invention.

The intermediates of Scheme 7 may be prepared by conventional synthetic reactions. For example, the bi-phenyl acid 7-1 may be prepared by the Suzuki coupling reaction of boronate intermediate 1-1 with a bromo-benzoic acid ester followed by hydrolysis to the acid (not shown) to provide the bi-phenyl acid 7-1.

Scheme 8

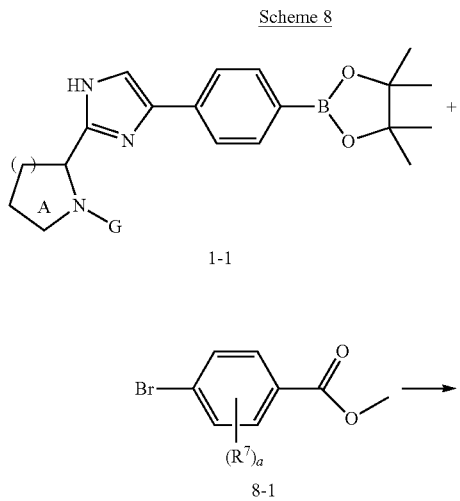

Alternatively, compounds of formula 7-5 may be prepared by the Suzuki coupling of boronate intermediate 1-1 with a bromo intermediate analogous to intermediate 1-2 of Scheme 1.

Compounds of formula (II) may be prepared by analogous reactions using napthimidazole bromide or boronate reagents

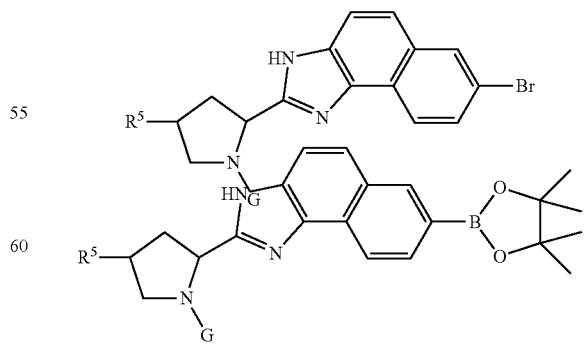

in place of intermediates 1-1 and 1-3 in, for example Scheme 1 and Scheme 8 and following reactions.

Details regarding specific reaction conditions and other procedures for preparing representative compounds of the invention or intermediates thereto are described in the examples below.

Thus, in one of its method aspects, the invention provides the processes of the schemes and variations thereto described above as well as the processes exemplified below.

It will further be understood, this disclosure encompasses compounds of formula (I) when prepared by synthetic processes such as those described above and below or by metabolic processes including those occurring in vivo in human or animal body or in vitro.

Pharmaceutical Compositions

The compounds of the invention and pharmaceutically-acceptable salts thereof are typically used in the form of a pharmaceutical composition or formulation. Such pharmaceutical compositions may be administered to a patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a compound of formula (I), where, as defined above, "compound of formula (I)" means a compound of formula (I) or a pharmaceutically-acceptable salt thereof. Optionally, such pharmaceutical compositions may contain other therapeutic and/or formulating agents if desired. When discussing compositions and uses thereof, the "compound of the invention" may also be referred to herein as the "active agent". As used herein, the term "compound of the invention" is intended to include all compounds encompassed by formulas (I) and (II) as well as the species embodied in formulas (III), through (XI) and pharmaceutically-acceptable salts thereof The pharmaceutical compositions of the invention typically contain a therapeutically effective amount of a compound of the present invention. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.1 to about 95% by weight of the active agent; preferably, from about 5 to about 70% by weight; and more preferably from about 10 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise the active agent and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid methacrylic acid ester copolymers, cellulose acetate trimellitate, carboxymethyl ethyl cellulose, hydroxypropyl methyl cellulose acetate succinate, and the like.

Pharmaceutical compositions of the invention may also be formulated to provide slow or controlled release of the active agent using, by way of example, hydroxypropyl methyl cellulose in varying proportions; or other polymer matrices, liposomes and/or microspheres. In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The compounds of this invention can also be administered parenterally (e.g. by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations may be rendered sterile by use of a sterile injectable medium, a sterilizing agent, filtration, irradiation, or heat.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The compounds of the invention can also be administered transdermally using known transdermal delivery systems and excipients. For example, the active agent can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

The following non-limiting examples illustrate representative pharmaceutical compositions of the present invention.

Oral Solid Dosage Form

A compound of the invention is dissolved in polyethylene glycol acidified to pH≤2 with optional heating to form a solution comprising 10% w/w or 40% w/w active agent. The solution is spray dried to form a powder. The resulting powder is loaded into capsules, for example gelatin or hydroxypropyl methylcellulose capsules, to provide a unit dosage of 14 mg or 56 mg, respectively, active agent per capsule.

Oral Liquid Formulation

A compound of the invention (100 mg) is added to a mixture of ethanol (5 mL), propylene glycol (10 mL), and polyethylene glycol (25 mL). Once dissolution is achieved, acidified distilled water (q.s. to 100 mL) is added to provide a liquid formulation at a concentration of 1 mg/mL active agent.

Lipid Emulsion Formulation

A lipid emulsion formulation comprising a compound of the invention (10%), oleic acid (78%) polyethylene glycol (10%), and polysorbate 20 (2%) w/w is formed by adding a compound of the invention to a mixture of the remaining ingredients.

Lipid Emulsion Formulation

A lipid emulsion formulation comprising a compound of the invention (10%) and oleic acid (90%) w/w is formed by adding a compound of the invention to oleic acid.

Micro-Emulsion Formulation

A compound of the invention (1 g) is dissolved in a mixture of ethanol (2 mL), propylene glycol (2 mL), polyethylene glycol 400 (4 mL), and polyethylene glycol-15-hydroxystearate (4 mL). Acidified distilled water (q.s. to 100 mL) is added to form a self-emulsifying micro-emulsion formulation.

Utility

The compounds of the invention have been shown to inhibit viral replication in HCV replicon assays and therefore are expected to be useful for the treatment of hepatitis C viral infections.

In one aspect, therefore, the invention provides a method of inhibiting replication of the hepatitis C virus in a mammal (e.g., a human), the method comprising administering to the mammal a therapeutically-effective amount of a compound of the invention or of a pharmaceutical composition comprising a pharmaceutically-acceptable carrier and a compound of the invention.

The invention further provides a method of treating hepatitis C viral infections in a mammal (e.g., a human), the method comprising administering to the mammal a therapeutically-effective amount of compound of the invention or of a pharmaceutical composition comprising a pharmaceutically-acceptable carrier and a compound of the invention.

The compounds of the invention may inhibit viral replication by inhibiting the function of the NS5A protein encoded by the HCV genome. In one aspect, therefore, the invention provides a method of inhibiting the NS5A protein of HCV in a mammal, the method comprising administering to the mammal, a compound or a composition of the invention.

When used to treat HCV infections, the compounds of the invention will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating HCV infections will range from about 1 to about 2000 mg/day of active agent, including from about 5 to about 300 mg/day and from about 10 to about 200 mg per day of active agent for an average 70 kg human.

Combination Therapy

Compounds of the invention may also be used in combination with one or more agents which act by the same mechanism or by different mechanisms to effect treatment of HCV. Useful classes of agents for combination therapy include, but are not limited to, HCV NS3 protease inhibitors, HCV NS5B nucleoside and non-nucleoside polymerase inhibitors, helicase inhibitors, NS4B protein inhibitors, HCV viral entry inhibitors, cyclophyllin inhibitors, toll-like receptor agonists, inhibitors of heat shock proteins, interfering RNA, antisense RNA, HCV internal ribosome entry site (IRES) inhibitors, thiazolides, nucleoside analogs such as ribavirin and related compounds, interferons and other immunomodulatory agents, inosine 5'-monophosphate dehydrogenase (IMPDH) inhibitors, and other NS5A protein inhibitors. Agents which act to inhibit HCV replication by any other mechanism may also be used in combination with the present compounds.

HCV NS3 protease inhibitors which may be used in combination therapy include, but are not limited to, Incivek® (telaprevir, VX-950), boceprevir (SCH-503034), simeprevir (TMC-435), narlaprevir (SCH-900518), vaniprevir (MK-7009), danoprevir (ITMN-191, R-7227), BI-201335, ABT-450/r, asunaprevir (BMS-650032), GS-9256, GS-9451, sovaprevir (ACH-1625), ACH-2684, BMS-605339, VX-985, PHX-1766, BMS-791325, IDX-320, and MK-5172.

Examples of HCV NS5B nucleoside polymerase inhibitors include, but are not limited to, mericitabine (RG7128), IDX-184, sofosbuvir (GS-7977, PSI-7977), PSI-7851, PSI-938, BMS-986094 (INX-189, INX-08189), RG7348, MK-0608, TMC-649128, HCV-796, and ALS-2200 (VX-135), while, non-nucleoside HCV NS5B polymerase inhibitors, include but are not limited to, filibuvir (PF-8685540), tegobuvir (GS-9190), VX-222, VX-759, setrobuvir (ANA-598), ABT-072, ABT-333, BI-207127, BMS-791325, MK-3281, IDX-37, BMS-824393, TMC-647055.

A wide variety of interferons and pegylated interferons, including alpha, beta, omega, and gamma interferons, having antiviral, antiproliferative or immunomodulatory effects, can be combined with the present compounds. Representative examples include, but are not limited to, Intron® A (interferon-alpha2b), Actimmune® (interferon-gamma-1b), Alferon N, Advaferon®, Roferon-A (interferon alpha-2a) PegIntron® (peginterferon-alpha 2b), Alfaferone, Pegasys® (peginterferon alpha-2a), Alfanative (interferon alpha), Zalbin™ (albinterferon alpha-2b), Infergon® (interferon alfacon-1), Omega DUROS® (omega interferon), Locteron™ (interferon alpha), PEG-rIL-29 (pegylated interferon lambda), and Rebif® (interferon beta-1a).

Nucleoside analog antiviral agents include, but are not limited to, ribavirin (Copegus®, Rebetol®, Virazole®) and Viramidine (taribavirin). Interferons and ribavirin are also provided in the form of kits which include, for example, but are not limited to, Rebetron® (interferon alpha-2b/ribavirin) and Pegetron® (Peginterferon alpha-2b/ribavirin)

Useful compounds acting by other mechanisms include, but are not limited to: cyclophilin inhibitors, such as DEB-025, SCY-635, NIM-811, and cyclosporine and derivatives; toll-like receptor agonists, such as resiquimod, IMO-2125, and ANA-773, HCV viral entry inhibitors, such as civacir, thiazolides, such as nitazoxanide, and broad-spectrum viral inhibitors, such as, inosine-5'-monophosphate dehydrogenase (IMPDH) inhibitors.

In addition, compounds of the invention may be combined with an NS5A inhibitor, for example, daclatasvir (BMS-790052), AZD-7295, PPI-461, PPI-1301, GS-5885, GSK2336805, ABT-267, ACH-2928, ACH-3102, EDP-239, IDX-719, MK-8742, or PPI-668.

In another aspect, therefore, the invention provides a therapeutic combination for use in the treatment of hepatitis C viral infections, the combination comprising a compound of the invention and one or more other therapeutic agents useful for treating HCV. For example, the invention provides a combination comprising a compound of the invention and one or more agents selected from HCV NS3 protease inhibitors, HCV NS5B nucleoside and non-nucleoside polymerase inhibitors, interferons and pegylated interferons, cyclophilin inhibitors, HCV NS5A inhibitors, and ribavirin and related nucleoside analogs. Also provided, therefore, is a pharmaceutical composition comprising a compound of the invention and one or more other therapeutic agents useful for treating HCV.

Further, in a method aspect, the invention provides a method of treating a hepatitis C viral infection in a mammal, the method comprising administering to the mammal a compound of the invention and one or more other therapeutic agents useful for treating HCV.

In another method aspect, the invention provides a method of inhibiting replication of the hepatitis C virus in a mammal, the method comprising administering to the mammal a compound of the invention and one or more other therapeutic agents useful for inhibiting replication of the hepatitis C virus.

For example, in one method aspect, the invention provides a method of treating a hepatitis C viral infection in a mammal, the method comprising administering to the mammal a compound of the invention, an interferon or pegylated interferon, and ribavirin.

In another exemplary method aspect, the invention provides a method of treating a hepatitis C viral infection in a mammal, the method comprising administering to the mammal a compound of the invention, an interferon or pegylated interferon, ribavirin, and an HCV NS3 protease inhibitor.

In still another method aspect, the invention provides a method of treating a hepatitis C viral infection in a mammal, the method comprising administering to the mammal a compound of the invention, an HCV NS3 protease inhibitor, and ribavirin.

Still other all-oral combination therapies useful in other method aspects, include, for example, a compound of the invention and an HCV NS3 protease inhibitor; a compound of the invention and an HCV NS5B nucleoside polymerase inhibitor; a compound of the invention, an HCV NS5B nucleoside polymerase inhibitor, and ribavirin; a compound of the invention, an HCV NS3 protease inhibitor, and an HCV NS5B nucleoside polymerase inhibitor; a compound of the invention, an HCV NS3 protease inhibitor, an HCV NS5B nucleoside polymerase inhibitor and ribavirin; a compound of the invention, an HCV NS3 protease inhibitor, and an HCV NS5B non-nucleoside polymerase inhibitor; and a compound of the invention, an HCV NS3 protease inhibitor, an HCV NS5B non-nucleoside polymerase inhibitor and ribavirin.

In another method aspect, the invention provides a method of inhibiting replication of the hepatitis C virus in a mammal, using a compound of the invention in combination with other agents, as described above.

When used in combination therapy, the agents may be formulated in a single pharmaceutical composition, as disclosed above, or the agents may be provided in separate compositions that are administered simultaneously or at separate times, by the same or by different routes of administration. When administered separately, the agents are administered sufficiently close in time so as to provide a desired therapeutic effect. Such compositions can be packaged separately or may be packaged together as a kit. The two or more therapeutic agents in the kit may be administered by the same route of administration or by different routes of administration.

Finally, the compounds of the invention may also find utility as research tools, for example, for discovering new HCV NS5A protein inhibitors or explicating mechanisms of HCV replication.

Compounds of the invention have been demonstrated to be potent inhibitors of HCV replication in HCV replicon assays, as described in the following examples.

EXAMPLES

The following synthetic and biological examples are offered to illustrate the invention, and are not to be construed in any way as limiting the scope of the invention.

In the examples below, the following abbreviations have the following meanings unless otherwise indicated. Abbreviations not defined below have their generally accepted meanings.

ACN=acetonitrile
DCM=dichloromethane
DIPEA=N,N-diisopropylethylamine
DMA=N,N-dimethylacetamide
DMF=N,N-dimethylformamide
DMP=1,1,1-triacetoxy-1,1-dihydro-1,2-benziodoxol-3 (1H)-one (Dess-Martin periodinane)
DMSO=dimethyl sulfoxide
EDC=N-(3-dimethylaminopropyl)-N-ethylcarbodiimide hydrochloride
EtOAc=ethyl acetate
h=hour(s)
HATU=N,N,N',N'-tetramethyl-O-(7-azabenzotriazol-1-yl)uronium hexafluorophosphate
HCTU=2-(6-chloro-1H-benzotriazole-1-yl)-1,1,3,3-tetramethylaminium hexafluorophosphate
HOAt=1-hydroxy-7-azabenzotriazole
min=minute(s)
Pd(dppf)Cl$_2$=dichloro(1,1'-bis(diphenylphosphino)-ferrocene)dipalladium(II)
Pd(PPh$_3$)4=tetrakis(triphenylphosphine)palladium(0)
MTBE=methyl tert-butyl ether
RT=room temperature
TFA=trifluoroacetic acid
THF=tetrahydrofuran
bis(pinacolato)diboron=4,4,5,5,4',4',5',5'-octamethyl-[2,2']bi[[1,3,2]dioxaborolanyl]

Reagents and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry. Reaction mixtures were worked up as described specifically in each reaction; commonly they were purified by extraction and other purification methods such as temperature-, and solvent-dependent crystallization, and precipitation. In addition, reaction mixtures were routinely purified by preparative HPLC, typically using C18 or BDS column packings and conventional eluents. Typical preparative HPLC conditions are described below.

Characterization of reaction products was routinely carried out by mass and $^1$H-NMR spectrometry. For NMR analysis, samples were dissolved in deuterated solvent (such as CD$_3$OD, CDCl$_3$, or d$_6$-DMSO), and $^1$H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, Calif.) model API 150 EX instrument or an Agilent (Palo Alto, Calif.) model 1200 LC/MSD instrument.

| General Preparative HPLC Conditions | |
| --- | --- |
| Column: | C18, 5 μm. 21.2 × 150 mm or C18, 5 μm 21 × 250 or C14 21 × 150 |
| Column temperature: | Room Temperature |
| Flow rate: | 20.0 mL/min |
| Mobile Phases: | A = Water + 0.05% TFA |
| | B = ACN + 0.05% TFA, |
| Injection volume: | (100-1500 μL) |
| Detector wavelength: | 214 nm |

Crude compounds were dissolved in 1:1 water:acetic acid at about 50 mg/mL. A 4 minute analytical scale test run was carried out using a 2.1×50 mm C18 column followed by a 15 or 20 minute preparative scale run using 100 μL injection with the gradient based on the % B retention of the analytical scale test run. Exact gradients were sample dependent. Samples with close running impurities were checked with a 21×250 mm C18 column and/or a 21×150 mm C14 column for best separation. Fractions containing desired product were identified by mass spectrometric analysis.

| Supercritical Fluid Chromatography (SFC) Conditions | |
| --- | --- |
| Instrument | Thar 80 |
| Column: | AD 5 μm 30 × 250 mm |
| Column temperature: | 38° C. |
| Nozzle pressure: | 100 Bar |
| Nozzle temperature: | 60° C. |
| Evaporator temperature: | 20° C. |
| Trimmer temperature: | 25° C. |
| Injection volume: | (100-1500 μL) |
| Detector wavelength: | 220 nm |

Preparation 1: 4-(4-Bromo-phenyl)-2-((S)-4-methyl-2,5-dihydro-1H-pyrrol-2-yl)-1H-imidazole

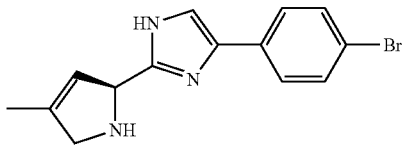 [SMILES: CC1=C[C@@H](c2nc(-c3ccc(Br)cc3)c[nH]2)NC1]

(a) (2S,4R)-4-Hydroxy-pyrrolidine-2-carboxylic acid methyl ester

Thionyl chloride (47 g, 393 mmol) was added dropwise at 0° C. to a stirred solution of (2S,4R)-4-hydroxy-pyrrolidine-2-carboxylic acid (40 g, 0.31 mol) in anhydrous methanol (200 mL). The reaction was allowed to proceed overnight, and concentrated to give the title intermediate (50 g). $^1$H NMR (400 MHz, CD$_3$OD) δ (ppm) 4.56 (m, 2H), 3.85 (s, 3H), 3.41 (m, 1H), 3.28 (m, 1H), 2.40 (m, 1H), 2.22 (m, 1H).

(b) (2S,4R)-4-Hydroxy-pyrrolidine-1,2-dicarboxylic acid 1-tert-butyl ester 2-methyl ester To a solution of the product of the previous step (1 g, 6.89 mmol) in DCM (500 mL) was added triethylamine (68.8 g) and di-tert-butyl dicarbonate (74.2 g, 0.34 mmol). The mixture was stirred at RT overnight, washed with 1 M HCl (50 mL), brine, dried over Na$_2$SO$_4$, filtered and concentrated to give the title intermediate (45 g). $^1$H NMR (400 MHz, CDCl$_3$): δ (ppm) 4.44 (m, 1H), 4.34 (m, 1H), 3.70 (s, 3H), 3.56 (m, 1H), 3.43~3.53 (m, 1H), 2.25~2.30 (m, 2H), 2.03 (m, 1H), 1.35~1.44 (m, 9H).

(c) (S)-4-Oxo-pyrrolidine-1,2-dicarboxylic acid 1-tert-butyl ester 2-methyl ester To a solution of the product of the previous step (45 g, 0.18 mol) in DCM (500 mL) was added portionwise pyridinium chlorochromate (77.6 g, 0.36 mol). The mixture was stirred at RT overnight and filtered through Celite®. The filtrate was concentrated and purified by column chromatography (20% EtOAc in petroleum ether) to give the title intermediate (20 g, 46% yield). $^1$H NMR (400 MHz, CDCl$_3$): δ (ppm) 4.72 (m, 1H), 3.87~3.90 (m, 2H), 3.73 (s, 3H), 2.88~2.99 (m, 1H), 2.56 (m, 1H), 1.42 (s, 9H).

(d) (S)-4-Trifluoromethanesulfonyloxy-2,5-dihydro-pyrrole-1,2-dicarboxylic acid 1-tert-butyl ester 2-methyl ester To a stirred solution of 1 M sodium hexamethyldisilazane (41.1 mL, 41.10 mmol) was added a stirred solution of the product of the previous step (10 g, 41.10 mmol) in dry THF (80 mL) at −78° C. under N$_2$. The reaction mixture was stirred at −78° C. for 30 min and then a solution of N-phenyl-bis(trifluoromethanesulfonimide) (15.4 g, 43.16 mmol) in THF (100 mL) was added dropwise and the mixture stirred for another 2 h. The reaction was quenched with NaHCO$_3$ (aq) and extracted with EtOAc (3×100 mL). The combined organic phase was washed with brine, dried over Na$_2$SO$_4$, filtered, concentrated and purified by column chromatography (2% EtOAc in petroleum ether) to give the title intermediate (3.5 g, 23% yield). $^1$H NMR (400 MHz, CDCl$_3$): δ (ppm) 5.73 (m, 1H), 5.00~5.07 (m, 1H), 4.24~4.39 (m, 2H), 3.76 (s, 3H), 1.42~1.47 (m, 9H).

(e) (S)-4-Methyl-2,5-dihydro-pyrrole-1,2-dicarboxylic acid 1-tert-butyl ester 2-methyl ester To a solution of the product of the previous step (3.5 g, 9.33 mmol) in dioxane (50 mL) was added methylboronic acid (1.12 g, 18.66 mmol), Na$_2$CO$_3$ (9.33 mL, 18.66 mmol, 2 M) and Pd(PPh$_3$)4 (1.08 g, 0.93 mmol). The reaction mixture was heated at reflux for 2 h under nitrogen, cooled to RT, filtered, and the filtrate was concentrated and purified by column chromatography (2% EtOAc in petroleum ether) to give the title intermediate (1.4 g, 62% yield). $^1$H NMR (400 MHz, CDCl$_3$): δ (ppm) 5.28~5.35 (m, 1H), 4.86~4.88 (m, 1H), 4.02~4.15 (m, 2H), 3.71 (s, 3H), 1.76 (s, 3H), 1.40~1.46 (m, 9H).

(f) (S)-4-Methyl-2,5-dihydro-pyrrole-1,2-dicarboxylic acid 1-tert-butyl ester

To a solution of the product of the previous step (1.4 g, 5.80 mmol) in 2:1 THF:water (30 mL) was added aq. lithium hydroxide (730 mg, 17.4 mmol). The mixture was stirred at RT overnight under nitrogen, adjusted to pH 2 with 1 N HCl, and extracted with EtOAc (3×50 mL). The combined organic phase was washed with brine, dried over Na$_2$SO$_4$, filtered and concentrated to give the title intermediate (1.3 g)

(g) (S)-4-Methyl-2,5-dihydro-pyrrole-1,2-dicarboxylic acid 2-[2-(4-bromo-phenyl)-2-oxo-ethyl]ester 1-tert-butyl ester To a solution of the product of the previous step (1.3 g, 5.72 mmol) in ACN (30 mL) was added diethylamine (2.22 g, 17.16 mmol) and 2-bromo-1-(4-bromo-phenyl)-ethanone (2.38 g, 8.58 mmol). The reaction mixture was stirred at RT for 2 h, and diluted with 1:1 EtOAc:water (100 mL). The organic layer was dried over Na$_2$SO$_4$, filtered and concentrated to give the title intermediate (2.4 g).

(h) (S)-2-[4-(4-Bromo-phenyl)-1H-imidazol-2-yl]-4-methyl-2,5-dihydro-pyrrole-1-carboxylic acid tert-butyl ester To a solution of the product of the previous step (2.4 g, 5.66 mmol) in toluene (40 mL) was added ammonium acetate (8.72 g, 112 mmol). The reaction mixture was heated at reflux overnight under nitrogen, concentrated, and the residue was dissolved in EtOAc (50 mL) and H$_2$O (50 mL). The aqueous layer was extracted with EtOAc (2×50 mL). The combined organic fractions were dried over Na$_2$SO$_4$, filtered, concentrated and purified by column chromatography (10%-50% EtOAc in petroleum ether) to give the title intermediate (1.4 g, 61% yield). (m/z): [M+H]$^+$ calcd for C$_{19}$H$_{22}$BrN$_3$O$_2$ 404.09, 406.09 found 404.1, 406.1.

(i) 4-(4-Bromo-phenyl)-2-((S)-4-methyl-2,5-dihydro-1H-pyrrol-2-yl)-1H-imidazole

To a cooled (0° C.) solution of the product of the previous step (1.4 g, 3.46 mmol) in DCM (10 mL) was added HCl/dioxane (10 mL). The mixture was stirred at RT for 3 h.

The mixture was concentrated to give the title intermediate (1 g). m/z: [M+H]⁺ calcd for $C_{14}H_{14}BrN_3$ 304.04, 306.04 found 304.0, 306.0.

Preparation 2: (S)-2-Methoxycarbonylamino-3-methyl-butyric acid

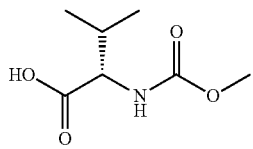

Methylchloroformate (14.5 mL, 0.188 mol) was added over 15 min to a cooled (0-6° C.) mixture of (S)-2-amino-3-methyl-butyric acid (20.0 g, 0.171 mol), NaOH (6.80 g, 0.171 mol) and sodium carbonate (18.1 g, 0.171 mol) in water (200 mL). The cooling bath was removed and the mixture was stirred at ambient temperature overnight. Conc. aqueous HCl (30 mL) was added to the reaction mixture to adjust pH to ~1. A solid formed and the mixture was stirred for 90 min. The mixture was filtered and the solid was dried overnight under reduced pressure at 40° C. t to provide the title intermediate (27.8 g, 93% yield). ¹H NMR (CD₃OD, 400 MHz) δ (ppm) 4.87 (br. s, 2H), 4.05 (d, J=5.49, 1H), 3.65 (s, 3H), 2.25-2.05 (m, 1H), 0.98 (d, J=6.87, 3H), 0.94 (d, J=6.87, 3H).

Preparation 3: ((S)-1-{(S)-2-[4-(4-Bromo-phenyl)-1H-imidazol-2-yl]-4-methyl-2,5-dihydro-pyrrole-1-carbonyl}-2-methyl-propyl)-carbamic acid methyl ester

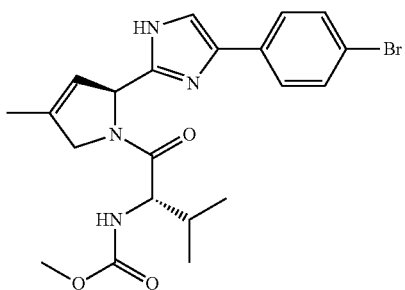 [SMILES: COC(=O)N[C@H](C(=O)N1CC(C)=C[C@H]1c1nc(-c2ccc(Br)cc2)c[nH]1)C(C)C]

To a solution of 4-(4-bromo-phenyl)-2-((S)-4-methyl-2,5-dihydro-1H-pyrrol-2-yl)-1H-imidazole (1.10 g, 3.62 mmol) in DCM (50 mL) was added DIPEA (2.34 g, 18.1 mmol), (S)-2-methoxycarbonylamino-3-methyl-butyric acid (761 mg, 4.34 mmol) and HATU (1.65 g, 4.34 mmol). The mixture was stirred at RT overnight, washed with water (50 mL) and brine (50 mL), dried over Na₂SO₄, filtered, concentrated and purified by column chromatography (10%-50% EtOAc in petroleum ether) to give the desired product, which was purified by supercritical fluid chromatography (SFC) [mobile phase A: supercritical CO₂, phase B: methanol+0.05% diethylamine; flow rate: 80 mL/min] to give the title intermediate (750 mg, 45% yield). m/z: [M+H]⁺ calcd for $C_{21}H_{25}BrN_4O_3$ 461.11, 463.11 found 461.1.

Preparation 4: [(S)-2-Methyl-1-((S)-4-methyl-2-{4-[4-(4,4,5,5-tetramethyl-[1,3,2]dioxaborolan-2-yl)-phenyl]-1H-imidazol-2-yl}-2,5-dihydro-pyrrole-1-carbonyl)-propyl]-carbamic acid methyl ester

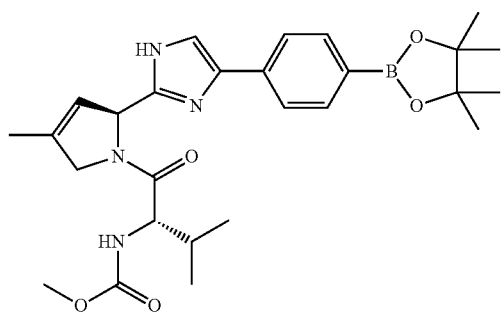

To a solution of ((S)-1-{(S)-2-[4-(4-bromo-phenyl)-1H-imidazol-2-yl]-4-methyl-2,5-dihydro-pyrrole-1-carbonyl}-2-methyl-propyl)-carbamic acid methyl ester (520 mg, 1.13 mmol) in dioxane (20 mL) was added bis(pinacolato)diboron (430 mg, 1.69 mmol), potassium acetate (222 mg, 2.26 mmol) and Pd(dppf)Cl₂ (92 mg, 0.113 mmol). The mixture was heated at 90° C. overnight under nitrogen, filtered, and the filtrate was extracted with water (50 mL) and EtOAc (50 mL). The organic layer was dried over Na₂SO₄, filtered and concentrated. The resulting material was combined with the product of a separate batch prepared at the 1.62 mmol scale by the same process and purified by column chromatography (20%-50% EtOAc in petroleum ether) to give the title intermediate (750 mg, 54% yield). m/z: [M+H]⁺ calcd for $C_{27}H_{37}BN_4O_5$ 509.29 found 509.4. ¹H NMR (400 MHz, CD₃OD): δ (ppm) 7.70 (m, 2H), 7.62 (m, 2H), 7.31 (s, 1H), 5.79 (m, 1H), 5.47 (m, 1H), 4.56 (m, 2H), 3.63 (s, 3H), 1.95 (m, 1H), 1.86 (s, 3H), 1.33 (s, 9H), 0.87 (m, 6H).

Preparation 5: 4-(4-Bromo-phenyl)-2-((S)-4-cyclopropyl-2,5-dihydro-1H-pyrrol-2-yl)-1H-imidazole

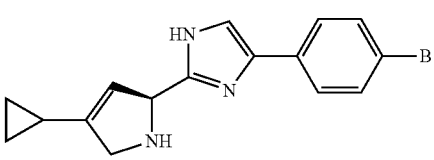

Following the process of Preparation 1 steps (e) through (i) substituting cyclopropylboronic acid for methylboronic acid in Preparation 1 step (e), the title intermediate was prepared. m/z: [M+H]⁺ calcd for $C_{16}H_{16}BrN_3$ 330.05, 332.05 found 330.0, 332.1.

Preparation 6: ((S)-1-{(S)-2-[4-(4-Bromo-phenyl)-1H-imidazol-2-yl]-4-cyclopropyl-2,5-dihydro-pyrrole-1-carbonyl}-2-methyl-propyl)-carbamic acid methyl ester

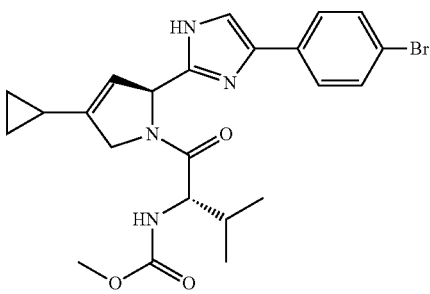 [SMILES: COC(=O)N[C@H](C(=O)N1CC(C2CC2)=C[C@H]1c1nc(-c2ccc(Br)cc2)c[nH]1)C(C)C]

To a solution of 4-(4-bromo-phenyl)-2-((S)-4-cyclopropyl-2,5-dihydro-1H-pyrrol-2-yl)-1H-imidazole (1.8 g, 5.45 mmol) in DCM (30 mL) was added DIPEA (3.52 g, 27.25 mmol), (S)-2-methoxycarbonylamino-3-methyl-butyric acid (1.14 g, 6.54 mmol) and HATU (2.49 g, 6.54 mmol). The mixture was stirred at RT overnight washed with water (50 mL) and brine (50 mL), dried over $Na_2SO_4$, filtered and concentrated. The resulting material was combined with the product of a separate batch prepared at the 0.61 mmol scale by the same process and purified by column chromatography (20%-50% EtOAc in petroleum ether) to give the desired product, which was purified by SFC separation to give the title intermediate (800 mg, 30% yield). m/z): [M+H]$^+$ calcd for $C_{23}H_{27}BrN_4O_3$ 487.13, 489.12 found 487.1.

Preparation 7: [(S)-1-((S)-4-Cyclopropyl-2-{4-[4-(4,4,5,5-tetramethyl-[1,3,2]dioxaborolan-2-yl)-phenyl]-1H-imidazol-2-yl}-2,5-dihydro-pyrrole-1-carbonyl)-2-methyl-propyl]-carbamic acid methyl ester

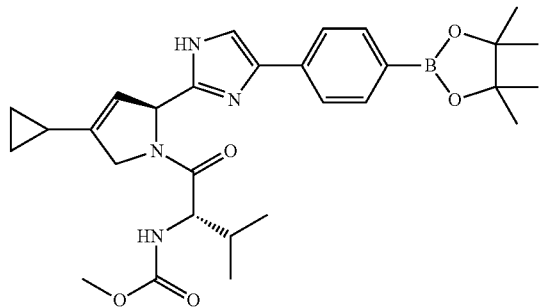 [SMILES: COC(=O)N[C@H](C(=O)N1CC(C2CC2)=C[C@H]1c1nc(-c2ccc(B3OC(C)(C)C(C)(C)O3)cc2)c[nH]1)C(C)C]

To a solution of ((S)-1-{(S)-2-[4-(4-bromo-phenyl)-1H-imidazol-2-yl]-4-cyclopropyl-2,5-dihydro-pyrrole-1-carbonyl}-2-methyl-propyl)-carbamic acid methyl ester (800 mg, 1.64 mmol) in dioxane (30 mL) was added bis(pinacolato) diboron (322 mg, 3.28 mmol), potassium acetate (322 mg, 3.28 mmol) and Pd(dppf)Cl$_2$ (134 mg, 0.164 mmol). The mixture was heated at 90° C. overnight under nitrogen, filtered, and the filtrate was extracted with water (50 mL) and EtOAc (50 mL). The organic layer was washed with water and brine, dried over $Na_2SO_4$, filtered and concentrated. The resulting material was combined with the product of a separate batch prepared at the 1.03 mmol scale by the same process and purified by column chromatography (20%-50% EtOAc in petroleum ether) to give the title intermediate (1.1 g, 77% yield). m/z): [M+H]$^+$ calcd for $C_{29}H_{39}BN_4O_5$ 535.30 found 535.3. $^1$H NMR (400 MHz, CD$_3$OD): δ (ppm) 7.73 (m, 2H), 7.66 (m, 2H), 7.36 (s, 1H), 5.81 (s, 1H), 5.50 (s, 1H), 4.64 (m, 2H), 4.11 (m, 1H), 3.67 (s, 3H), 1.99 (m, 1H), 1.61 (m, 1H), 1.37 (s, 12H), 0.91 (m, 6H), 0.80 (m, 2H), 0.70 (m, 2H).

Preparation 8: (R)-4-[5-(4-Bromo-2-chloro-5-trifluoromethoxy-phenylcarbamoyl)-pyridin-2-yl]-3-methyl-piperazine-1-carboxylic acid tert-butyl ester

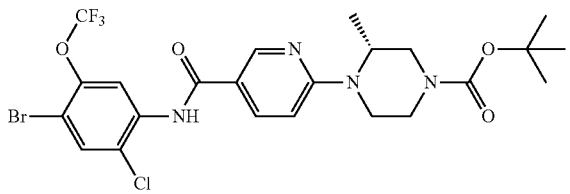 [SMILES: C[C@@H]1CN(C(=O)OC(C)(C)C)CCN1c1ccc(C(=O)Nc2cc(OC(F)(F)F)c(Br)cc2Cl)cn1]

(a) 4-Bromo-2-chloro-5-trifluoromethoxy-phenylamine

To a mixture of 4-bromo-3-trifluoromethoxy-phenylamine (2.0 g, 7.8 mmol) in ACN (60 mL) was slowly added a solution of N-chlorosuccinimide (1.0 g, 7.8 mmol) in ACN (40 mL). The reaction mixture was heated at 60° C. overnight and extracted with ethyl actetate/water. The organic layer was dried over sodium sulfate and purified by flash chromatography (40 g column, 100% hexanes to 10% EtOAc: hexanes) to produce the desired product as an orange-ish-colored oil (1.4 g, 64% yield).

(b) N-(4-Bromo-2-chloro-5-trifluoromethoxy-phenyl)-6-fluoro-nicotinamide

To a solution of the product of the previous step (1.2 g, 4.1 mmol) in DCM (5 mL) was slowly added a solution of 2-fluoropyridine-5-carbonyl chloride (0.66 g, 4.1 mmol) in DCM (3 mL) and 20 drops of DMA were added. The reaction mixture was concentrated to form a yellowish solid (2 g). (m/z): [M+H]$^+$ calcd for $C_{13}H_6BrClF_4N_2O_2$ 412.92, 414.92 found 413, 415.

(c) (R)-4-[5-(4-Bromo-2-chloro-5-trifluoromethoxy-phenylcarbamol)-pyridin-2-yl]-3-methyl-piperazine-1-carboxylic acid tert-butyl ester To a reaction mixture of the product of the previous step (999 mg, 2.42 mmol) in a mixture of N,N-diisopropylethylamine (0.84 mL, 4.83 mmol;) and DMSO (0.86 mL, 12.08 mmol) was added (R)-3-methyl-piperazine-1-carboxylic acid tert-butyl ester (726 mg, 3.62 mmol) and the reaction mixture was heated at 120° C. overnight and extracted with ethyl acetate/water. The organic layer was dried over sodium sulfate and concentrated under vacuum. The dark oil was dissolved in a small amount of DCM and purified by silica gel chromatography (24 g column, 0-40% ethyl acetate:hexanes)

to produce the title intermediate as a white solid (916 mg, 64% yield). (m/z): [M+H]$^+$ calcd for $C_{23}H_{25}BrClF_3N_4O_4$ 593.07, 595.07 found 595.4.

Preparation 9: (R)-5-[4-(4-Bromo-phenyl)-1H-imidazol-2-yl]-3,3-dimethyl-[1,3]azasilolidine

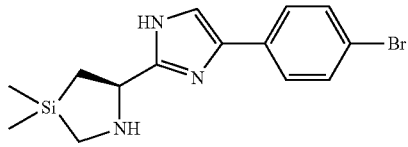 [SMILES: C[Si]1(C)CN[C@H](c2nc(-c3ccc(Br)cc3)c[nH]2)C1]

(a) (2R,5R)-2-[(Chloromethyl-dimethyl-silanyl)-methyl]-5-isopropyl-3,6-dimethoxy-2,5-dihydro-pyrazine To a solution of (R)-2-isopropyl-3,6-dimethoxy-2,5-dihydro-pyrazine (7.0 g, 38 mmol), bis(chloromethyl)dimethylsilane (6.0 g, 38 mmol) in THF (150 mL) was added n-butyllithium (20 mL, 50 mmol) at −65 to −75° C. dropwise. The mixture was allowed to gradually warm to RT overnight. An ammonium chloride solution at 0° C. was added and the reaction mixture was extracted with EtOAc. The organic layer was washed with water and brine, dried over Na$_2$SO$_4$, concentrated, and purified by silica gel chromatography (2% EtOAc in petroleum ether) to give the title intermediate (5 g, 44% yield) as a clear oil $^1$H NMR: (MeOD, 400 MHz) δ (ppm): 4.15 (m, 1H), 3.99 (m, 1H), 3.72 (m, 6H), 2.95 (m, 2H), 2.30 (m, 1H), 1.45 (m, 1H), 1.08 (m, 4H), 0.75 (m, 3H), 0.26 (s, 6H).

(b) (R)-2-Amino-3-(chloromethyl-dimethyl-silanyl)-propionic acid methyl ester

To a solution of the product of the previous step (2.7 g, 8.8 mmol) in MeOH (20 mL) was added HCl solution (7.0 mL). The mixture was stirred at RT for 5 h and concentrated to give the title intermediate (1.3 g) as a yellow oil. (m/z): [M+H]$^+$ calcd for $C_7H_{16}ClNO_2Si$, 210.06 found 210.1.

(c) (S)-3,3-Dimethyl-[1,3]azasilolidine-5-carboxylic acid methyl ester

To a solution of the product of the previous step (1.3 g, 6.2 mmol) and sodium iodide (1.3 g, 8.8 mmol) in 1:1 DCM:THF (100 mL) was added DIPEA (3.0 g, 26 mmol) at RT and the reaction mixture was stirred at RT for 5 h to provide the title intermediate. (m/z): [M+H]$^+$ calcd for $C_7H_{15}NO_2Si$, 174.09 found 174.1.

(d) (S)-3,3-Dimethyl-[1,3]azasilolidine-1,5-dicarboxylic acid 1-tert-butyl ester 5-methyl ester To a solution of the product of the previous step was added di-tert-butyl dicarbonate (1.9 g, 8.8 mmol) at RT. The reaction mixture was stirred at RT for overnight, washed with water and extracted with EtOAc and the organic layer was washed with water and brine, dried over Na$_2$SO$_4$, concentrated, and purified by silica gel chromatography (10:1 petroleum ether: EtOAc) to give the title intermediate (2.0 g) as a clear oil.

(e) (R)-3,3-Dimethyl-[1,3]azasilolidine-1,5-dicarboxylic acid 1-tert-butyl ester A solution of the product of the previous step (2.0 g, 8.8 mmol) and LiOH.H$_2$O (1.6 g, 38.8 mmol) in 1:1 THF:water (50 mL) was stirred at RT overnight, acidified to pH 3-4 with 1 N HCl, and extracted with EtOAc. The organic layer was washed with water and brine, dried over Na$_2$SO$_4$ and concentrated to give the title intermediate (1.6 g) as a clear oil.

(f) (R)-3,3-Dimethyl-[1,3]azasilolidine-1,5-dicarboxylic acid 5-[2-(4-bromo-phenyl)-2-oxo-ethyl] ester 1-tert-butyl ester A mixture of the product of the previous step (1.6 g, 5.7 mmol), 2-bromo-1-(4-bromo-phenyl)-ethanone (1.6 g, 5.7 mmol), and potassium carbonate (2.4 g, 17 mmol) in DCM (100 mL) was stirred at RT for 2 h, washed with water, and extracted with EtOAc. The organic layer was washed with water and brine, dried over Na$_2$SO$_4$, and concentrated to provide the title intermediate (2.5 g, 53% yield) as a yellow oil. (m/z): [M+H−Boc]$^+$ calcd for $C_{14}H_{18}BrNO_3Si$, 356.02 found 356.1.

(g) (R)-5-[5-(4-Bromo-phenyl)-1H-imidazol-2-yl]-3,3-dimethyl-[1,3]azasilolidine-1-carboxylic acid tert-butyl ester A mixture of the product of the previous step (2.5 g, 5.7 mmol), ammonium acetate (10 g, 0.13 mol) in toluene (100 mL) was stirred at 110-130° C. overnight, washed with water, and extracted with EtOAc. The organic layer was washed with water and brine, dried over Na$_2$SO$_4$, concentrated, and purified by silica gel chromatography (8.5% EtOAc in petroleum ether) to give the title intermediate (400 mg, 17% yield) as a brown oil. (m/z): [M+H−Boc]$^+$ calcd for $C_{19}H_{26}BrN_3O_2Si$, 436.10, 438.10 found 438.0. $^1$H NMR (MeOD, 400 MHz) δ (ppm): 7.62 (m, 2H), 7.45 (m, 2H), 7.19 (s, 1H), 5.50 (m, 1H), 2.88 (m, 1H), 2.50 (m, 2H), 1.98 (m, 1H), 1.45 (s, 9H), 1.26 (m, 1H), 0.26 (m, 6H).

(h) (R)-5-[4-(4-Bromo-phenyl)-1H-imidazol-2-yl]-3,3-dimethyl-[1,3]azasilolidine

A solution of the product of the previous step (400 mg, 0.92 mmol) in HCl/MeOH (30 mL) was stirred at RT for 2 h and concentrated to give the title intermediate (350 mg) as a green solid. (m/z): [M+H]$^+$ calcd for $C_{14}H_{18}BrN_3Si$, 336.05 found 336.0.

Preparation 10: ((S)-1-{(R)-5-[4-(4-Bromo-phenyl)-1H-imidazol-2-yl]-3,3-dimethyl-[1,3]azasilolidine-1-carbonyl}-2-methyl-propyl)-carbamic acid methyl ester

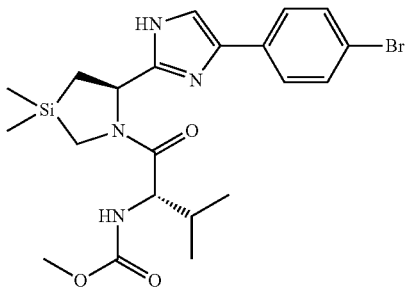 [SMILES: COC(=O)N[C@H](C(=O)N1C[Si](C)(C)C[C@H]1c1nc(-c2ccc(Br)cc2)c[nH]1)C(C)C]

A mixture of (R)-5-[4-(4-bromo-phenyl)-1H-imidazol-2-yl]-3,3-dimethyl-[1,3]azasilolidine (350 mg, 0.92 mmol, Preparation 9), (S)-2-methoxycarbonylamino-3-methyl-butyric acid (170 mg, 0.97 mmol), HATU (400 mg, 1.05 mmol), and DIPEA (700 mg, 5.4 mmol), in DCM (50 mL) was stirred at RT overnight. The reaction mixture was washed with water and brine, dried over Na$_2$SO$_4$, concentrated, and purified by silica gel chromatography (20% EtOAc in petroleum ether) to give the title intermediate (300 mg, 66% yield) as a straw yellow solid. (m/z): [M+H]⁺ calcd for $C_{21}H_{29}BrN_4O_3Si$, 493.12 found 493.1.

Preparation 11: [(S)-1-((R)-3,3-Dimethyl-5-{4-[4-(4,4,5,5-tetramethyl-[1,3,2]dioxaborolan-2-yl)-phenyl]-1H-imidazol-2-yl}-[1,3]azasilolidine-1-carbonyl)-2-methyl-propyl]-carbamic acid methylester

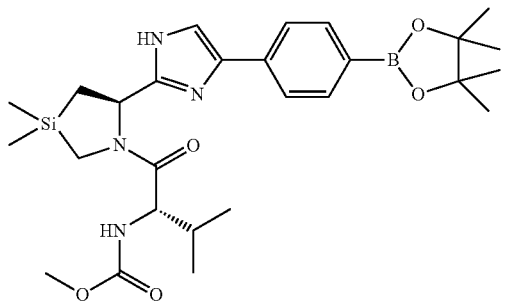

A mixture of ((S)-1-{(R)-5-[4-(4-bromo-phenyl)-1H-imidazol-2-yl]-3,3-dimethyl-[1,3]azasilolidine-1-carbonyl}-2-methyl-propyl)-carbamic acid methyl ester (300 mg, 0.60 mmol, Preparation 10), bis(pinacolato)diboron (190 mg, 0.75 mmol), and potassium acetate (200 mg, 2.04 mmol), Pd(dppf)Cl₂ (30 mg, 0.04 mmol) in dioxane (100 mL) was degassed under vacuum and purged with nitrogen several times. The mixture was stirred at 100° C. overnight, concentrated and the crude product was washed with water and extracted with EtOAc. The organic layer was washed with water and brine, dried over $Na_2SO_4$, concentrated, and purified by silica gel chromatography (1:1 EtOAc:petroleum ether) to give (130 mg, 40% yield) of a mixture of the title intermediate and the corresponding boronic acid as a yellow solid. (m/z): [M+H]⁺ calcd for $C_{27}H_{41}BN_4O_5Si$, 541.29 found 541.3. Boronic acid: (m/z): [M+H]⁺ calcd for $C_{21}H_{31}BN_4O_5Si$, 459.22 found 459.2.

Preparation 12: 7-Bromo-2-((2S,4S)-4-methyl-pyrrolidin-2-yl)-3H-naphtho[1,2-d]imidazole

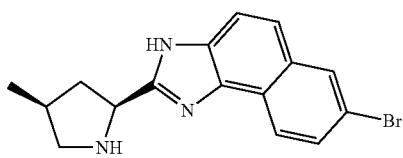 [SMILES: C[C@@H]1CN[C@H](c2nc3c(ccc4cc(Br)ccc43)[nH]2)C1]

(a) (2S,4S)-2-(2-Amino-6-bromo-naphthalen-1-yl-carbamoyl)-4-methyl-pyrrolidine-1-carboxylic acid tert-butyl ester To a solution of 6-bromo-naphthalene-1,2-diamine (2.0 g, 8.5 mmol) in DMF (150 mL) was added (2S,4S)-4-methyl-pyrrolidine-1,2-dicarboxylic acid 1-tert-butyl ester (2.14 g, 10.2 mmol), DIPEA (3.29 g, 25.5 mmol), and HATU (4.84 g, 12.7 mmol). The reaction mixture was stirred at RT overnight and extracted with EtOAc/H₂O (150 mL). The organic layer was dried over Na₂SO₄, filtered, concentrated, and purified by silica gel chromatography (2:1 EtOAc:petroleum ether) to provide the title intermediate (1.6 g)

(b) (2S,4S)-2-(7-Bromo-3H-naphtho[1,2-d]imidazol-2-yl)-4-methyl-pyrrolidine-1-carboxylic acid tert-butyl ester A solution of the product of the previous step (1.6 g, 3.57 mmol) in acetic acid (15 mL) was heated to 60° C. under nitrogen for 1 h, adjusted to pH 8-10 with 1 N NaOH, and extracted with DCM. The organic layer was dried over Na₂SO₄, filtered, and concentrated to give the title intermediate (1.5 g). (m/z): [M+H]⁺ calcd for $C_{21}H_{24}BrN_3O_2$ 430.11, 432.11 found 432.1.

(c) 7-Bromo-2-((2S,4S)-4-methyl-pyrrolidin-2-yl)-3H-naphtho[1,2-d]imidazole

To a solution of the product of the previous step (1.5 g, 3.5 mmol) in DCM (20 mL) was added TFA (2 mL). The mixture was stirred at RT for 5 h, adjusted to pH ~10 with 1 N NaOH (5 mL) and extracted with DCM (3×200 mL). The reaction mixture was dried over Na₂SO₄, filtered, and concentrated to give the title intermediate (1.1 g). (m/z): [M+H]⁺ calcd for $C_{16}H_{16}BrN_3$ 330.05, 332.05 found 330.2, 332.1.

Preparation 13: ((S)-2-Methyl-1-{(2S,4S)-4-methyl-2-[7-(4,4,5,5-tetramethyl-[1,3,2]dioxaborolan-2-yl)-3H-naphtho[1,2-d]imidazol-2-yl]-pyrrolidine-1-carbonyl}-propyl)-carbamic acid methyl ester

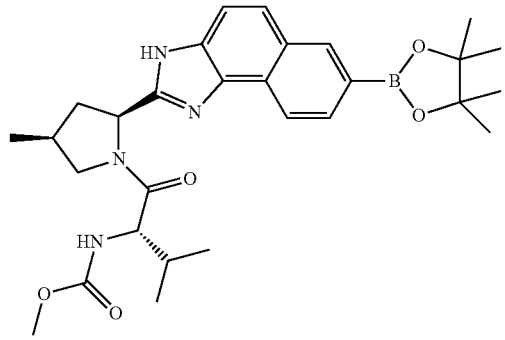

(a) {(S)-1-[(2S,4S)-2-(7-Bromo-3H-naphtho[1,2-d]imidazol-2-yl)-4-methyl-pyrrolidine-1-carbonyl]-2-methyl-propyl}-carbamic acid methyl ester To a solution of 7-bromo-2-((2S,4S)-4-methyl-pyrrolidin-2-yl)-3H-naphtho[1,2-d]imidazole (1.05 g, 3.2 mmol; Preparation 12) in DCM (20 mL) was added (S)-2-Methoxycarbonylamino-3-methyl-butyric acid (672 mg, 3.84 mmol), DIPEA (825 mg, 6.4 mmol), and HATU (1.82 g, 4.8 mmol). The reaction mixture was stirred at RT for 4 h and extracted with DCM (3×250 mL). The organic layer was dried over Na₂SO₄, filtered, concentrated, and purified by silica gel chromatography (1:1 EtOAc:petroleum ether) to provide the title intermediate (1.2 g) (m/z): [M+H]⁺ calcd for $C_{23}H_{27}BrN_4O_3$ 487.13, 489.12 found 489.2.

(b) ((S)-2-Methyl-1-{(2S,4S)-4-methyl-2-[7-(4,4,5,5-tetramethyl-[1,3,2]dioxaborolan-2-yl)-3H-naphtho[1,2-d]imidazol-2-yl]-pyrrolidine-1-carbonyl}-propyl)-carbamic acid methyl ester To a solution of the product of the previous step (1.1 g, 2.2 mmol) in dioxane (20 mL) was added 4,4,5,5,4',4',5',5'-octamethyl-[2,2']bi[[1,3,2]dioxaborolanyl](838 mg, 3.3 mmol), Pd(dppf)Cl₂ (161 mg, 0.22 mmol) and potassium acetate (646 mg, 6.6 mmol) at RT under nitrogen. The reaction mixture was stirred at 90° C. overnight and extracted with EtOAc/H₂O (3×150 mL). The organic layer was dried over Na₂SO₄, filtered, concentrated, and purified by silica gel chromatography (2:1 petroleum ether: EtOAc) to provide the title intermediate (450 mg). (m/z): [M+H]⁺ calcd for $C_{29}H_{39}BN_4O_5$ 535.30 found 535.3. ¹H NMR: (DMSO-d₆, 400 MHz) δ (ppm) 0.64~0.86 (m, 6H), 1.09 (s, 3H), 1.31 (s, 12H), 1.85~1.90 (m, 2H), 2.20~2.38 (m, 1H), 2.51 (s, 1H), 3.31~3.33 (m, 1H), 3.51 (s, 3H), 4.01~4.07 (m, 1H), 4.11~4.16 (m, 1H), 5.09~5.10 (m, 1H), 7.15 (d, J=8.0 Hz, 2H), 7.60~7.79 (m, 3H), 8.23~8.37 (m, 2H), 12.5~13.55 (d, 1H).

Preparation 14:
4-Bromo-3-trifluoromethoxy-benzoic acid methyl ester

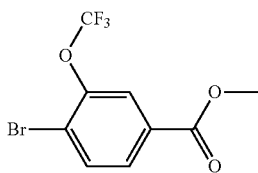 [SMILES: COC(=O)c1ccc(Br)c(OC(F)(F)F)c1]

A mixture of 4-amino-3-(trifluoromethoxy)benzoic acid (504.1 mg, 2.28 mmol), methanol (7.6 mL) and 4.0 M HCl in 1,4-dioxane (5.7 mL) was stirred at RT over the weekend, concentrated, evaporated with EtOAc (3×10 mL), and dried under vacuum to give a brownish solid. The solid was dissolved in a mixture of acetonitrile (23 mL) and water (2.3 mL). Copper(II) bromide (595 mg, 2.66 mmol) and tert-butyl nitrite (0.39 mL, 3.32 mmol) were added to the reaction mixture which was heated at 70° C. for 1.5 h, cooled to RT and diluted with EtOAc (70 mL). The organic layer was washed with saturated sodium bicarbonate (2×15 mL), brine (2×15 mL), dried over sodium sulfate, filtered and concentrated to give a brownish oil, which was purified by silica gel chromatography (24 g silica gel, 0-50% EtOAc/Hexanes). Desired fractions were combined and concentrated to give the title intermediate (281 mg, 41% yield) as a yellowish oil.

Preparation 15: 4'-{2-[(S)-4-Cyclopropyl-1-((S)-2-methoxycarbonylamino-3-methyl-butyryl)-2,5-dihydro-1H-pyrrol-2-yl]-1H-imidazol-4-yl}-2-trifluoromethoxy-biphenyl-4-carboxylic acid

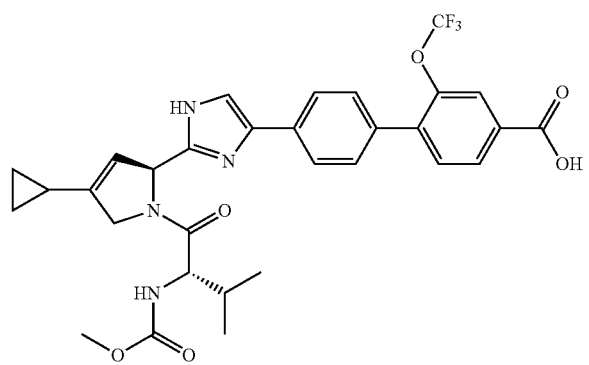 [SMILES: COC(=O)N[C@H](C(=O)N1CC(C2CC2)=C[C@H]1c1nc(-c2ccc(-c3ccc(C(=O)O)cc3OC(F)(F)F)cc2)c[nH]1)C(C)C]

To a mixture of 4-bromo-3-trifluoromethoxy-benzoic acid methyl ester (124 mg, 0.42 mmol), [(S)-1-((S)-4-Cyclopropyl-2-{4-[4-(4,4,5,5-tetramethyl-[1,3,2]dioxaborolan-2-yl)-phenyl]-1H-imidazol-2-yl}-2,5-dihydro-pyrrole-1-carbonyl)-2-methyl-propyl]-carbamic acid methyl ester (200 mg, 0.37 mmol; Preparation 7) and potassium carbonate (233 mg, 1.68 mmol) at RT was added toluene (0.92 mL) followed by water (0.47 mL). The resulting mixture was degassed and flushed with nitrogen and Pd(dppf)Cl₂ (18.5 mg, 0.023 mmol) was added under an atmosphere of nitrogen. The reaction mixture was capped and held at 100° C. overnight, cooled to RT and partitioned between EtOAc (10 mL) and water (2 mL). The organic layer was dried over sodium sulfate, filtered and concentrated to give a brownish oil which was dissolved in a mixture of methanol (3.8 mL) and water (2 mL) and treated with lithium hydroxide monohydrate (95 mg, 2.27 mmol) at 65° C. for 1 hr. The reaction mixture was concentrated, dissolved in 1:1 acetic acid:water (6 mL), filtered and purified by reverse phase HPLC. Desired fractions were combined and freeze dried to give the TFA salt of the title intermediate (140 mg, 51% yield) as a white solid. (m/z): [M+H]⁺ calcd for $C_{31}H_{31}F_3N_4O_6$ 613.22 found 613.6.

Preparation 16: (R)-4-(5-Carboxy-pyridin-2-yl)-3-methyl-piperazine-1-carboxylic acid tert-butyl ester

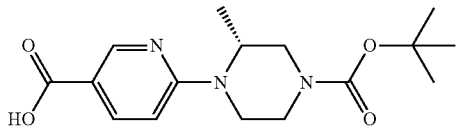 [SMILES: C[C@@H]1CN(C(=O)OC(C)(C)C)CCN1c1ccc(C(=O)O)cn1]

A mixture of 6-fluoronicotinic acid (150 g, 1.063 mol) and (R)-3-methyl-piperazine-1-carboxylic acid tert-butyl ester (234.2 g, 1.169 mol) in tetrahydrofuran (1.75 L) was cooled to −40° C. and then 2 M isopropylmagnesium chloride in tetrahydrofuran (1.196 L, 2.39 mol) was added slowly maintaining the temperature at less than −20° C. The reaction mixture was slowly warmed to RT, stirred at RT for 4 h and then 1 N HCl (1.75 L) and water (1.175 L) were added. The reaction mixture was extracted with ethyl acetate (4 L). The organic phase was evaporated to provide crude solid (534 g). To the crude solid was added acetone (2 L) and water (200 mL). The resulting reaction mixture was heated to 50° C. and then water (2.8 L) was added slowly. Seed crystals from a previous run at smaller scale were added after ~1 L of water. The reaction mixture was cooled to 20° C. over 3 h, stirred at 20° C. overnight and filtered. The solid was washed with 2:3 acetone:water (2×500 mL) and dried under vacuum to provide the title compound (329 g, 96% yield) as an off-white solid. HPLC Method A: Retention time 9.73 min.

Preparation 17: 4-{2-[(2S,4S)-1-((S)-2-methoxycarbonylamino-3-methyl-butyryl)-4-methyl-pyrrolidin-2-yl]-3H-naphth[1,2-d]imidazol-7-yl}-3-trifluoromethoxy-benzoic acid

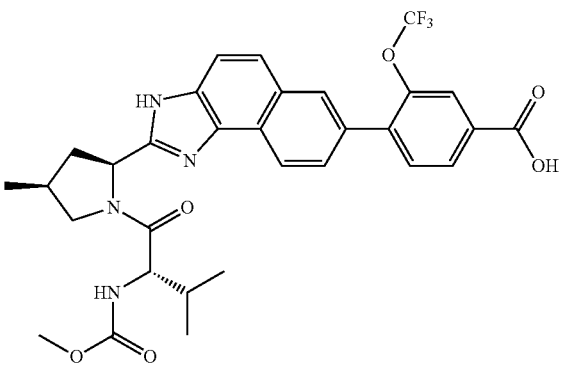 [SMILES: COC(=O)N[C@H](C(=O)N1C[C@@H](C)C[C@H]1c1nc2c(ccc3cc(-c4ccc(C(=O)O)cc4OC(F)(F)F)ccc32)[nH]1)C(C)C]

(a) 4-{2-[(2S,4S)-1-((S)-2-Methoxycarbonylamino-3-methyl-butyryl)-4-methyl-pyrrolidin-2-yl]-3H-naphth[1,2-d]imidazol-7-yl}-3-trifluoromethoxy-benzoic acid methyl ester A solution of ((S)-2-methyl-1-{(2S,4S)-4-methyl-2-[7-(4,4,5,5-tetramethyl-[1,3,2]dioxaborolan-2-yl)-3H-naphtho[1,2-d]imidazol-2-yl]-pyrrolidine-1-carbonyl}-propyl)-carbamic acid methyl ester (250 mg, 0.48 mmol; Preparation 13), 4-bromo-3-trifluoromethoxy-benzoic acid methyl ester (140 mg, 0.47 mmol), and potassium carbonate (323 mg, 2.34 mmol) in toluene (2 mL) and water (0.5 mL) was purged with nitrogen for 5 min, then Pd(dppf)Cl$_2$ (20.5 mg, 0.029 mmol) was added. The reaction mixture was stirred at 100° C. overnight, diluted with ethyl acetate (50 mL), washed with water (2×5 mL). The organic layer was dried over magnesium sulfate, filtered, concentrated, and purified by silica gel chromatography (EtOAc/hexane 20 to 100%) to give the title intermediate (284 mg, 97% yield). (m/z): [M+H]$^+$ calcd for C$_{32}$H$_{32}$F$_3$N$_4$O$_6$ 627.24 found 627.3.

(b) 4-{2-[(2S,4S)-1-((S)-2-methoxycarbonylamino-3-methyl-butyryl)-4-methyl-pyrrolidin-2-yl]-3H-naphth[1,2-d]imidazol-7-yl}-3-trifluoromethoxy-benzoic acid A solution of the product of the previous step in methanol (10 mL) was stirred with lithium hydroxide (112 mg, 2.34 mmol) in water (2 mL) at 65° C. for 2 h, concentrated, dissolved in 1:1 acetic acid:water (5 mL), filtered and purified by reverse phase HPLC to provide the TFA salt of the title intermediate (273 mg, 80% yield). (m/z): [M+H]$^+$ calcd for C$_{31}$H$_{31}$F$_3$N$_4$O$_6$ 613.22 found 613.2.

Preparation 18: (S)-Methoxycarbonylamino-(tetrahydro-pyran-4-yl)-acetic acid

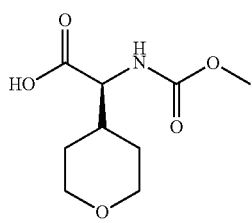

A solution of (S)-amino-(tetrahydro-pyran-4-yl)-acetic acid (1 g, 6.28 mmol) in saturated aqueous sodium bicarbonate solution (12.32 mL, 125.6 mmol) was stirred until all solids were dissolved. Methyl chloroformate (0.97 mL, 12.56 mmol) was added dropwise, the reaction mixture was stirred for 1 h, and IN HCl was added to adjust pH to 1. The reaction mixture was extracted with ethyl acetate (3×15 mL) and the organic extracts were dried over sodium sulfate, filtered, concentrated and dried overnight under vacuum to give the title intermediate (1.36 g, 99% yield) as a white, sticky solid. (m/z): [M+H]$^+$ calcd for C$_9$H$_{15}$NO$_5$ 218.10 found 218.3.

Preparation 19: (S)-5-Methyl-piperidine-1,2-dicarboxylic acid 1-tert-butyl ester

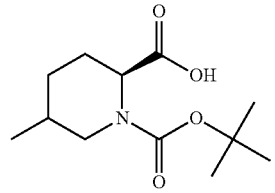 [SMILES: CC1CC[C@@H](C(=O)O)N(C(=O)OC(C)(C)C)C1]

(a) (S)-6-Oxo-piperidine-2-carboxylic acid

A mixture of (S)-2-amino-hexanedioic acid (50 g, 310.25 mmol), acetic acid (100 mL), and water (400 mL) water was refluxed for 3 h. The unchanged starting amino acid was filtered off (24 g) and the filtrate evaporated, dissolved in hot water (50 mL) and then cooled. A crystalline precipitate formed which was filtered to provide the title intermediate (20 g, 45% yield).

(b) (S)-6-Oxo-piperidine-2-carboxylic acid ethyl ester

To a mixture of the product of the previous step (8.4 g, 58.68 mol) in dry ethanol (200 mL) was added thionyl chloride (69.81 g, 586.8 mol) slowly at 0° C. The reaction mixture was stirred at RT overnight and then water was added and the reaction mixture was extracted with EtOAc. The organic layers were washed with sodium bicarbonate and brine, dried over Na$_2$SO$_4$, filtered, and concentrated to provide the title intermediate (6 g). (m/z): [M+H]$^+$ calcd for C$_8$H$_{13}$NO$_3$ 172.09 found 172.1.

(c) (S)-6-Oxo-piperidine-1,2-dicarboxylic acid 1-tert-butyl ester 2-ethyl ester To a mixture of(S)-6-oxo-piperidine-2-carboxylic acid ethyl ester (12 g, 70.10 mmol) in dry ACN (100 mL) was added 4-dimethylaminopyridine (25.69 g, 210.30 mmol) slowly and followed by di-tert-butyl dicarbonate (30.6 g, 140.20 mmol) dropwise at 0° C. The reaction mixture was stirred at RT overnight, and filtered. The organic layer was concentrated and purified by silica gel chromatography (3:1 petroleum ether:EtOAc) to provide the title intermediate (13 g, 68% yield). $^1$H NMR (400 MHz, CDCl$_3$): δ (ppm) 4.70-4.60 (m, 1H), 4.26-4.17 (m, 2H), 2.63-2.53 (m, 1H), 2.51-2.45 (m, 1H), 2.20-2.12 (m, 1H), 2.08-1.96 (m, 1H), 1.80-1.70 (m, 2H), 1.50 (s, 9H), 1.30-1.25 (m, 3H).

(d) (S)-5-Methyl-6-oxo-piperidine-1,2-dicarboxylic acid 1-tert-butyl ester 2-ethyl ester To the product of the previous step (5 g, 18.43 mmol) in dry toluene (100 mL) was added 1 M lithium bis(trimethylsilyl)amide (21 mL) in THF (21 mmol) at −78° C.. After 1 h, methyl trifluoromethane sulfonate (3.63 g, 22.11 mmol) was added dropwise and the reaction mixture was stirred at −78° C. for 2.5 h. Saturated aqueous ammonium chloride was added and allowed to warm to RT. The organic layer was separated and the aqueous layer was extracted with EtOAc. The combined organic layer was washed with water and brine, and dried over $Na_2SO_4$, filtered and concentrated under reduced pressure. The residue was purified by flash chromatography (eluting with 1:3 EtOAc:petroleum ether) to give the title intermediate (3.8 g, 72% yield). (m/z): [M−Boc+H]$^+$ calcd for $C_{14}H_{23}NO_5$ 186.16 found 186.1.

(e) (S)-5-Methyl-piperidine-1,2-dicarboxylic acid 1-tert-butyl ester 2-ethyl ester To a solution of (S)-5-methyl-6-oxo-piperidine-1,2-dicarboxylic acid 1-tert-butyl ester 2-ethyl ester (10 g, 35 mmol) in THF (150 mL) was added borane dimethylsulfide complex (49 mL, 49 mmol). The reaction mixture was stirred at 0° C. for 1 h, and then stirred at 40° C. for 3 h. Methanol was added and the reaction mixture was concentrated, washed with 1 M HCl, and extracted with EtOAc/water to give the oil layer, which was dried, and concentrated. The crude product was purified by silica gel chromatography (20:1 petroleum ether:EtOAc) to provide the title intermediate (2 g, 21% yield). (m/z): [M−100+H]$^+$ calcd for $C_{14}H_{25}NO_4$ 172.18 found 172.2.

(f) (S)-5-Methyl-piperidine-1,2-dicarboxylic acid 1-tert-butyl ester

To a solution of (S)-5-methyl-piperidine-1,2-dicarboxylic acid 1-tert-butyl ester 2-ethyl ester (1.4 g, 5.16 mmol) in methanol (15 mL) and water (5 mL) was added lithium hydroxide monohydrate (650 mg, 15.48 mmol). The reaction mixture was stirred at RT overnight and concentrated to give the residue, which was extracted with EtOAc/water. The aqueous layer was acidified with 1 N HCl, and extracted with EtOAc to give the organic layer, which was dried and concentrated to give the crude product.

Preparation 20: ((S)-1-{(2S,5S)-2-[5-(4-Bromo-phenyl)-1H-imidazol-2-yl]-5-methyl-piperidine-1-carbonyl}-2-methyl-propyl)-carbamic acid methyl ester

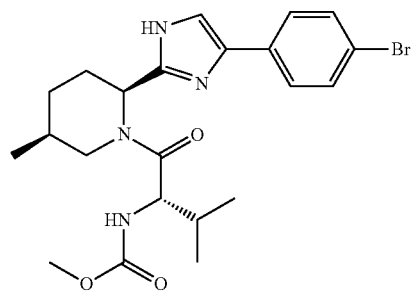 [SMILES: COC(=O)N[C@H](C(=O)N1C[C@@H](C)CC[C@H]1c1nc(-c2ccc(Br)cc2)c[nH]1)C(C)C]

(a) (S)-5-Methyl-piperidine-1,2-dicarboxylic acid 2-[2-(4-bromo-phenyl)-2-oxo-ethyl]ester 1-tert-butyl ester To a mixture of (S)-5-methyl-piperidine-1,2-dicarboxylic acid 1-tert-butyl ester (1.8 g, 7.4 mmol) and 2-bromo-1-(4-bromophenyl)ethanone (2.47 g, 8.88 mmol) in acetonitrile (50 mL) was added DIPEA (2.87 g, 22.19 mmol). The reaction mixture was stirred at RT overnight, concentrated, purified by silica gel chromatography (3:1 petroleum ether:EtOAc) to provide the title intermediate (1.5 g). (m/z): [M+H−Boc]$^+$ calcd for $C_{20}H_{26}BrNO_5$ 340.10, 342.10. found 340.1, 342.1.

(b) (2S,5S)-2-[5-(4-Bromo-phenyl)-1H-imidazol-2-yl]-5-methyl-piperidine-1-carboxylic acid tert-butyl ester A mixture of (S)-5-methyl-piperidine-1,2-dicarboxylic acid 2-[2-(4-bromo-phenyl)-2-oxo-ethyl]ester 1-tert-butyl ester (2.4 g, 5.45 mmol) and ammonium acetate (8.4 g, 109 mmol) in toluene (60 mL) was refluxed overnight. The reaction mixture was extracted with EtOAc/water to give the oil layer, which was dried, concentrated and purified by silica gel chromatography (1:1 petroleum ether:EtOAc) to provide the product (1.3 g) which was purified by supercritical fluid chromatography (SFC) [mobile phase A: supercritical $CO_2$, phase B: ethanol+0.05% $NH_4OH$; A:B 70:30; flow rate 60 mL/min) to provide the title intermediate (0.4 g, 20% yield) and trans isomer (0.26 g). $^1H$ NMR (400 MHz, $(CD_3)_2CO$): δ (ppm) (d, 3H, J=2.4 Hz), 1.44 (s, 9H), 1.50-1.60 (m, 2H), 1.70-1.90 (m, 1H), 1.28 (s, 4H), 2.40-2.70 (m, 2H), 3.70-4.18 (m, 1H), 5.44 (s, 1h), 7.47 (d, J=2 Hz, 2H), 7.53 (m, 1H), 7.77 (d, 2H, J=2 Hz)

(c) (2S,5S)-2-[5-(4-Bromo-phenyl)-1H-imidazol-2-yl]-5-methyl-piperidine

A mixture of the product of the previous step (400 mg, 0.95 mmol) and 4 M HCl in dioxane (10 mL) was stirred at RT for 3 h and concentrated to give the title intermediate (300 mg).

(d) ((S)-1-{(2S,5S)-2-[5-(4-Bromo-phenyl)-1H-imidazol-2-yl]-5-methyl-piperidine-1-carbonyl}-2-methyl-propyl)-carbamic acid methyl ester A mixture of 2S,5S)-2-[5-(4-bromo-phenyl)-1H-imidazol-2-yl]-5-methyl-piperidine (400 mg, 1.25 mmol) and (S)-2-methoxycarbonylamino-3-methyl-butyric acid (219 mg, 1.25 mmol), HATU (475 mg, 1.25 mmol), and DIPEA (485 mg, 3.75 mmol) in DCM (20 mL) was stirred at RT overnight. The reaction mixture was concentrated and purified by thin layer chromatography (1:1 petroleum ether:EtOAc) to provide the title intermediate (550 mg, 92% yield). (m/z): [M+H]$^+$ calcd for $C_{22}H_{28}BrN_4O_3$ 476.13, 478.13, found 478.7.

Preparation 21: [(S)-2-Methyl-1-((2S,5S)-5-methyl-2-{5-[4-(4,4,5,5-tetramethyl-[1,3,2]dioxaborolan-2-yl)-phenyl]-1H-imidazol-2-yl}-piperidine-1-carbonyl)-propyl]-carbamic acid methyl ester

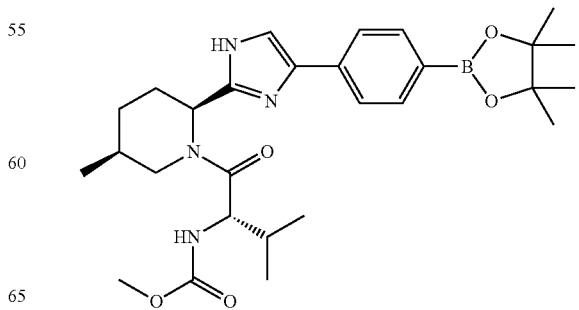

A mixture of ((S)-1-{(2S,5S)-2-[5-(4-bromo-phenyl)-1H-imidazol-2-yl]-5-methyl-piperidine-1-carbonyl}-2-methyl-propyl)-carbamic acid methyl ester (850 mg, 1.78 mmol) and bis(pinacolato)diboron (452 mg, 1.78 mmol), potassium acetate (350 mg, 3.56 mmol), and Pd(dppf)Cl$_2$ (170 mg) in dioxane (20 mL) was stirred at reflux for 3 h. The reaction mixture was concentrated and purified by silica gel chromatography (1:1 petroleum ether:EtOAc) to provide the title intermediate (220 mg, 24% yield). (m/z): [M+H]$^+$ calcd for C$_{28}$H$_{40}$BN$_4$O$_5$ 524.31. found 525. $^1$H NMR (400 MHz, CDCl$_3$: δ (ppm) 0.70-090 (m, 4H), 0.97-1.03 (m, 5H), 1.28 (s, 4H), 1.30-1.60 (m, 2H), 1.80-2.10 (m, 3H), 2.74 (m, 1H), 3.60 (s, 1H), 3.61 (s, 2H), 4.20 (d, 1H, J=8.4 Hz), 4.50 (d, J=12.8 Hz, 1H), 5.53 (s, 1H), 7.45-7.57 (m, 2H), 7.60-7.78 (m, 3H).

Preparation 22: (1R,3S,4S)-3-{5-[4-(4,4,5,5-Tetramethyl-[1,3,2]dioxaborolan-2-yl)-phenyl]-1H-imidazol-2-yl}-2-aza-bicyclo[2.2.1]heptane-2-carboxylic acid tert-butyl ester

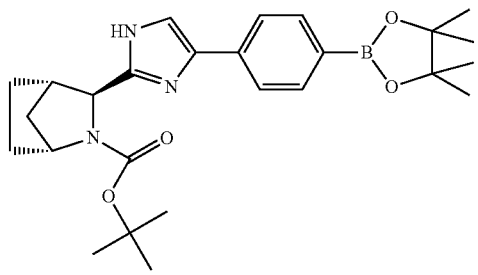 [SMILES: CC(C)(C)OC(=O)N1[C@@H]2CC[C@@H](C2)[C@H]1c1nc(-c2ccc(B3OC(C)(C)C(C)(C)O3)cc2)c[nH]1]

(a) (1S,3S,4R)-2-((R)-1-Phenyl-ethyl)-2-aza-bicyclo[2.2.1]hept-5-ene-3-carboxylic acid ethyl ester To a solution of (R)-1-phenyl-ethylamine (59 g, 0.49 mmol) dissolved in toluene (500 mL) was added sodium sulfate (173 g, 1.22 mmol) followed by oxo-acetic acid ethyl ester (134 g, 0.49 mmol, 50% in toluene) dropwise. The reaction mixture was stirred at RT for 1 h. The solid was filtered and the filtrate was concentrated under vacuum to provide ((R)-1-phenyl-ethylimino)-acetic acid ethyl ester, which was dissolved in DMF (300 mL) at RT. TFA (56 g, 0.49 mmol) was added dropwise at RT, followed after 10 min by cyclopenta-1,3-diene (65 g, 0.98 mmol) and water (0.25 ml). The mixture was stirred at RT overnight, concentrated under vacuum and the residue was poured into a 10% aqueous solution of NaHCO$_3$ (500 mL). The solution was adjusted to pH 8 with solid Na$_2$CO$_3$, and extracted with EtOAc (3×80 mL). The combined organic layers were purified by silica gel chromatography (30:1-15:1 petroleum ether:EtOAc) to provide the title intermediate (35 g, 26% yield), as a colorless oil. (m/z): [M+H]$^+$ calcd for C$_{17}$H$_{21}$NO$_2$ 272.16 found 272.2.

(b) (1R,3S,4S)-2-((R)-1-Phenyl-ethyl)-2-aza-bicyclo[2.2.1]heptane-3-carboxylic acid ethyl ester A mixture of the product of the previous step (6 g, 22.11 mmol) and Pd/C (0.6 g) in EtOH (300 mL) was stirred at RT under H$_2$ (30 psi) overnight. The mixture was filtered and 1 mL of conc. HCl was added to the filtrate. The solution was concentrated under vacuum to afford the the title intermediate (6 g, 100%), as white solid. (m/z): [M+H]$^+$ calcd for C$_{17}$H$_{23}$NO$_2$ 274.17 found 274.2.

(c) (1R,3S,4S)-2-Aza-bicyclo[2.2.1]heptane-2,3-dicarboxylic acid 2-tert-butyl ester A mixture of the product of the previous step (1 g, 3.66 mmol) and Pd(OH)$_2$/C (100 mg, 1% H$_2$O) in methanol (50 mL) was stirred at 40° C. under hydrogen (50 psi) overnight, filtered and concentrated under vacuum to provide (1R,3S,4S)-2-aza-bicyclo[2.2.1]heptane-3-carboxylic acid ethyl ester (0.6 g, 100%), as pale yellow solid, which was mixed with concentrated aqueous HCl (10 mL). The reaction mixture was concentrated under vacuum to provide (1R,3 S,4S)-2-aza-bicyclo[2.2.1]heptane-3-carboxylic acid (0.5 g) as a pale yellow solid.

A mixture of the pale yellow solid (0.5 g), NaOH (0.44 g, 11.01 mmol), THF (20 mL) and water (4 mL) was stirred at RT for 0.5 h and then, di-tert-butyl dicarbonate (0.8 g, 3.67 mmol) was added dropwise. The reaction mixture was stirred at RT overnight. THF was removed under reduced pressure and water (20 mL) was added. The solution was washed with EtOAc (2×10 mL). The aqueous layer was adjusted to pH 5 with 3 M HCl and freeze dried. The solid was dissolved in 1:8 methanol:DCM (30 mL) and filtered and the filtrate was concentrated under vacuum to provide the title intermediate (220 mg), as white solid. (m/z): [M+H−tBu]$^+$ calcd for C$_{12}$H$_{19}$NO$_4$ 186.07 found 186.1.

(d) (1R,3S,4S)-2-Aza-bicyclo[2.2.1]heptane-2,3-dicarboxylic acid 3-[2-(4-bromo-phenyl)-2-oxo-ethyl]ester 2-tert-butyl ester A mixture of compound (1R,3S,4S)-2-aza-bicyclo[2.2.1]heptane-2,3-dicarboxylic acid 2-tert-butyl ester (3 g, 12.43 mmol), 2-bromo-1-(4-bromophenyl)ethanone (3.80 g, 12.43 mmol) and cesium carbonate (12.15 g, 37.30 mmol) in ACN (500 mL) was stirred at RT overnight. The reaction mixture was filtered and the solid was washed with EtOAc (3×50 mL). The filtrate was concentrated under vacuum and purified by silica gel chromatography (20:1-5:1 petroleum ether: EtOAc) to provide the title intermediate (3 g, 45% yield) as a white solid. (m/z): [M+H−tBu]$^+$ calcd for C$_{20}$H$_{24}$BrNO$_5$ 382.02, 384.02 found 381.9.

(e) (1R,3S,4S)-3-[4-(4-Bromo-phenyl)-1H-imidazol-2-yl]-2-aza-bicyclo[2.2.1]heptane-2-carboxylic acid tert-butyl ester A mixture of the product of the previous step (3 g, 5.57 mmol) and ammonium acetate (4.29 g, 55.73 mmol) in toluene (500 mL) was stirred at 100° C. overnight, concentrated under vacuum, dissolved in DCM (500 mL) and washed with water (3×50 mL). The organic layer was dried with Na$_2$SO$_4$, filtered, concentrated under vacuum, and purified by silica gel chromatography (20:1-5:1 petroleum ether: EtOAc) to provide the title intermediate (1.6 g, 69% yield) as a white solid. (m/z): [M+H]$^+$ calcd for C$_{20}$H$_{24}$BrN$_3$O$_2$ 418.11, 420.11 found 418.1.

(f) (1R,3S,4S)-3-{5-[4-(4,4,5,5-Tetramethyl-[1,3,2]dioxaborolan-2-yl)-phenyl]-1H-imidazol-2-yl}-2-aza-bicyclo[2.2.1]heptane-2-carboxylic acid tert-butyl ester A mixture of the product of the previous step (1.50 g, 3.59 mmol), bis(pinacolato)diboron (1.00 g, 3.94 mmol), Pd(dppf)Cl$_2$ (150 mg, 10.76 mmol) and potassium acetate (1.06 g, 10.76 mmol) in 1,4-dioxane (200 mL) was stirred at 80° C. for 3 h under nitrogen, concentrated under vacuum, and purified by silica gel chromatography (10:1-5:1 petroleum ether: EtOAc) to provide the title intermediate (500 mg, 44% yield) as a white solid. (m/z): [M+H]+ calcd for $C_{26}H_{36}BN_3O_4$ 466.28 found 466.4 $^1$H NMR (400 MHz, $CH_3OD$): δ (ppm) 1.18 (s, 6H), 1.23 (s, 2H), 1.25 (s, 4H), 1.34 (s, 9H), 1.36-1.41 (m, 1H), 1.58-1.65 (m, 1H), 1.65-1.78 (m, 2H), 1.79-1.97 (m, 2H), 2.55-2.70 (m, 1H), 4.22-4.35 (m, 1H), 4.45 (d, J=12.57 Hz, 1H), 7.34 (d, J=12.35 Hz, 1H), 7.56-7.84 (m, 4H).

Preparation 23: [(S)-2-{(2S,4S)-4-Methyl-2-[7-(4,4,5,5-tetramethyl-[1,3,2]dioxaborolan-2-yl)-3H-naphtho[1,2-d]imidazol-2-yl]-pyrrolidin-1-yl}-2-oxo-1-(tetrahydro-pyran-4-yl)-ethyl]-carbamic acid methyl ester

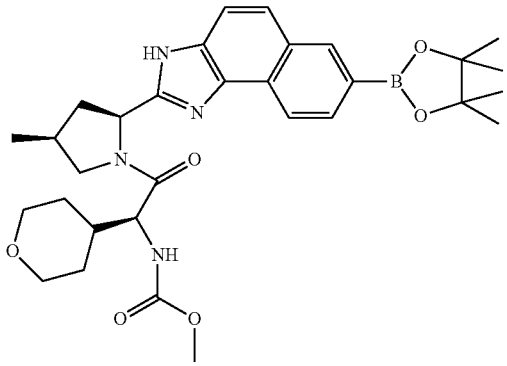

(a) 7-Bromo-2-((2S,4S)-4-methyl-pyrrolidin-2-yl)-3Hnaphth[1,2-d]imidazole

A mixture of (2S,4S)-2-(7-bromo-3H-naphtho[1,2-d]imidazol-2-yl)-4-methyl-pyrrolidine-1-carboxylic acid tert-butyl ester (300 mg, 0.70 mmol) and 4 M HCl in 1,4-dioxane (2 mL) was heated at 50° C. for 1 h, concentrated, dissolved in EtOAc, and evaporated with EtOAc (2×) to provide the HCl salt of the title intermediate as a yellow solid. (m/z): [M+H]+ calcd for $C_{16}H_{16}BrN_3$ 330.05, 332.05 found 331.9.

(b) [(S)-2-[(2S,4S)-2-(7-Bromo-3H-naphth[1,2-d]imidazol-2-yl)-4-methyl-pyrrolidin-1-yl]-2-oxo-1-(tetrahydropyran-4-yl)-ethyl]-carbamic acid methyl ester The yellow solid from the previous step was dissolved in DMF (5 mL) and DIPEA (0.61 mL, 3.5 mmol) was added. A solution of (S)-methoxycarbonylamino-(tetrahydro-pyran-4-yl)-acetic acid (189 mg, 0.87 mmol) and HATU (331 mg, 0.871 mmol) dissolved in DMF (5 mL) was added. The reaction mixture stirred at RT for 1 h, dissolved in EtOAc (100 mL) and washed with water (300 mL). The aqueous layer was extracted with EtOAc (100 mL). The combined organic layer was washed with brine, dried over sodium sulfate, filtered, concentrated, and purified by silica gel chromatography (0-100% EtOAc:hexanes) to produce the title intermediate (344 mg, 90% yield) as a light colored solid. (m/z): [M+H]+ calcd for $C_{25}H_{29}BrN_4O_4$ 529.14, 531.14 found 529.1.

(c) [(S)-2-{(2S,4S)-4-Methyl-2-[7-(4,4,5,5-tetramethyl-[1,3,2]dioxaborolan-2-yl)-3H-naphtho[1,2-d]imidazol-2-yl]-pyrrolidin-1-yl}-2-oxo-1-(tetrahydropyran-4-yl)-ethyl]-carbamic acid methyl ester The product of the previous step (344 mg, 0.65 mmol), bis(pinacolato)diboron (250 mg, 0.97 mmol), and potassium acetate (96 mg, 0.97 mmol) were mixed with 1,4-dioxane (2.2 mL). The resulting suspension was sparged under nitrogen before $Pd(dppf)Cl_2 \cdot CH_2Cl_2$ (26 mg, 0.032 mmol) was added and the reaction mixture was heated at 100° C. overnight, cooled to RT and filtered through a stacked pad of silica gel atop Celite®. The pad was washed with EtOAc (180 mL). The filtrate was concentrated to give a black oil, which was loaded on a 12 g gold silica gel disposable column with DCM (eluted with 0-100% EtOAc:hexanes). Desired fractions were combined and concentrated to give the title intermediate (256 mg) as a yellowish foam. (m/z): [M+H]+ calcd for corresponding boronic acid $C_{25}H_{31}BN_4O_6$ 495.231 found 495.0.

Preparation 24: (1R,3S,6S)-2-Aza-bicyclo[4.1.0]heptane-2,3-dicarboxylic acid 2-tert-butyl ester

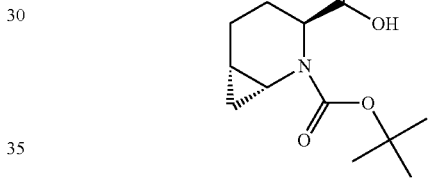

(b) (S)-6-Hydroxymethyl-piperidin-2-one

To a solution of (S)-6-oxopiperidine-2-carboxylic acid (17 g, 120 mmol) in methanol (200 mL) was added thionyl chloride (87 mL, 1.2 mol) and the reaction mixture was stirred at RT overnight, concentrated, combined with the product of a similar preparation, washed with saturated aqueous $NaHCO_3$, and extracted with EtOAc (4×200 mL). The organic layers were combined, dried over sodium sulfate and evaporated to provide crude (S)-methyl 6-oxopiperidine-2-carboxylate (36.5 g).

To a solution of the product of the previous step (18.5 g, 117.7 mmol) in ethanol (200 mL) was added sodium borohydride (6.7 g, 176.6 mmol) over 30 min at RT and the reaction mixture was stirred at RT overnight. Acetic acid (17 mL) was added; the solution was concentrated and the residue was combined with the product of a similar preparation and dissolved in DCM, dried over potassium bicarbonate, filtered, and the filtrate was evaporated to give the title intermediate (30 g).

(c) (S)-6-((tert-Butyldiphenylsilyloxy)methyl)piperidin-2-one

To a mixture of the product of the previous step (30 g, 232.3 mmol) in DCM (300 mL) was added DIPEA (90 g, 696.6 mmol), 4-dimethylaminopyridine (2.84 g, 23.2 mmol), and tert-butyldiphenylsilyl chloride (95.7 g, 349.3 mmol) at 0° C. The reaction mixture was stirred at RT overnight and then water was added and the reaction mixture was extracted with EtOAc (4×200 mL). The organic layers were combined, dried over Na$_2$SO$_4$, evaporated, and the residue was purified by silica gel chromatography (eluting with 50-100% EtOAc in petroleum ether) to provide the title intermediate (5 g).

(d) (S)-tert-Butyl 2-((tert-butyldiphenylsilyloxy)methyl)-6-oxopiperidine-1-carboxylate The product of the previous step (24.3 g, 66.4 mmol) was dissolved in Boc$_2$O (72.4 g, 332 mmol) and 4-dimethylaminopyridine (810 mg, 66.4 mmol) was added. The reaction mixture was stirred and refluxed overnight, concentrated and purified by silica gel chromatography (eluting with 0-50% EtOAc in petroleum ether) to provide the title intermediate (28 g).

(g) (2S)-tert-Butyl 2-((tert-butyldiphenylsilyloxy)methyl)-6-hydroxypiperidine-1-carboxylate To a solution of the product of the previous step (14 g, 30 mmol) in toluene cooled to −50° C. was added 1 M lithium triethylborohydride (36 mL) in THF (36 mmol) dropwise over 15 min and the reaction mixture was stirred for 2 h at −50 to −45° C. Saturated aqueous sodium bicarbonate was added and the reaction mixture was warmed to 0° C. Hydrogen peroxide (1 mL) was added; the reaction mixture was stirred for 20 min; layers were separated and the aqueous layer was extracted with EtOAc (2×50 mL). The combined organic layer was washed with water and brine, dried over Na$_2$SO$_4$, filtered and concentrated under reduced pressure. The residue was purified by silica gel chromatography (eluting with 0-20% EtOAc in petroleum ether) to give the title intermediate (10 g). (m/z): [M−100+H]$^+$ calcd for C$_{14}$H$_{23}$NO$_5$ 186.16 found 186.1.

(h) ((2S)-tert-Butyl 2-((tert-butyldiphenylsilyloxy)methyl)-6-methoxypiperidine-1-carboxylate To an ice cold solution of (2S)-tert-butyl 2-((tert-butyldiphenylsilyloxy)methyl)-6-hydroxypiperidine-1-carboxylate (2 g, 4.3 mmol) in methanol (20 mL) was added pyridinium p-toluenesulfonate (108 mg, 0.43 mmol). The reaction mixture was warmed to RT and stirred overnight. Triethylamine (87 mg, 0.86 mmol) was added, the reaction mixture was concentrated under reduced pressure, and the residue was purified by silica gel chromatography (eluting with 0-15% EtOAc in petroleum ether), and combined with the product of three similar runs to provide the title intermediate (3.5 g).

(i) (S)-tert-Butyl 2-((tert-butyldiphenylsilyloxy)methyl)-3,4-dihydropyridine-1(2H)-carboxylate A mixture of ((2S)-tert-butyl 2-((tert-butyldiphenylsilyloxy)methyl)-6-methoxypiperidine-1-carboxylate (9 g, 18.6 mmol) and ammonium chloride (150 mg, 2.8 mmol) was heated at 150° C. under reduced pressure (50 mbar) for 2 h, cooled to RT, and purified by silica gel chromatography (eluting with 0-10% EtOAc in petroleum ether) to provide the title intermediate (7.2 g).

(j) (1R,3S,6S)-tert-Butyl 3-((tert-butyldiphenylsilyloxy)methyl)-2-azabicyclo[4.1.0]heptane-2-carboxylate To an ice cold solution of (S)-tert-butyl 2-((tert-butyldiphenylsilyloxy)methyl)-3,4-dihydropyridine-1(2H)-carboxylate (3.6 g, 8.0 mmol) in DCM (40 mL) was added a 1 M solution of diethylzinc (9.0 mL) followed by diiodomethane (3.2 g, 12.0 mmol) over 15 min. The reaction mixture was stirred for 30 min at 0° C., warmed to RT and stirred for 3 h. The pH of the reaction mixture was adjusted to pH 8 with saturated aqueous sodium bicarbonate. The layers were separated and the aqueous layer was extracted with DCM. The combined organic layers were washed with brine, dried over Na$_2$SO$_4$, concentrated under reduced pressure, purified by silica gel chromatography (eluting with 0-15% EtOAc in petroleum ether) and combined with the product of a similar run to provide the title intermediate (4.5 g) as a colorless gummy liquid.

(k) (1R,3S,6S)-tert-Butyl 3-(hydroxymethyl)-2-azabicyclo[4.1.0]heptane-2-carboxylate To an ice cold solution of the product of the previous step (4.5 g, 9.7 mmol) in dry THF (50 mL) was added tetra-n-butylammonium fluoride (4.0 g, 19.4 mmol). The reaction solution was warmed to RT, stirred for 12 h, and concentrated under reduced pressure. The residue was dissolved in DCM (50 mL) and washed with water (3×50 mL). The organic layer was washed with brine, dried over Na$_2$SO$_4$, evaporated, and purified by silica gel chromatography (eluting with 0-10% methanol in DCM) to give the title intermediate (2.0 g).

(l) (1R,3S,6S)-2-Aza-bicyclo[4.1.0]heptane-2,3-dicarboxylic acid 2-tert-butyl ester To a solution of sodium periodate (15.5 g, 72.6 mmol) in water (80 mL) was added a solution of (1R,3S,6S)-tert-butyl 3-(hydroxymethyl)-2-azabicyclo[4.1.0]heptane-2-carboxylate (5.5 g, 24.2 mmol) in ACN (60 mL) and carbon tetrachloride (60 mL). Ruthenium (III)chloride (246 mg, 1.21 mmol) was added immediately and the reaction mixture was stirred vigorously for 75 min at RT, diluted with water (80 mL), filtered, and extracted with DCM (3×100 mL). The combined organic phase was washed with brine, dried over Na$_2$SO$_4$, and concentrated under vacuum to provide crude product (4.75 g) as a light charcoal-color solid. The crude product was dissolved in EtOAc (20 mL) with heating and allowed to stand at RT with seeding. After about 15 min, rapid crystal formation was observed. About 1 h later, hexane (10 mL) was added and the mixture was refrigerated overnight, filtered, washed with 2:1 ice-water-cooled hexanes:EtOAc (50 mL) and dried under high vacuum to provide the title intermediate (1.9 g) ([a]$_D$=−135.2) The mother liquid was re-crystallized to provide additional product (300 mg) ([a]$_D$=−142.6). $^1$H NMR: (DMSO-d$_6$, 400 MHz) δ (ppm) 4.1 (m, 1H), 2.60 (m, 1H), 1.70 (m, 1H), 1.30 (m, 3H), 1.17 (m, 9H), 0.96 (m, 1H), 0.50 (m, 1H), 0.0 (m, 1H)

Example 1

[(S)-1-((S)-2-{4-[5'-Chloro-4'-({6-[(R)-4-(2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-4-methyl-2,5-dihydro-pyrrole-1-carbonyl)-2-methyl-propyl]-carbamic acid methyl ester

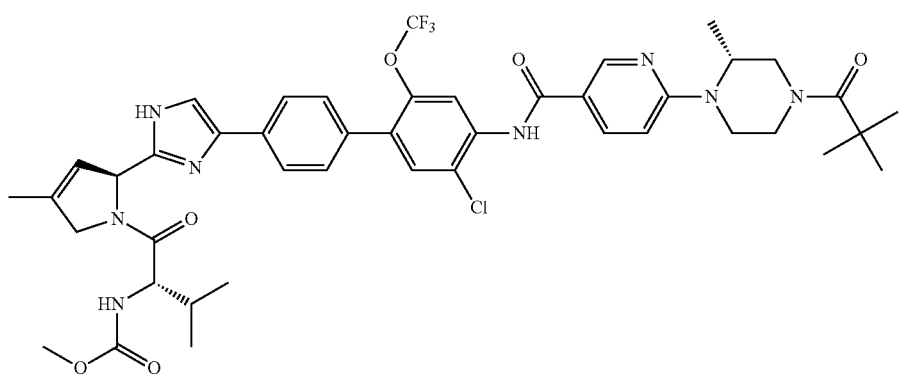 [SMILES: COC(=O)N[C@H](C(=O)N1CC(C)=C[C@H]1c1nc(-c2ccc(-c3cc(Cl)c(NC(=O)c4ccc(N5CCN(C(=O)C(C)(C)C)C[C@H]5C)nc4)cc3OC(F)(F)F)cc2)c[nH]1)C(C)C]

(a) (R)-4-[5-(5-Chloro-2-trifluoromethoxy-4'-{2-[(S)-1-((S)-2-methoxycarbonylamino-3-methyl-butyryl)-4-methyl-2,5-dihydro-1H-pyrrol-2-yl]-1H-imidazol-4-yl}-biphenyl-4-ylcarbamoyl)-pyridin-2-yl]-3-methyl-piperazine-1-carboxylic acid tert-butyl ester To a solution of [(S)-2-Methyl-1-((S)-4-methyl-2-{4-[4-(4,4,5,5-tetramethyl-[1,3,2]dioxaborolan-2-yl)-phenyl]-1H-imidazol-2-yl}-2,5-dihydro-pyrrole-1-carbonyl)-propyl]-carbamic acid methyl ester (100 mg, 0.20 mmol, Preparation 4) and (R)-4-[5-(4-bromo-2-chloro-5-trifluoromethoxy-phenylcarbamoyl)-pyridin-2-yl]-3-methyl-piperazine-1-carboxylic acid tert-butyl ester (110 mg, 0.19 mmol) dissolved in toluene (1.18 mL) and water (0.43 mL) was added potassium carbonate (127 mg, 0.92 mmol). The reaction mixture was sparged under nitrogen for 15 min and Pd(dppf)Cl$_2$ CH$_2$Cl$_2$ (13.55 mg, 0.017 mmol) was added and the reaction mixture was sparged with nitrogen and heated to 90° C. overnight, cooled to RT, diluted with EtOAc and washed with water and brine to produce a dark colored solid, which was purified by silica gel chromatography (12 g silica, EtOAc/hexanes 40 to 100%) to produce the title intermediate (51 mg, 31% yield) as a yellowish colored solid. (m/z): [M+H]$^+$ calcd for C$_{44}$H$_{50}$ClF$_3$N$_8$O$_7$ 895.34 found 895.3.

(b) ((S)-1-{(S)-2-[4-(5'-Chloro-4'-{[6-((R)-2-methyl-piperazin-1-yl)-pyridine-3-carbonyl]-amino}-2'-trifluoromethoxy-biphenyl-4-yl)-1H-imidazol-2-yl]-4-methyl-2,5-dihydro-pyrrole-1-carbonyl}-2-methyl-propyl)-carbamic acid methyl ester The product of the previous step was treated with 4 M HCl in 1,4-dioxane (0.92 mL) and HCl (0.28 mL) and the reaction mixture was stirred at RT for 1 h, concentrated and evaporated with ethyl acetate (2×) to produce the tri-HCl salt of the title intermediate (56 mg, 34% yield). (m/z): [M+H]$^+$ calcd for C$_{39}$H$_{42}$ClF$_3$N$_8$O$_5$ 795.29 found 795.3.

(c) [(S)-1-((S)-2-{4-[5'-Chloro-4'-({6-[(R)-4-(2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-4-methyl-2,5-dihydro-pyrrole-1-carbonyl)-2-methyl-propyl]-carbamic acid methyl ester The product of the previous step (10 mg, 0.011 mmol) was dissolved in DMA (1 mL) and then DIPEA (9.63 µL, 0.055 mmol) was added followed by 2,2-dimethylpropionyl chloride (1.33 mg, 0.011 mmol) and the reaction mixture was stirred at RT overnight, concentrated by rotary evaporation, dissolved in 1:1 acetic acid:water (1.5 mL) and purified by reverse phase HPLC to provide the di-TFA salt of the title compound (7 mg, 60% yield). (m/z): [M+H]$^+$ calcd for C$_{44}$H$_{50}$ClF$_3$N$_8$O$_6$ 879.35 found 879.8.

Example 2

((S)-1-{(S)-2-[4-(5'-Chloro-4'-{[6-((R)-4-(S)-2,2-dimethylcyclopropanecarbonyl-2-methyl-piperazin-1-yl)-pyridine-3-carbonyl]-amino}-2'-trifluoromethoxy-biphenyl-4-yl)-1H-imidazol-2-yl]-4-methyl-2,5-dihydro-pyrrole-1-carbonyl}-2-methyl-propyl)-carbamic acid methyl ester

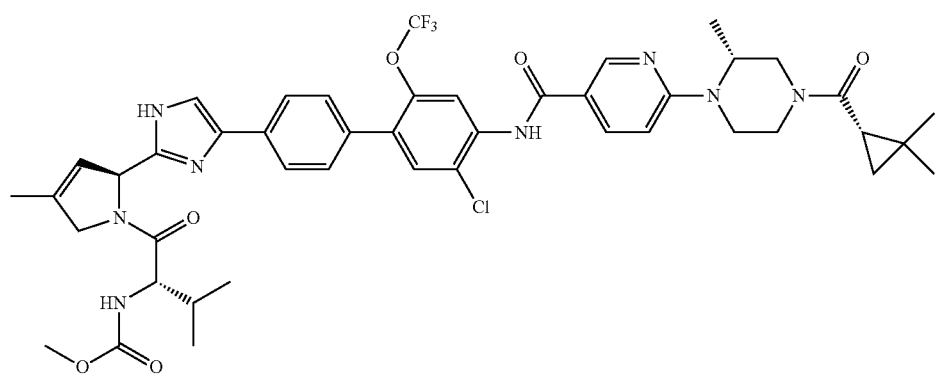

To a solution of 0.5 M of (S)-(+)-2,2-dimethylcyclopropane carboxylic acid in DMA (26.5 µL, 0.013 mmol) in DMA (1 mL) was added HATU (5.04 mg, 0.013 mmol). The reaction mixture was stirred at RT for 20 min and the product of Example 1 step (b) (10 mg, 0.011 mmol) was then added followed by DIPEA (9.63 µL, 0.055 mmol) and the reaction mixture was stirred at RT overnight, concentrated by rotary evaporation, dissolved in 1:1 acetic acid:water (1.5 mL) and purified by reverse phase HPLC to provide the di-TFA salt of the title compound (7 mg, 55% yield). (m/z): [M+H]+ calcd for $C_{45}H_{50}ClF_3N_8O_6$ 891.35 found 891.8.

Following the procedures of Examples 1 and 2, the intermediate of Preparation 7 was used to prepare the compounds of Examples 3 and 4.

Example 3

[(S)-1-((S)-2-{4-[5'-Chloro-4'-({6-[(R)-4-(2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-4-cyclopropyl-2,5-dihydro-pyrrole-1-carbonyl)-2-methyl-propyl]-carbamic acid methyl ester

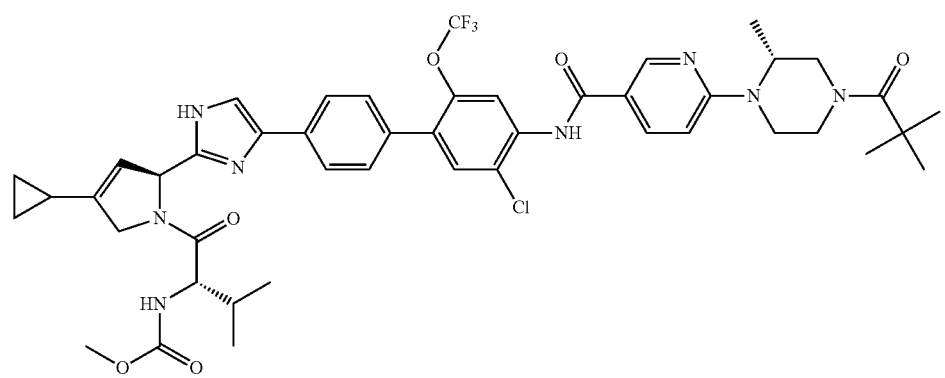 [SMILES: COC(=O)N[C@H](C(=O)N1CC(C2CC2)=C[C@H]1c1nc(-c2ccc(-c3cc(Cl)c(NC(=O)c4ccc(N5CCN(C(=O)C(C)(C)C)C[C@H]5C)nc4)cc3OC(F)(F)F)cc2)c[nH]1)C(C)C]

(0.011 mmol scale, 7 mg, 59% yield) (m/z): [M+H]calcd for $C_{46}H_{52}ClF_3N_8O_6$ 905.37 found 905.8.

Example 4

((S)-1-{(S)-2-[4-(5'-Chloro-4'-{[6-((R)-4-(S)-2,2-dimethylcyclopropanecarbonyl-2-methyl-piperazin-1-yl)-pyridine-3-carbonyl]-amino}-2'-trifluoromethoxy-biphenyl-4-yl)-1H-imidazol-2-yl]-4-cyclopropyl-2,5-dihydro-pyrrole-1-carbonyl}-2-methyl-propyl)-carbamic acid methyl ester (a) (R)-4-[5-(5-Chloro-4'-{2-[(R)-1-((S)-2-methoxy-carbonylamino-3-methyl-butyryl)-3,3-dimethyl-[1,3]azasilolidin-5-yl]-1H-imidazol-4-yl}-2-trifluoromethoxy-biphenyl-4-ylcarbamoyl)-pyridin-2-yl]-3-methyl-piperazine-1-carboxylic acid tert-butyl ester To a solution of [[(5)-1-((R)-3,3-dimethyl-5-{4-[4-(4,4,5,5-tetramethyl-[1,3,2]dioxaborolan-2-yl)-phenyl]-1H-imidazol-2-yl}-[1,3]azasilolidine-1-carbonyl)-2-methyl-propyl]-carbamic acid methylester (51.6 mg, 0.096 mmol; Preparation 11) and (R)-4-[5-(4-bromo-2-chloro-5-trifluoromethoxy-phenylcarbamoyl)-pyridin-2-yl]-3-methyl-pip-

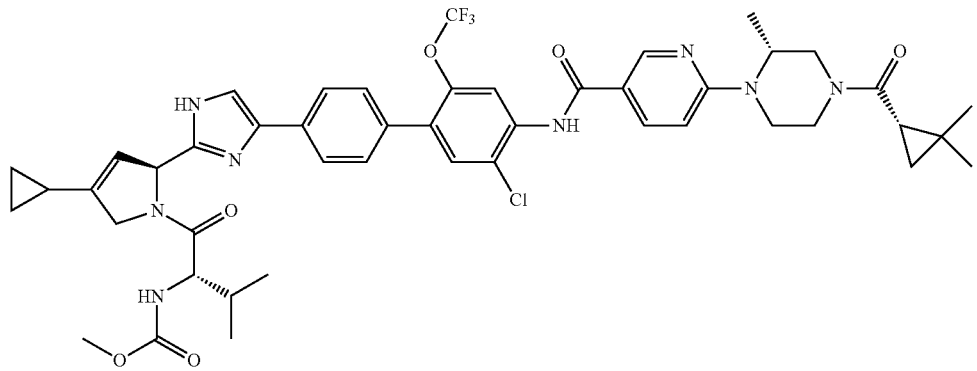 [SMILES: COC(=O)N[C@H](C(=O)N1CC(C2CC2)=C[C@H]1c1nc(-c2ccc(-c3cc(Cl)c(NC(=O)c4ccc(N5CCN(C(=O)[C@H]6CC6(C)C)C[C@H]5C)nc4)cc3OC(F)(F)F)cc2)c[nH]1)C(C)C]

erazine-1-carboxylic acid tert-butyl ester (56.7 mg, 0.096 mmol) dissolved in toluene (0.61 mL) and water (0.24 mL) was added potassium carbonate (66.0 mg, 0.48 mmol). The reaction mixture was sparged under nitrogen for 15 min and Pd(dppf)Cl$_2$CH$_2$Cl$_2$ (7.02 mg, 0.009 mmol) was added. The reaction mixture was sparged with nitrogen and heated to 90° C. overnight, cooled to RT, diluted with EtOAc, and washed with water and brine to produce a dark colored oil. The residue was purified by silica gel chromatography (12 g silica, 0% to 100% EtOAc/hexane) to produce the title intermediate as a yellowish solid (23 mg; 26% yield) (m/z): [M+H]$^+$ calcd for $C_{44}H_{54}ClF_3N_8O_7Si$, 927.35 found 927.4.

(0.011 mmol scale, 7 mg, 59% yield) (m/z): [M+H]$^+$ calcd for $C_{47}H_{52}ClF_3N_8O_6$ 917.37 found 917.8.

Example 5

((S)-1-{(R)-5-[4-(5'-Chloro-4'-{[6-((R)-4-(S)-2,2-dimethylcyclopropanecarbonyl-2-methyl-piperazin-1-yl)-pyridine-3-carbonyl]-amino}-2'-trifluoromethoxy-biphenyl-4-yl)-1H-imidazol-2-yl]-3,3-dimethyl-[1,3]azasilolidine-1-carbonyl}-2-methyl-propyl)-carbamic acid methyl ester

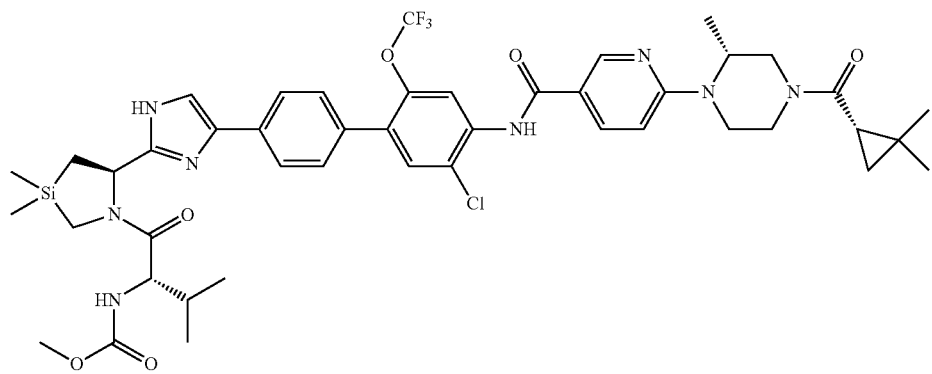

(b) ((S)-1-{(R)-5-[4-(5'-Chloro-4'-{[6-((R)-2-methyl-piperazin-1-yl)-pyridine-3-carbonyl]-amino}-2'-trifluoromethoxy-biphenyl-4-yl)-1H-imidazol-2-yl]-3,3-dimethyl-[1,3]azasilolidine-1-carbonyl}-2-methyl-propyl)-carbamic acid methyl ester The product of the previous step was treated with 4 M HCl in 1,4-dioxane (0.47 mL, 1.91 mmol) and HCl (0.17 mL) and stirred at RT for 1 h, concentrated, and evaporated with ethyl acetate (2×) to produce the tri-HCl salt of the title intermediate. (m/z): [M+H]$^+$ calcd for $C_{39}H_{46}ClF_3N_8O_5Si$, 827.30 found 827.3.

(c) ((S)-1-{(R)-5-[4-(5'-Chloro-4'-{[6-((R)-4-(S)-2,2-dimethylcyclopropanecarbonyl-2-methyl-piperazin-1-yl)-pyridine-3-carbonyl]-amino}-2'-trifluoromethoxy-biphenyl-4-yl)-1H-imidazol-2-yl]-3,3-dimethyl-[1,3]azasilolidine-1-carbonyl}-2-methyl-propyl)-carbamic acid methyl ester To a solution of 0.5 M of (S)-(+)-2,2-dimethylcyclopropane carboxylic acid in DMA (30.7 μL, 0.015 mmol) dissolved in DMA (1 mL) was added HATU (5.84 mg, 0.015 mmol). The reaction mixture was stirred at RT for 20 min and then the product of the previous step (12 mg, 0.013 mmol) was added followed by DIPEA (11.2 μL, 0.064 mmol). The reaction mixture was stirred at RT overnight, concentrated by rotary evaporation, dissolved in 1:1 acetic acid:water (1.5 mL) and purified by reverse phase HPLC to provide the di-TFA salt of the title compound (5 mg, 35% yield). (m/z): [M+H]$^+$ calcd for $C_{45}H_{54}ClF_3N_8O_6Si$, 923.36 found 923.8.

Example 6

[(S)-1-((R)-5-{4-[5'-Chloro-4'-({6-[(R)-4-(2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-3,3-dimethyl-[1,3]azasilolidine-1-carbonyl)-2-methyl-propyl]-carbamic acid methyl ester

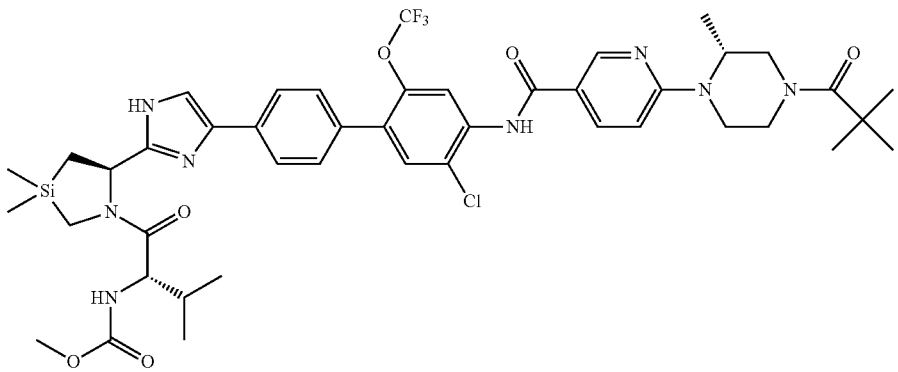 [SMILES: COC(=O)N[C@H](C(=O)N1C[Si](C)(C)C[C@H]1c1nc(-c2ccc(-c3cc(Cl)c(NC(=O)c4ccc(N5CCN(C(=O)C(C)(C)C)C[C@H]5C)nc4)cc3OC(F)(F)F)cc2)c[nH]1)C(C)C]

The intermediate of Example 5 step (b) was reacted with 2,2-dimethylpropanyl chloride under standard conditions to provide the di-TFA salt of the title compound. (0.013 mmol scale, 5 mg, 33% yield) (m/z): [M+H]calcd for $C_{44}H_{54}ClF_3N_8O_6Si$, 911.36 found 911.8.

Example 7

[(S)-1-((R)-5-{4-[4'-({6-[(R)-4-(2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-3,3-dimethyl-[1,3]azasilolidine-1-carbonyl)-2-methyl-propyl]-carbamic acid methyl ester

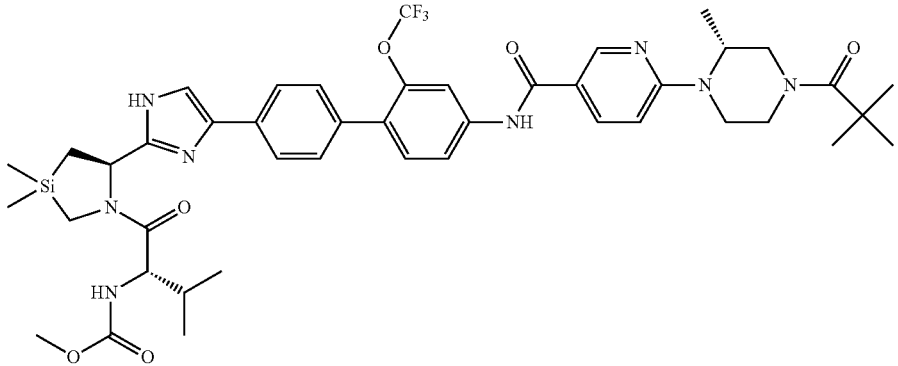 [SMILES: COC(=O)N[C@H](C(=O)N1C[Si](C)(C)C[C@H]1c1nc(-c2ccc(-c3ccc(NC(=O)c4ccc(N5CCN(C(=O)C(C)(C)C)C[C@H]5C)nc4)cc3OC(F)(F)F)cc2)c[nH]1)C(C)C]

By a procedure analogous to that of Examples 5 and 6, ((S)-1-{(R)-5-[4-(4'-{[6-((R)-2-methyl-piperazin-1-yl)-pyridine-3-carbonyl]-amino}-2'-trifluoromethoxy-biphenyl-4-yl]-1H-imidazol-2-yl]-3,3-dimethyl-[1,3]azasilolidine-1-carbonyl}-2-methyl-propyl)-carbamic acid methyl ester 3 HCl was reacted with 2,2-dimethylpropanyl chloride to provide the di-TFA salt of the title compound. (0.013 mmol scale, 6.5 mg, 46% yield) (m/z): [M+H]calcd for $C_{44}H_{55}F_3N_8O_6Si$, 877.40 found 877.8.

Example 8

[(S)-1-((2S,4S)-2-{7-[5-Chloro-4-({6-[(R)-4-(2,2-dimethyl-propionyl)-2-methyl-piperazin-1-yl]-pyridine-3-carbonyl}-amino)-2-trifluoromethoxy-phenyl]-3H-naphtho[1,2-d]imidazol-2-yl}-4-methyl-pyrrolidine-1-carbonyl)-2-methyl-propyl]-carbamic acid methyl ester produce the title intermediate (101 mg; 59% yield) as a yellow solid. (m/z): [M+H]$^+$ calcd for $C_{46}H_{52}ClF_3N_8O_6$ 921.36 found 921.3.

(b) ((S)-1-{(2S,4S)-2-[7-(5-Chloro-4-{[6-((R)-2-methyl-piperazin-1-yl)-pyridine-3-carbonyl]-amino}-2-trifluoromethoxy-phenyl)-3H-naphtho[1,2-d]imidazol-2-yl]-4-methyl-pyrrolidine-1-carbonyl}-2-methyl-propyl)-carbamic acid methyl ester The product of the previous step was treated with 4 M HCl in 1,4-dioxane (0.93 mL) and HCl (0.28 mL) and the reaction mixture was stirred at RT for 1 h, concentrated, and evaporated with ethyl acetate (2×) to produce the tri-HCl salt of the

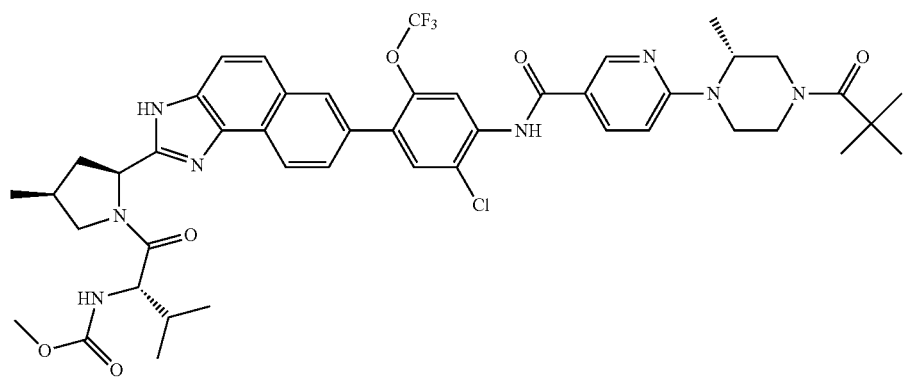 [SMILES: COC(=O)N[C@H](C(=O)N1C[C@@H](C)C[C@H]1c1nc2c(ccc3cc(-c4cc(Cl)c(NC(=O)c5ccc(N6CCN(C(=O)C(C)(C)C)C[C@H]6C)nc5)cc4OC(F)(F)F)ccc32)[nH]1)C(C)C]

(a) (R)-4-[5-(2-Chloro-4-{2-[(2S,4S)-1-((S)-2-methoxycarbonyl]amino-3-methyl-butyryl)-4-methyl-pyrrolidin-2-yl]-3H-naphtho[1,2-d]imidazol-7-yl}-5-trifluoromethoxy-phenylcarbamoyl)-pyridin-2-yl]-3-methyl-piperazine-1-carboxylic acid tert-butyl ester To a solution of (R)-4-[5-(4-bromo-2-chloro-5-trifluoromethoxy-phenylcarbamoyl)-pyridin-2-yl]-3-methyl-piperazine-1-carboxylic acid tert-butyl ester (110 mg, 0.19 mmol) and ((S)-2-methyl-1-{(2S,4S)-4-methyl-2-[7-(4,4,5,5-tetramethyl-[1,3,2]dioxaborolan-2-yl)-1H-naphtho[1,2-d]imidazol-2-yl]-pyrrolidine-1-carbonyl}-propyl)-carbamic acid methyl ester (100 mg, 0.19 mmol) dissolved in toluene (1.19 mL) and water (0.43 mL) was added potassium carbonate (128 mg, 0.93 mmol). The reaction mixture was sparged with nitrogen for 15 min and Pd(dppf)Cl$_2$ CH$_2$Cl$_2$ (13.6 mg, 0.017 mmol) was added. The reaction mixture was sparged with nitrogen, heated at 90° C. overnight, cooled to RT, diluted with EtOAc and washed with water and brine to produce a dark colored oil, which was purified by silica gel chromatography (24 g silica, 40% to 100% EtOAc/hexane) to title intermediate. (m/z): [M+H]$^+$ calcd for $C_{41}H_{44}ClF_3N_8O_5$ 821.31 found 821.3.

(c) [(S)-1-((2S,4S)-2-{7-[5-Chloro-4-({6-[(R)-4-(2,2-dimethyl-propionyl)-2-methyl-piperazin-1-yl]-pyridine-3-carbonyl}-amino)-2-trifluoromethoxy-phenyl]-3H-naphtho[1,2-d]imidazol-2-yl}-4-methyl-pyrrolidine-1-carbonyl)-2-methyl-propyl]-carbamic acid methyl ester The product of the previous step (12.0 mg, 0.013 mmol) was dissolved in DMA (1 mL) and then DIPEA (11.2 µL, 0.065 mmol) was added followed by 2,2-dimethylpropanoyl chloride (1.6 mg, 0.013 mmol) and left to stir at room temperature overnight. The reaction mixture was concentrated by rotary evaporation, dissolved in 1:1 acetic acid:water (1.5 mL) and purified by reverse phase HPLC to provide the di-TFA salt of the title compound (9.5 mg, 65% yield). (m/z): [M+H]$^+$ calcd for $C_{46}H_{52}ClF_3N_8O_6$ 905.37 found 905.8.

Example 9

((S)-1-{(2S,4S)-2-[7-(5-Chloro-4-{[6-((R)-4-cyclo-propanecarbonyl-2-methyl-piperazin-1-yl)-pyridine-3-carbonyl]-amino}-2-trifluoromethoxy-phenyl)-3H-naphtho[1,2-d]imidazol-2-yl]-4-methyl-pyrrolidine-1-carbonyl}-2-methyl-propyl)-carbamic acid methyl ester

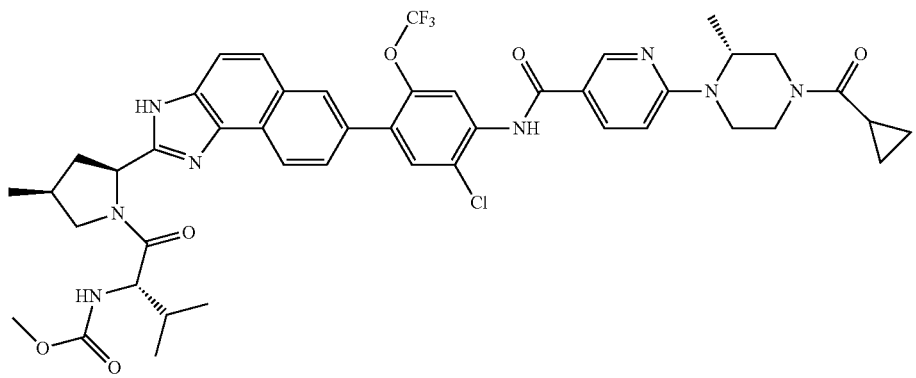 [SMILES: COC(=O)N[C@H](C(=O)N1C[C@@H](C)C[C@H]1c1nc2c(ccc3cc(-c4cc(Cl)c(NC(=O)c5ccc(N6CCN(C(=O)C7CC7)C[C@H]6C)nc5)cc4OC(F)(F)F)ccc32)[nH]1)C(C)C]

The intermediate of Example 7 step (b) was reacted with 0.5 M cyclopropanecarbonyl chloride in DMA to provide the di-TFA salt of the title compound. (0.013 mmol scale, 9.6 mg, 67% yield) (m/z): [M+H]$^+$ calcd for $C_{45}H_{48}ClF_3N_8O_6$ 889.33 found 889.8.

Example 10

[(S)-1-((2S,4S)-2-{7-[5-Chloro-4-({6-[(R)-4-((S)-2,2-dimethylcyclopropanecarbonyl)-2-methyl-piperazin-1-yl]-pyridine-3-carbonyl}-amino)-2-trifluoromethoxy-phenyl]-3H-naphtho[1,2-d]imidazol-2-yl}-4-methyl-pyrrolidine-1-carbonyl)-2-methyl-propyl]-carbamic acid methyl ester

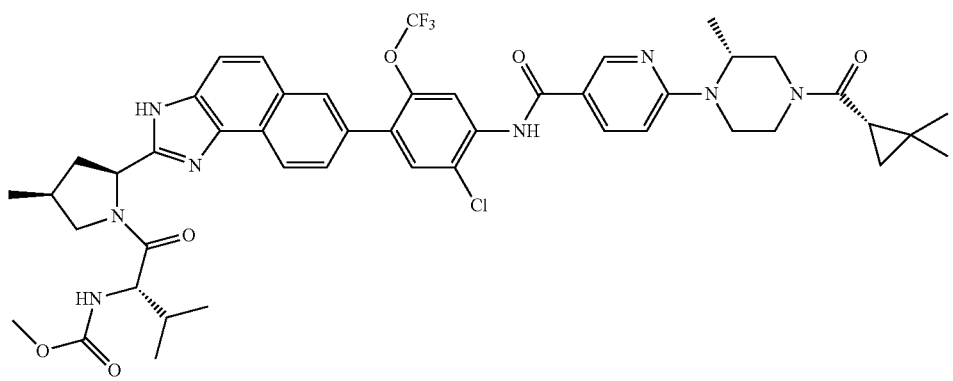

The intermediate of Example 7 step (b) was reacted with 0.5 M (S)-(+)-2,2-dimethylcyclopropane carboxylic acid in DMA to provide the di-TFA salt of the title compound. (0.013 mmol scale, 9.1 mg, 62% yield) (m/z): [M+H]$^+$ calcd for $C_{47}H_{52}ClF_3N_8O_6$ 917.37 found 917.8.

Example 11

[(S)-1-((2S,5S)-2-{4-[5'-Chloro-4'-({6-[(R)-4-(3-hydroxy-2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-5-methyl-piperidine-1-carbonyl)-2-methyl-propyl]-carbamic acid methyl ester

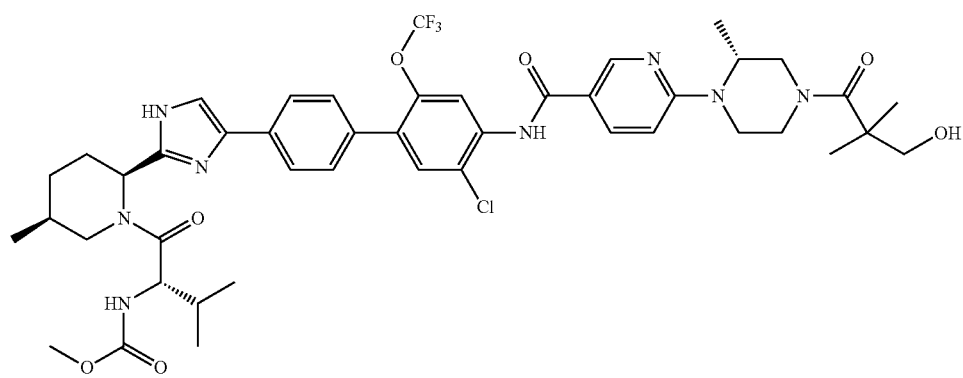 [SMILES: COC(=O)N[C@H](C(=O)N1C[C@@H](C)CC[C@H]1c1nc(-c2ccc(-c3cc(Cl)c(NC(=O)c4ccc(N5CCN(C(=O)C(C)(C)CO)C[C@H]5C)nc4)cc3OC(F)(F)F)cc2)c[nH]1)C(C)C]

(a) (R)-4-[4-(5-Chloro-4'-{2-[(2S,5S)-1-((S)-2-methoxycarbonylamino-3-methyl-butyryl)-5-methyl-piperidin-2-yl]-3H-imidazol-4-yl}-2-trifluoromethoxy-biphenyl-4-ylcarbamoyl)-pyridin-2-yl]-3-methyl-piperazine-1-carboxylic acid tert-butyl ester To a solution of [(S)-2-methyl-1-((2S,5S)-5-methyl-2-{4-[4-(4,4,5,5-tetramethyl-[1,3,2]dioxaborolan-2-yl)-phenyl]-1H-imidazol-2-yl}-piperidine-1-carbonyl)-propyl]-carbamic acid methyl ester (100 mg, 0.19 mmol) and (R)-4-[5-(4-bromo-2-chloro-5-trifluoromethoxy-phenylcarbamoyl)-pyridin-2-yl]-3-methyl-piperazine-1-carboxylic acid tert-butyl ester (113 mg, 0.19 mmol) dissolved in toluene (1.22 mL) and water (0.45 mL) was added potassium carbonate (132 mg, 0.95 mmol). The reaction mixture was sparged under nitrogen for 15 min. Pd(dppf)Cl$_2$ CH$_2$Cl$_2$ (14 mg, 0.017 mmol) was added and the reaction mixture was sparged with nitrogen, heated at 90° C. overnight, cooled to RT, diluted with EtOAc, filtered through a combined pad of Celite® and silica gel, flushed several times with EtOAc, and washed with water and brine to produce a dark colored oil. The residue was purified by silica gel chromatography (12 g silica, 40% to 100% EtOAc/hexane) to produce the title intermediate (48 mg, 28% yield) as a yellowish solid. m/z: [M+H]$^+$ calcd for C$_{45}$H$_{54}$ClF$_3$N$_8$O$_7$ 911.38 found 911.3.

(b) ((S)-1-{(2S,5S)-2-[4-(5'-Chloro-4'-{[6-((R)-2-methyl-piperazin-1-yl)-pyridine-3-carbonyl]-amino}-2'-trifluoromethoxy-biphenyl-4-yl)-1H-imidazol-2-yl]-5-methyl-piperidine-1-carbonyl}-2-methyl-propyl)-carbamic acid methyl ester The product of the previous step (48 mg) was treated with 4 M HCl in 1,4-dioxane (0.95 mL) and HCl (0.29 mL) and the reaction mixture was stirred at RT for 1 h, concentrated, and evaporated with ethyl acetate (2×) to produce the tri-HCl salt of the title intermediate. m/z: [M+H]$^+$ calcd for C$_{40}$H$_{46}$ClF$_3$N$_8$O$_5$ 811.32 found 811.3. (c) [(S)-1-((2S,5S)-2-{4-[5'-Chloro-4'-({6-[(R)-4-(3-hydroxy-2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-5-methyl-piperidine-1-carbonyl)-2-methyl-propyl]-carbamic acid methyl ester To a solution of 2,2-dimethyl-3-hydroxypropionic acid (1.5 mg, 0.013 mmol) in DMA (1 mL) was added HATU (5.0 mg, 0.013 mmol). The reaction mixture was stirred at RT for 20 min and then the product of the previous step (10 mg, 0.011 mmol) was added followed by DIPEA (11.7 µL, 0.067 mmol). The reaction mixture was stirred at RT overnight, concentrated by rotary evaporation, dissolved in 1:1 acetic acid:water (1.5 mL) and purified by reverse phase HPLC to provide the di-TFA salt of the title compound (5.3 mg, 53% yield). (m/z): [M+H]$^+$ calcd for C$_{45}$H$_{54}$ClF$_3$N$_8$O$_7$ 911.38 found 911.8.

Example 12

((S)-1-{(S)-4-Cyclopropyl-2-[4-(4'-{6-[(R)-4-(2,2-dimethyl-propionyl)-2-methyl-piperazin-1-yl]-pyridin-3-ylcarbamoyl}-2'-trifluoromethoxy-biphenyl-4-yl)-1H-imidazol-2-yl]-2,5-dihydro-pyrrole-1-carbonyl}-2-methyl-propyl)-carbamic acid methyl ester

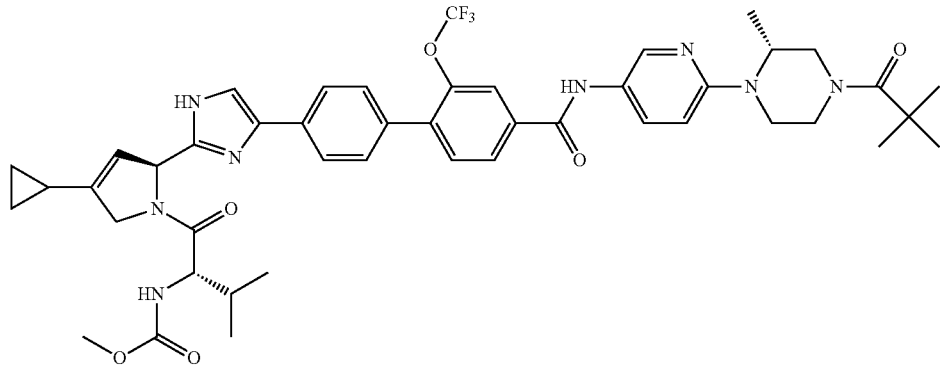 [SMILES: COC(=O)N[C@H](C(=O)N1CC(C2CC2)=C[C@H]1c1nc(-c2ccc(-c3ccc(C(=O)Nc4ccc(N5CCN(C(=O)C(C)(C)C)C[C@H]5C)nc4)cc3OC(F)(F)F)cc2)c[nH]1)C(C)C]

(a) {(S)-1-[(S)-4-Cyclopropyl-2-(4-{4'-[6-((R)-2-methyl-piperazin-1-yl)-pyridin-3-ylcarbamoyl]-2'-trifluoromethoxy-biphenyl-4-yl}-1H-imidazol-2-yl)-2,5-dihydro-pyrrole-1-carbonyl]-2-methyl-propyl}-carbamic acid methyl ester To the mixture of 4'-{2-[(S)-4-cyclopropyl-1-((S)-2-methoxycarbonylamino-3-methyl-butyryl)-2,5-dihydro-1H-pyrrol-2-yl]-1H-imidazol-4-yl}-2-trifluoromethoxy-biphenyl-4-carboxylic acid TFA (70 mg, 0.096 mmol; Preparation 15) and HATU (40 mg, 0.11 mmol) in DMF (1 mL) at RT was added (R)-4-(5-amino-pyridin-2-yl)-3-methyl-piperazine-1-carboxylic acid tert-butyl ester (31 mg, 0.11 mmol) and DIPEA (83.9 µL, 0.48 mmol). The reaction mixture was stirred at RT for 1 h, and partitioned between EtOAc (5 mL) and water (2 mL). The organic layer was dried over sodium sulfate, filtered, and concentrated to give a brownish red oil, which was treated with a mixture of DCM (1.7 mL) and TFA (1.7 mL) at RT for 1 hour. The reaction mixture was concentrated, diluted with water (6 mL), filtered and purified by reverse phase HPLC. Desired fractions were combined and freeze dried to give the tri-TFA salt of the title intermediate (68 mg, 62% yield) as a white solid. (m/z): [M+H]$^+$ calcd for $C_{41}H_{45}F_3N_8O_5$ 787.35 found 787.

(b) ((S)-1-{(S)-4-Cyclopropyl-2-[4-(4'-{6-[(R)-4-(2,2-dimethyl-propionyl)-2-methyl-piperazin-1-yl]-pyridin-3-ylcarbamoyl}-2'-trifluoromethoxy-biphenyl-4-yl)-1H-imidazol-2-yl]-2,5-dihydro-pyrrole-1-carbonyl}-2-methyl-propyl)-carbamic acid methyl ester To a solution of the product of the previous step (11 mg, 0.010 mmol) and DIPEA (8.49 µL, 0.049 mmol) in DMF (0.5 mL) was added 2,2-dimethylpropanoyl chloride (1.20 µL, 0.010 mmol) and the reaction mixture was stirred at RT overnight, concentrated by rotary evaporation, dissolved in 1:1 acetic acid:water (1.5 mL) and purified by reverse phase HPLC to provide the di-TFA salt of the title compound (9.4 mg). (m/z): [M+H]$^+$ calcd for $C_{46}H_{53}F_3N_8O_6$ 871.40 found 871.8.

Example 13

((S)-1-{(2S,4S)-2-[7-(4-{6-[(R)-4-(2,2-Dimethyl-propionyl)-2-methyl-piperazin-1-yl]-pyridin-3-ylcarbamoyl}-2-trifluoromethoxy-phenyl)-3H-naphth[1,2-d]imidazol-2-yl]-4-methyl-pyrrolidine-1-carbonyl}-2-methyl-propyl)-carbamic acid methyl ester

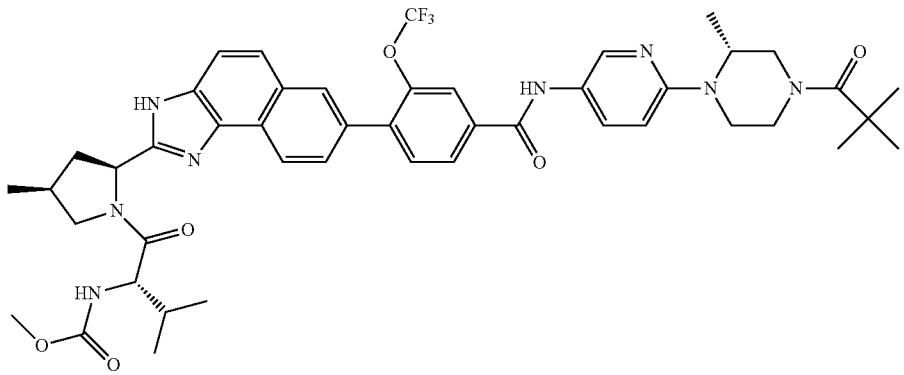 [SMILES: COC(=O)N[C@H](C(=O)N1C[C@@H](C)C[C@H]1c1nc2c(ccc3cc(-c4ccc(C(=O)Nc5ccc(N6CCN(C(=O)C(C)(C)C)C[C@H]6C)nc5)cc4OC(F)(F)F)ccc32)[nH]1)C(C)C]

73

(a) (R)-4-[5-(4-{2-[(2S,4S)-1-((S)-2-Methoxycarbonylamino-3-methyl-butyryl)-4-methyl-pyrrolidin-2-yl]-3H-naphth[1,2-d]imidazol-7-yl}-3-trifluoromethoxy-benzoylamino)-pyridin-2-yl]-3-methyl-piperazine-1-carboxylic acid tert-butyl ester A solution of 4-{2-[(2S,4S)-1-((S)-2-methoxycarbonylamino-3-methyl-butyryl)-4-methyl-pyrrolidin-2-yl]-3H-naphth[1,2-d]imidazol-7-yl}-3-trifluoromethoxy-benzoic acid TFA (136 mg, 0.19 mmol; Preparation 17) and HATU (86 mg, 0.23 mmol) in DMA (3 mL) was stirred for 10 min, then (R)-4-(5-amino-pyridin-2-yl)-3-methyl-piperazine-1-carboxylic acid tert-butyl ester (55 mg, 0.19 mmol), and DIPEA (98 µL, 0.56 mmol) were added. The resulting mixture was stirred at RT for 1 h, concentrated, and purified by silica gel chromatography (EtOAc/hexane 20 to 100%) to give the title intermediate (158 mg, 95% yield). (m/z): [M+H]$^+$ calcd for $C_{46}H_{53}F_3N_8O_7$ 887.40 found 887.4.

(b) {(S)-2-Methyl-1-[(2S,4S)-4-methyl-2-(7-{4-[6-((R)-2-methyl-piperazin-1-yl)-pyridin-3-ylcarbamoyl]-2-trifluoromethoxy-phenyl}-3H-naphth[1,2-d]imidazol-2-yl])-pyrrolidine-1-carbonyl]-propyl}-carbamic acid methyl ester The product of the previous step was treated with 4.0 M of HCl in 1,4-dioxane (2 mL) for 1 h and concentrated by rotary evaporation to provide the tri-HCl salt of the title intermediate (157 mg, 94% yield). (m/z): [M+H]$^+$ calcd for $C_{41}H_{45}F_3N_8O_5$ 787.35 found 787.3.

(c) ((S)-1-{(2S,4S)-2-[7-(4-{6-[(R)-4-(2,2-Dimethyl-propionyl)-2-methyl-piperazin-1-yl]-pyridin-3-ylcarbamoyl}-2-trifluoromethoxy-phenyl)-3H-naphth[1,2-d]imidazol-2-yl]-4-methyl-pyrrolidine-1-carbonyl}-2-methyl-propyl)-carbamic acid methyl ester To a solution of the product of the previous step (15 mg, 0.017 mmol) and DIPEA (14.6 µL, 0.084 mmol) in DMA (0.5 mL) was added 2,2-dimethylpropionyl chloride (2.06 µL, 0.017 mmol. The resulting mixture was stirred at RT overnight, concentrated by rotary evaporation, dissolved in 1:1 acetic acid:water (1.5 mL) and purified by reverse phase HPLC to provide the di-TFA salt of the title compound (7.8 mg). (m/z): [M+H]$^+$ calcd for $C_{46}H_{53}F_3N_8O_6$ 871.40 found 871.8.

Example 14

[(S)-2-((2S,4S)-2-{7-[4-({6-[(R)-4-(2,2-Dimethyl-propionyl)-2-methyl-piperazin-1-yl]-pyridine-3-carbonyl}-amino)-5-chloro-2-trifluoromethoxy-phenyl]-3H-naphtho[1,2-d]imidazol-2-yl}-4-methyl-pyrrolidin-1-yl)-2-oxo-1-(tetrahydropyran-4-yl)-ethyl]-carbamic acid methyl ester

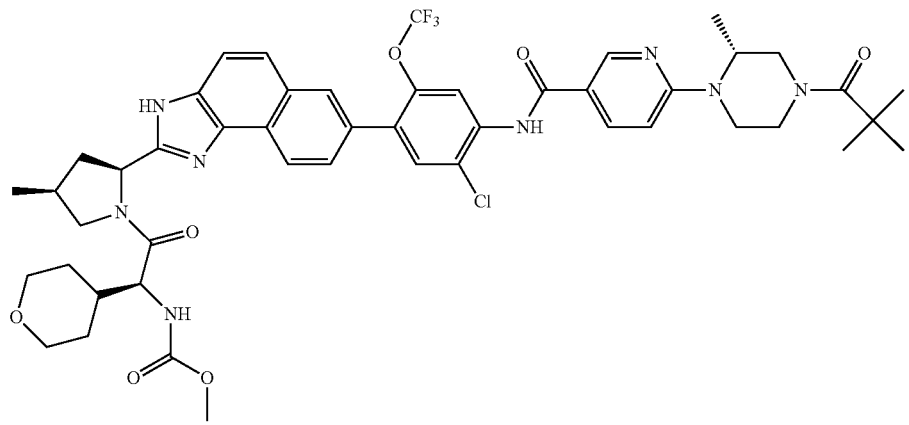 [SMILES: COC(=O)N[C@H](C(=O)N1C[C@@H](C)C[C@H]1c1nc2c(ccc3cc(-c4cc(Cl)c(NC(=O)c5ccc(N6CCN(C(=O)C(C)(C)C)C[C@H]6C)nc5)cc4OC(F)(F)F)ccc32)[nH]1)C1CCOCC1]

(a) (R)-4-{5-[2-Chloro-4-(2-{(2S,4S)-1-[(S)-2-methoxycarbonylamino-2-(tetrahydro-pyran-4-yl)-acetyl]-4-methyl-pyrrolidin-2-yl}-3H-naphtho[1,2-d]imidazol-7-yl)-5-trifluoromethoxy-phenylcarbamoyl]-pyridin-2-yl}-3-methyl-piperazine-1-carboxylic acid tert-butyl ester To a mixture of [(S)-2-{(2S,4S)-4-methyl-2-[7-(4,4,5,5-tetramethyl-1,3,2-dioxaborolan-2-yl)-3H-naphth[1,2-d]imidazol-2-yl]-pyrrolidin-1-yl}-2-oxo-1-(tetrahydro-pyran-4-yl)-ethyl]-carbamic acid methyl ester (80 mg, 0.10 mmol; Preparation 23) and (R)-4-[5-(4-bromo-2-chloro-5-trifluoromethoxy-phenylcarbamoyl)-pyridin-2-yl]-3-methyl-piperazine-1-carboxylic acid tert-butyl ester (85 mg, 0.14 mmol) dissolved in toluene (0.92 mL) and water (0.34 mL) was added potassium carbonate (103 mg, 0.75 mmol). The reaction mixture was sparged under nitrogen and Pd(dppf)Cl$_2$ CH$_2$Cl$_2$ (7.0 mg, 0.009 mmol) was added and the reaction mixture was heated to 90° C. overnight, cooled to RT, filtered through a combined pad of Celite® and silica gel and washed with EtOAc. The filtrate was washed with water and brine to produce a brownish colored solid, which was purified by silica chromatography (12 g column, 5-100% EtOAc/hexanes) to produce the title intermediate (89 mg, 60% yield) as a light colored solid. (m/z): [M+H]$^+$ calcd for $C_{48}H_{54}ClF_3N_8O_8$ 963.37 found 963.5.

(b) [(S)-2-{(2S,4S)-2-[7-(5-Chloro-4-{[6-((R)-2-methyl-piperazin-1-yl)-pyridine-3-carbonyl]-amino}-2-trifluoromethoxy-phenyl)-3H-naphth[1,2-d]imidazol-2-yl]-4-methyl-pyrrolidin-1-yl}-2-oxo-1-(tetrahydro-pyran-4-yl)-ethyl]-carbamic acid methyl ester The solid from the previous step was treated with 4 M HCl in 1,4-dioxane (1 mL) and stirred at RT overnight, concentrated, and evaporated with EtOAc (2×) to produce the tri-HCl salt of the title intermediate (80 mg, 60% yield) as a yellow solid. (m/z): [M+H]+ calcd for $C_{43}H_{46}ClF_3N_8O_6$ 863.32 found 863.6.

(c) [(S)-2-((2S,4S)-2-{7-[4-({6-[(R)-4-(2,2-Dimethyl-propionyl)-2-methyl-piperazin-1-yl]-pyridine-3-carbonyl}-amino)-5-chloro-2-trifluoromethoxy-phenyl]-3H-naphtho[1,2-d]imidazol-2-yl}-4-methyl-pyrrolidin-1-yl)-2-oxo-1-(tetrahydropyran-4-yl)-ethyl]-carbamic acid methyl ester To a solution of the product of the previous step (23 mg, 0.024 mmol) and DIPEA (29 µL, 0.16 mmol) dissolved in DMF (0.5 mL) was added 2,2-dimethylpropionyl chloride (2.9 µL, 0.024 mmol). The reaction mixture was stirred at RT for 1 h, concentrated, dissolved in 1:1 acetic acid:water (1.5 mL), and purified by reverse-phase HPLC to provide the di-TFA salt of the title compound (14.1 mg). (m/z): [M+H]+ calcd for $C_{48}H_{54}ClF_3N_8O_7$ 947.38 found 947.8.

Example 15

[(S)-2-((2S,4S)-2-{7-[4-({6-[(R)-4-(3-Hydroxy-2,2-dimethyl-propionyl)-2-methyl-piperazin-1-yl]-pyridine-3-carbonyl}-amino)-5-chloro-2-trifluoromethoxy-phenyl]-3H-naphtho[1,2-d]imidazol-2-yl}-4-methyl-pyrrolidin-1-yl)-2-oxo-1-(tetrahydropyran-4-yl)-ethyl]-carbamic acid methyl ester

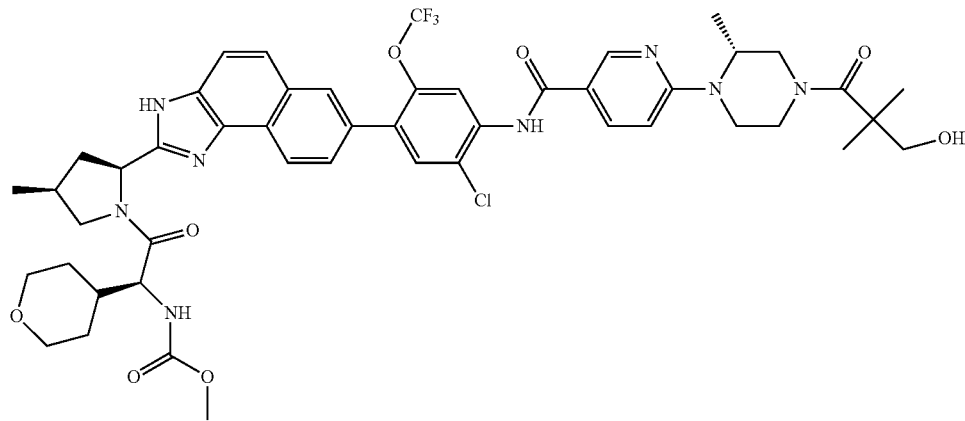 [SMILES: COC(=O)N[C@H](C(=O)N1C[C@@H](C)C[C@H]1c1nc2c(ccc3cc(-c4cc(Cl)c(NC(=O)c5ccc(N6CCN(C(=O)C(C)(C)CO)C[C@H]6C)nc5)cc4OC(F)(F)F)ccc32)[nH]1)C1CCOCC1]

The intermediate of Example 14 step (b) was reacted at the 0.024 mol scale with 2,2-dimethyl-3-hydroxypropionic acid and HATU (1.5 equiv) to provide the di-TFA salt of the title compound (13.9 mg). (m/z): [M+H]+ calcd for $C_{48}H_{54}ClF_3N_8O_8$ 963.37 found 963.8.

Using similar synthetic procedures, the compounds of Tables 1 to 5 were prepared, where a blank in any column denotes hydrogen.

TABLE 1

| Ex No. | * | $R^{11}$ | $R^{7a}$ | $R^{7d}$ | $R^9$ | Formula | Calc [M + H]+ | Found [M + H]+ |
|---|---|---|---|---|---|---|---|---|
| 1-1 | (S) | | | | ⟨gem-dimethylcyclopropyl⟩ | $C_{44}H_{54}N_8O_5$ | 775.42 | 775.4 |

TABLE 1-continued

| Ex No. | * | $R^{11}$ | $R^{7a}$ | $R^{7d}$ | $R^9$ | Formula | Calc [M + H]$^+$ | Found [M + H]$^+$ |
|---|---|---|---|---|---|---|---|---|
| 1-2 | | | | | imidazolyl group | $C_{42}H_{48}N_{10}O_5$ | 773.38 | 773.2 |
| 1-3 | | | | | —NHCH$_3$ | $C_{40}H_{49}N_9O_5$ | 736.39 | 736.2 |
| 1-4 | (S) | CH$_3$ | OCF$_3$ | Cl | (S)-dimethylcyclopropyl | $C_{46}H_{54}ClF_3N_8O_6$ | 907.38 | 907.8 |
| 1-5 | (S) | CH$_3$ | OCF$_3$ | Cl | tert-butyl | $C_{45}H_{54}ClF_3N_8O_6$ | 895.38 | 895.8 |
| 1-6 | (R) | CH$_3$ | OCF$_3$ | Cl | neopentyl-OH | $C_{45}H_{54}ClF_3N_8O_7$ | 911.38 | 911.8 |
| 1-7 | (R) | CH$_3$ | OCF$_3$ | Cl | (S)-dimethylcyclopropyl | $C_{46}H_{54}ClF_3N_8O_6$ | 907.38 | 907.8 |
| 1-8 | (R) | CH$_3$ | OCF$_3$ | Cl | tert-butyl | $C_{45}H_{54}ClF_3N_8O_6$ | 895.38 | 895.8 |

TABLE 2

| Ex No. | R⁴ | * | R⁸ᵈ | R⁹ | Formula | Calc [M + H]⁺ | Found [M + H]⁺ |
|---|---|---|---|---|---|---|---|
| 2-1 | CH₃ | (S) | CH₃ | cyclopropyl | $C_{44}H_{49}F_3N_8O_6$ | 843.37 | 843.8 |
| 2-2 | CH₃ | (S) | CH₃ | —NHCH₃ | $C_{42}H_{48}F_3N_9O_6$ | 832.37 | 832.8 |
| 2-3 | CH₃ | (S) | CH₃ | tert-butyl | $C_{45}H_{53}F_3N_8O_6$ | 859.40 | 859.8 |
| 2-4 | CH₃ | (S) | CH₃ | (S)-2,2-dimethylcyclopropyl | $C_{46}H_{53}F_3N_8O_6$ | 871.40 | 871.8 |
| 2-5 | CH₃ | (S) | CH₃ | CH₂NHC(O)CH₃ | $C_{44}H_{50}F_3N_9O_7$ | 874.38 | 874.8 |
| 2-6 | CH₃ | (S) | CH₃ | 1-hydroxy-2,2-dimethylcyclopropyl | $C_{46}H_{53}F_3N_8O_7$ | 887.40 | 887.8 |
| 2-7 | CH₃ | (S) | CH₃ | 2,2-dichlorocyclopropyl | $C_{44}H_{47}Cl_2F_3N_8O_6$ | 911.30 | 911.8 |
| 2-8 | CH₃ | (S) | CH₃ | NHC(O)-(S)-2,2-dimethylcyclopropyl | $C_{50}H_{60}F_3N_9O_7$ | 956.46 | 957.0 |

TABLE 2-continued
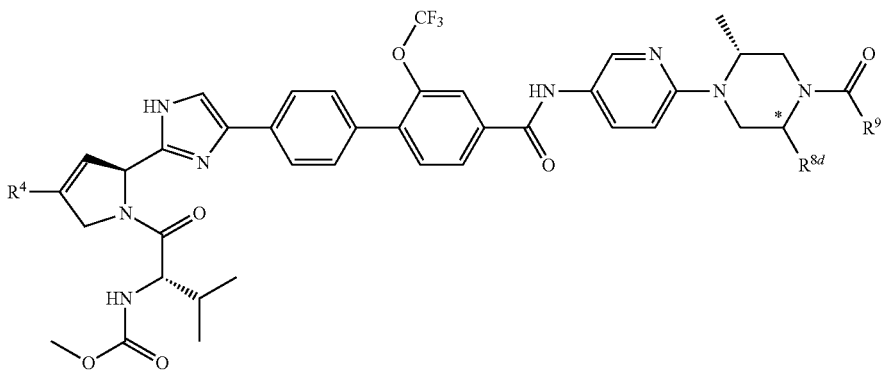
| Ex No. | R⁴ | * | R⁸ᵈ | R⁹ | Formula | Calc [M + H]⁺ | Found [M + H]⁺ |
|---|---|---|---|---|---|---|---|
| 2-9 | $CH_3$ | (S) | $CH_3$ | 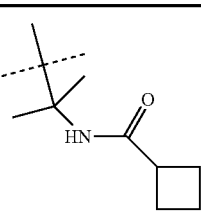 | $C_{49}H_{58}F_3N_9O_7$ | 942.44 | 943.0 |
| 2-10 | cPr | | | 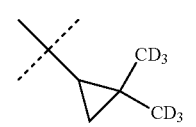 | $C_{47}H_{47}D_6F_3N_8O_6$ | 889.44 | 890.0 |
| 2-11 | cPr | | | 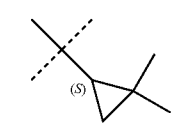 | $C_{47}H_{53}F_3N_8O_6$ | 883.40 | 883.8 |
TABLE 3
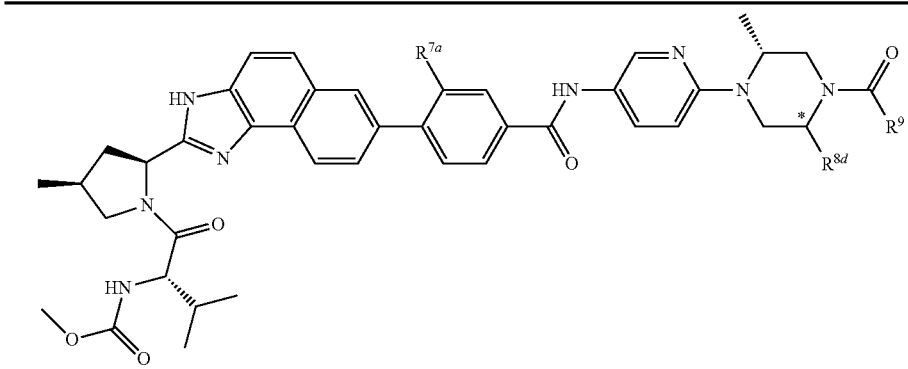
| Ex No. | R⁷ᵃ | * | R⁸ᵈ | R⁹ | Formula | Calc [M + H]⁺ | Found [M + H]⁺ |
|---|---|---|---|---|---|---|---|
| 3-1 | | | | 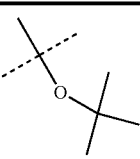 | $C_{45}H_{54}N_8O_6$ | 803.42 | 803.8 |

TABLE 3-continued

| Ex No. | R⁷ᵃ | * | R⁸ᵈ | R⁹ | Formula | Calc [M + H]⁺ | Found [M + H]⁺ |
|---|---|---|---|---|---|---|---|
| 3-2 | | | | (S)-1,1-dimethylcyclopropyl | $C_{46}H_{54}N_8O_5$ | 799.42 | 799.1 |
| 3-3 | | | | —NHCH₃ | $C_{42}H_{49}N_9O_5$ | 760.39 | 760.8 |
| 3-4 | OCF₃ | | | cyclopropyl-methyl | $C_{45}H_{49}F_3N_8O_6$ | 855.37 | 855.8 |
| 3-5 | OCF₃ | | | (S)-1,1-dimethylcyclopropyl | $C_{47}H_{53}F_3N_8O_6$ | 883.40 | 884.0 |
| 3-6 | OCF₃ | | | 1,1-bis(CD₃)cyclopropyl | $C_{47}H_{47}D_6F_3N_8O_6$ | 889.44 | 888.8 |
| 3-7 | OCF₃ | | | N(CH₃)₂ | $C_{44}H_{50}F_3N_9O_6$ | 858.38 | 858.8 |
| 3-8 | OCF₃ | (S) | CH₃ | 1,1-bis(CD₃)cyclopropyl | $C_{48}H_{49}D_6F_3N_8O_6$ | 903.46 | 904.0 |
| 3-9 | OCF₃ | (S) | CH₃ | tert-butyl | $C_{47}H_{55}F_3N_8O_6$ | 885.42 | 886.0 |
| 3-10 | OCF₃ | (S) | CH₃ | N(CH₃)₂ | $C_{45}H_{52}F_3N_9O_6$ | 872.40 | 872.8 |
| 3-11 | OCF₃ | (S) | CH₃ | cyclopropyl-methyl | $C_{46}H_{51}F_3N_8O_6$ | 869.39 | 869.8 |

TABLE 3-continued
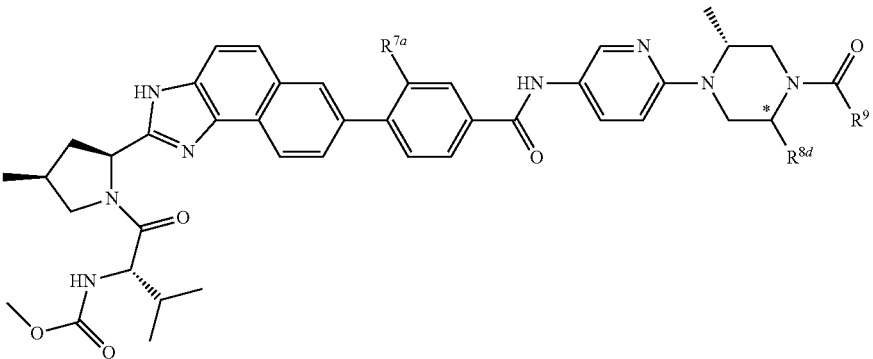
| Ex No. | $R^{7a}$ | * | $R^{8d}$ | $R^9$ | Formula | Calc $[M + H]^+$ | Found $[M + H]^+$ |
|---|---|---|---|---|---|---|---|
| 3-12 | $OCF_3$ | (S) | $CH_3$ | 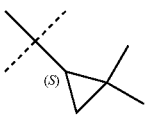 | $C_{48}H_{55}F_3N_8O_6$ | 897.42 | 898.0 |
| 3-13 | $OCF_3$ | | | 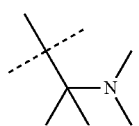 | $C_{47}H_{56}F_3N_9O_6$ | 900.43 | 900.8 |
| 3-14 | $OCF_3$ | | | 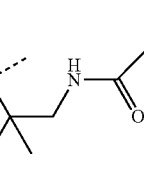 | $C_{50}H_{58}F_3N_9O_7$ | 954.44 | 955.0 |
| 3-15 | $OCF_3$ | | | 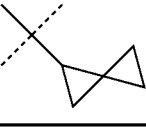 | $C_{47}H_{51}F_3N_8O_6$ | 881.39 | 881.8 |
TABLE 4
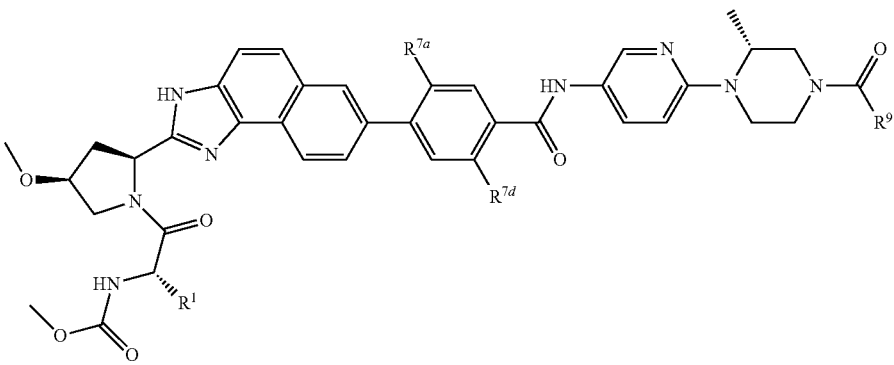
| Ex No. | $R^1$ | $R^{7a}$ | $R^{7d}$ | $R^9$ | Formula | Calc $[M + H]^+$ | Found $[M + H]^+$ |
|---|---|---|---|---|---|---|---|
| 4-1 | 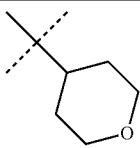 | $OCF_3$ | |  | $C_{48}H_{55}F_3N_8O_9$ | 945.40 | 945.6 |

TABLE 4-continued
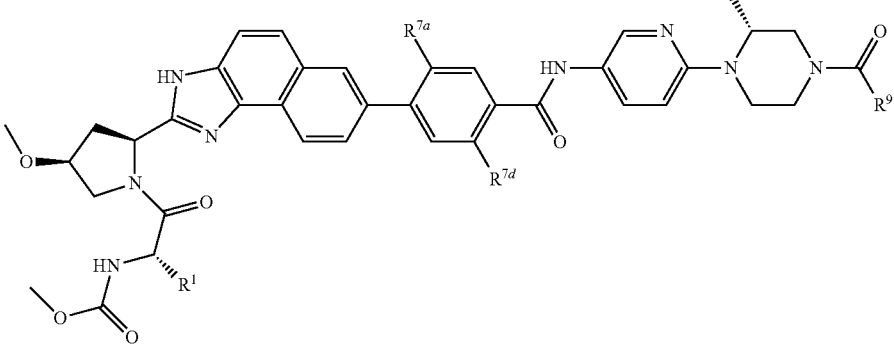
| Ex No. | R¹ | R⁷ᵃ | R⁷ᵈ | R⁹ | Formula | Calc [M + H]⁺ | Found [M + H]⁺ |
|---|---|---|---|---|---|---|---|
| 4-2 | (tetrahydropyran-4-yl) | OCF₃ | | (gem-dimethyl) | $C_{48}H_{55}F_3N_8O_8$ | 929.41 | 929.6 |
| 4-3 | (cyclohexyl) | | | (S)-(1,1-dimethylcyclopropyl) | $C_{49}H_{58}N_8O_6$ | 855.45 | 855.6 |
| 4-4 | (tetrahydropyran-4-yl) | | | (S)-(1,1-dimethylcyclopropyl) | $C_{48}H_{56}N_8O_7$ | 857.43 | 857.6 |
| 4-5 | (isopropyl/t-Bu) | | | (S)-(1,1-dimethylcyclopropyl) | $C_{46}H_{56}N_8O_5$ | 801.44 | 801.6 |
TABLE 5
| Ex No. | | Formula | Calc [M + H]⁺ | Found [M + H]⁺ |
|---|---|---|---|---|
| 5-1 | 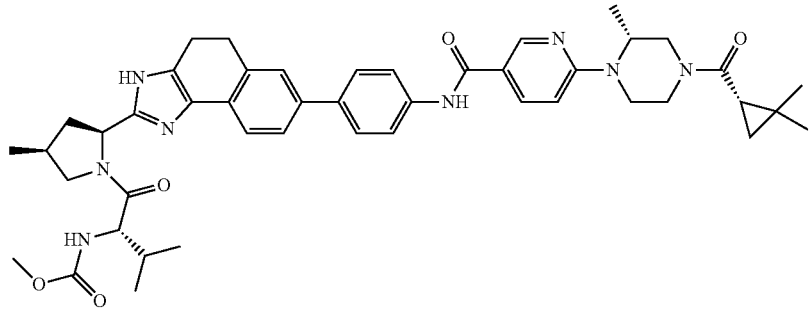 | $C_{45}H_{54}N_8O_5$ | 787.42 | 787.4 |

TABLE 5-continued

| Ex No. | Formula | Calc [M + H]+ | Found [M + H]+ |
|---|---|---|---|
| 5-2 | C₄₈H₅₄F₄N₈O₇ | 931.41 | 931.8 |
| 5-3 | C₄₈H₅₄F₄N₈O₈ | 947.40 | 947.8 |
| 5-4 | C₄₇H₅₄ClF₃N₈O₇ | 935.38 | 935.8 |
| 5-5 | C₄₅H₅₂ClF₃N₈O₆ | 893.37 | 893.8 |

TABLE 5-continued

| Ex No. | Formula | Calc [M + H]+ | Found [M + H]+ |
|---|---|---|---|
| 5-6 | C₄₈H₅₄ClF₃N₈O₇ | 947.38 | 948.0 |
| 5-7 | C₄₈H₅₄ClF₃N₈O₈ | 963.37 | 964.0 |
| 5-8 | C₄₆H₅₂ClF₃N₈O₆ | 905.37 | 905.8 |
| 5-9 | C₄₅H₅₂ClF₃N₈O₇ | 909.36 | 909.8 |

TABLE 5-continued

| Ex No. | Formula | Calc [M + H]+ | Found [M + H]+ |
|---|---|---|---|
| 5-10 | $C_{45}H_{52}ClF_3N_8O_6$ | 893.37 | 893.8 |
| 5-11 | $C_{46}H_{54}ClF_3N_8O_6$ | 907.38 | 907.6 |
| 5-12 | $C_{48}H_{56}ClF_3N_8O_7$ | 949.39 | 949.6 |

Biological Assays

The hepatitis C virus has been classified into six major different genotypes on the basis of nucleotide sequence, and further divided into subtypes within genotypes. Compounds of the invention demonstrated inhibition of HCV replication in one or more of the following HCV replicon assays.

Assay 1: HCV Genotype 1b Replicon Assay

The HCV genotype 1b replicon cell line was obtained from Apath LLC (Brooklyn, N.Y.) (APC144; Huh7 cell background). This subgenomic replicon contains the N-terminus of the HCV core protein fused to the neomycin-resistance selectable marker. The EMCV IRES lies downstream and drives expression of humanized Renilla luciferase fused to the non-structural proteins NS3-NS5B. This cell line was used to determine compound potency using the luciferase activity readout as a measurement of compound inhibition of replicon levels.

Cells were grown at 37° C. in a 5% $CO_2$ humidified incubator in DMEM (Invitrogen) with 10% FBS (HyClone), 1×NEAA (Invitrogen), 1× Pen-Strep (Invitrogen), and 500 μg/mL G418 (Invitrogen). On day 1 of the assay, cells were plated at 10,000 cells/well in white 96-well tissue culture plates (Costar) in 200 μL media lacking G418. Four hours later, once the cells have adhered, the media was removed and replaced with media (no G418) containing dose-responses of test compounds. Compounds were initially diluted in DMSO and then diluted another 200× in media to bring the final DMSO concentration down to 0.5%. The cells were incubated with test compounds for 48 hours. At the end of the incubation period, media and compound were removed from the plates and the luciferase activity was determined using Promega Renilla-Glo reagents.

To analyze the data, the luciferase activity was plotted vs. the compound concentration, and $EC_{50}$ values were determined from a 4-parameter robust fit model with the GraphPad Prism software package (GraphPad Software, Inc., San Diego, Calif.). Results are expressed as the negative decadic logarithm of the $EC_{50}$ value, $pEC_{50}$.

Test compounds having a higher $pEC_{50}$ value in this assay show greater inhibition of HCV genotype 1b replication. Compounds of the invention tested in this assay typically exhibited $pEC_{50}$ values between about 7 and about 12.

Assay 2: HCV Genotype 1a Replicon Assay

The HCV genotype 1a replicon cell line was obtained from Apath LLC (APC89; Huh7.5 cell background). This subgenomic replicon contains the N-terminus of the HCV core protein fused to the neomycin-resistance selectable marker. The EMCV IRES lies downstream and drives expression of the non-structural proteins NS3-NS5B. Compound potencies were determined using the NS3-specific protease activity in lysates as a measurement of compound inhibition of replicon levels.

Cells were grown at 37° C. in a 5% $CO_2$ humidified incubator in DMEM (Invitrogen) with 10% FBS (HyClone), 1×NEAA (Invitrogen), 1× Pen-Strep (Invitrogen), and 850 µg/mL G418 (Invitrogen). On day 1 of the assay, cells were plated at 15,000 cells/well in black 96-well tissue culture plates (Costar) in 200 µL media lacking G418. Four hours later, once the cells had adhered, the media was removed and replaced with media (no G418) containing dose-responses of test compounds. Compounds were initially diluted in DMSO and then diluted another 200× in media to bring the final DMSO concentration down to 0.5%. The cells were incubated with test compounds for 48 or 72 hours. At the end of the incubation period, media and compound were removed from the plates.

To determine the NS3-specific protease activity in lysates, the cells were lysed at room temperature in 50 µL/well of 50 mM Hepes pH 7.5, 150 mM NaCl, 15% Glycerol, 0.15% Triton X-100, 10 mM DTT for 20 minutes with shaking. 50 µL of an NS3/4a protease-specific FRET substrate (Anaspec RET S1 Cat#22991) was then added to the wells at a final concentration of 15 µM. The plates were incubated at 37° C. for 20 minutes, which corresponds to a timepoint at which the protease activity is still in the linear phase. Protease activity was determined by measuring fluorescence (Excitation: 340 nm; Emission: 509 nm).

To analyze the data, the fluorescence was plotted vs. the compound concentration, and EC50 values were determined from a 4-parameter robust fit model using GraphPad Prism software. Compounds of the invention tested in this assay typically exhibited $pEC_{50}$ values between about 6 and about 11.5.

Assay 3: Replicon Assays Against Resistant Mutants

To create replicon cells with resistant mutations of interest, the mutation was first introduced into the parental plasmid by site-directed mutagenesis. Mutations in genotype 1b included L31V, Y93H, and the L31V/Y93H double mutant. Mutations in genotype 1a included Q30R and L31V. The replicon plasmid was then linearized and in vitro transcribed to RNA. The RNA was used to stably transfect Huh7 cells by electroporation, and new cell lines were selected with 500 µg/mL G418. Potencies of test compounds against these mutant cell lines were determined as previously described above for the HCV Genotype 1b and 1a replicon assays.

Potencies of test compounds against additional mutations of interest were determined using transient transfection assays. These mutants included genotype 1a Y93C, Y93H, M28T, Q30E, Q30K, L31M, and Y93N. The mutation was first introduced into the parental plasmid by site-directed mutagenesis. The replicon plasmid was then linearized and in vitro transcribed to RNA. The RNA was used to transiently transfect Huh-LUNET cells (obtained from ReBLikon GmbH, Schriesheim, Germany) by electroporation, and the potencies of test compounds against the mutants were determined as previously described.

Assay 4: Replicon Assays Against NS5A Sequences of Other Genotypes

Potencies of test compounds against NS5A sequences of other genotypes were determined by creating intergenotypic chimeras. The entire NS5A gene from genotypes 2a, 2b, 3a, 4a, 5a, and 6a, or the nucleotide sequence encoding amino acids 11-118 of NS5A, was subcloned into a genotype 1b replicon. For genotype 2a, intergenotypic chimeras with both the JFH and the J6 strain were created. In general, NS5A inhibitors have been shown to exhibit significantly weaker potency against the J6 strain due to the presence of a naturally occurring L31M sequence variant. Since the majority of genotype 2a sequences in public databases contain the L31M sequence variant, the use of the J6 genotype 2a sequence may better reflect the antiviral potency of NS5A inhibitors.

These chimeric replicon plasmids were then linearized and in vitro transcribed to RNA. The RNA was used to transiently or stably transfect Huh-LUNET cells by electroporation, and the potencies of test compounds against the chimeras were determined as previously described.

Assay Results

All of the compounds of Examples 1 to 15 and Tables 1 to 5 were tested in one or more of the assays described above. For example, the following results were obtained in the HCV genotype 1a and 1b replicon assays where A represents a $pEC_{50}$ value between 6 and 8 ($EC_{50}$ between 1 µM and 10 nM), B represents $pEC_{50}$ between 8 and 9 ($EC_{50}$ between 1 and 10 nM), C represents $pEC_{50}$ between and 9 and about 10, ($EC_{50}$ between 1 nM and 0.1 nM), and D represents $pEC_{50}$>10 ($EC_{50}$<0.1 nM).

| Example No. | Genotype 1a | Genotype 1b |
| --- | --- | --- |
| 1 | D | |
| 2 | D | |
| 3 | D | |
| 4 | D | D |
| 5 | D | D |
| 6 | C | |
| 7 | C | D |
| 8 | D | D |
| 9 | D | D |
| 10 | D | D |
| 11 | C | |
| 12 | C | |
| 13 | D | D |
| 14 | D | D |
| 15 | D | D |

TABLE 3

| Example No. | Genotype 1a | Genotype 1b |
| --- | --- | --- |
| 3-1 | D | D |
| 3-2 | D | |
| 3-3 | D | |
| 3-4 | D | |
| 3-5 | D | D |
| 3-6 | D | |
| 3-7 | D | |
| 3-8 | D | |
| 3-9 | D | |
| 3-10 | D | |
| 3-11 | D | |
| 3-12 | D | |
| 3-13 | D | |

TABLE 3-continued

| Example No. | Genotype 1a | Genotype 1b |
|---|---|---|
| 3-14 | C | |
| 3-15 | D | |

TABLE 1

| | | |
|---|---|---|
| 1-1 | C | D |
| 1-2 | B | |
| 1-3 | B | |
| 1-4 | C | |
| 1-5 | C | |
| 1-6 | C | |
| 1-7 | D | |
| 1-8 | C | |

TABLE 4

| | | |
|---|---|---|
| 4-1 | D | D |
| 4-2 | D | |
| 4-3 | D | |
| 4-4 | D | |
| 4-5 | A | |

TABLE 2

| | | |
|---|---|---|
| 2-1 | C | |
| 2-2 | C | |
| 2-3 | C | |
| 2-4 | D | |
| 2-5 | C | |
| 2-6 | C | |
| 2-7 | C | |
| 2-8 | B | |
| 2-9 | C | |
| 2-10 | D | D |
| 2-11 | D | D |

TABLE 5

| | | |
|---|---|---|
| 5-1 | D | D |
| 5-2 | D | D |
| 5-3 | D | D |
| 5-4 | D | |
| 5-5 | C | |
| 5-6 | D | D |
| 5-7 | D | D |
| 5-8 | D | |
| 5-9 | D | |
| 5-10 | D | D |
| 5-11 | C | |
| 5-12 | C | |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A compound of formula (I):

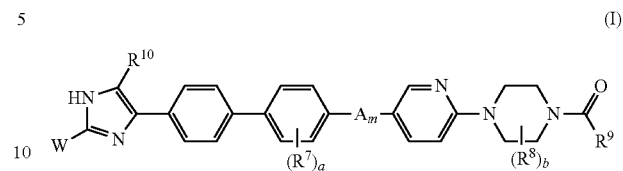

(I)

wherein

W is selected from

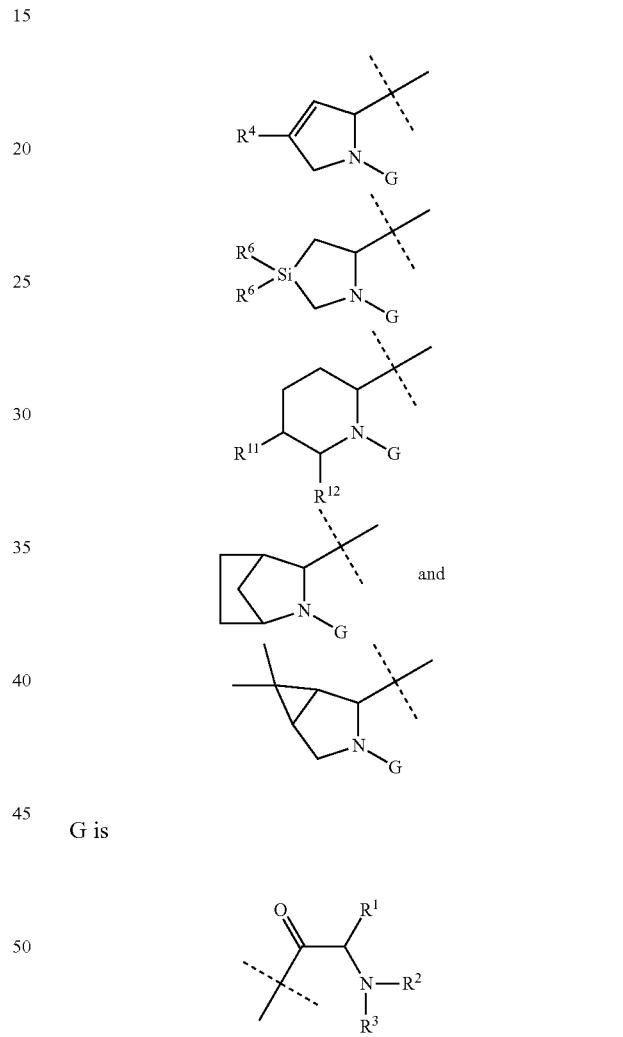

G is

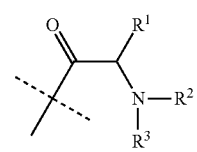

$R^1$ is selected from $C_{1-6}$alkyl, $C_{1-6}$alkoxy, phenyl, $C_{3-6}$cycloalkyl, heterocycle, and heteroaryl, wherein $C_{1-6}$alkyl is optionally substituted with —$OR^a$, amino, —$SR^e$, heterocycle, or heteroaryl, $C_{1-6}$alkoxy is optionally substituted with —$OR^a$, and heterocycle is optionally substituted with —$OR^a$, amino, or —C(O)O$C_{1-6}$alkyl, or with one or two $C_{1-3}$alkyl;

$R^2$ is selected from hydrogen and $C_{1-6}$alkyl;

$R^3$ is selected from hydrogen, $C_{-6}$alkyl, —C(O)O$C_{1-6}$alkyl, —C(O)N$R^b R^c$, —C(O)$C_{3-6}$cycloalkyl, and —S(O)$_2 C_{1-3}$alkyl;

$R^4$ is selected from $C_{1-6}$alkyl, $C_{3-6}$cycloalkyl, and halo;

$R^6$ is independently selected from hydrogen, $C_{1-6}$alkyl, and halo;

$R^7$ is selected from halo, $C_{1-3}$alkyl, and $C_{1-3}$alkoxy wherein $C_{1-3}$alkyl and $C_{1-3}$alkoxy are optionally substituted with one, two, three, four, or five halo;

$R^8$ is $C_{1-3}$alkyl, optionally substituted with —$OR^d$;

$R^9$ is selected from $C_{1-6}$alkyl, $C_{3-6}$cycloalkyl, $C_{1-6}$alkoxy, —$NR^fR^g$, heteroaryl, heterocycle, and —$CH_2$-heteroaryl;

wherein:
$C_{1-6}$alkyl is optionally substituted with one or two substituents independently selected from —$OR^h$, —$NR^jR^k$, —$NHC(O)C_{1-3}$alkyl, —$NHC(O)C_{3-6}$cycloalkyl, and —$NHC(O)OC_{1-3}$alkyl;

$C_{1-6}$alkoxy is optionally substituted with —$OR^h$;

any $C_{3-6}$cycloalkyl is optionally substituted with one, two, or three substituents independently selected from $C_{1-3}$alkyl, halo, —$OR^h$, and —$CD_3$;

any heterocycle is optionally substituted with one, two, or three substituents independently selected from $C_{1-3}$alkyl, halo, —$C(O)OC_{1-3}$alkyl, —$C(O)C_{1-6}$alkyl, —$C(O)C_{3-6}$cycloalkyl, —$C(O)NHC_{1-6}$alkyl, and —$C(O)NHC_{3-6}$cycloalkyl;

wherein any —$C(O)C_{1-6}$alkyl is optionally substituted with —$NHC(O)OC_{1-3}$alkyl, —$OR^h$ or —$NR^jR^k$, any heteroaryl is optionally substituted with one or two $C_{1-3}$alkyl;

$R^a, R^b, R^c, R^d, R^e, R^f, R^h, R^j$, and $R^k$ are each independently hydrogen or $C_{1-3}$alkyl;

$R^g$ is selected from hydrogen, $C_{1-6}$alkyl, and $C_{3-6}$cycloalkyl;

$R^{10}$ is hydrogen, halo, or $C_{1-3}$alkyl substituted with one, two, or three halo or with —$OR^d$;

$R^{11}$ is selected from hydrogen, $C_{1-6}$alkyl, and halo;

$R^{12}$ is hydrogen, or $R^{11}$ and $R^{12}$ taken together form —$CH_2$—;

$A_m$ is —NHC(O)— or —C(O)NH— a is 0, 1, or 2; and b is 0, 1 or 2;

or a pharmaceutically-acceptable salt or stereoisomer thereof.

2. The compound of claim 1 wherein the compound of formula (I) is a compound of formula (Ia):

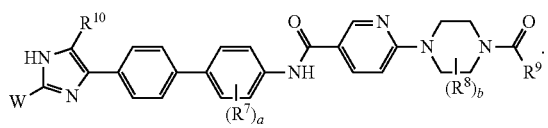

(Ia)

3. The compound of claim 2 wherein $R^1$ is selected from $C_{1-6}$alkyl, phenyl, and tetrahydropyranyl, wherein $C_{1-6}$alkyl is optionally substituted with —$OR^a$;

$R^2$ is hydrogen or $C_{1-6}$alkyl; and $R^3$ is selected from hydrogen, $C_{1-6}$alkyl, and —C(O)OC$_{1-6}$alkyl.

4. The compound of claim 2 wherein $R^7$ is selected from fluoro, chloro, —$CF_3$, and —$OCF_3$.

5. The compound of claim 2 wherein $R^9$ is selected from $C_{1-6}$alkyl, optionally substituted with —$OR^h$, and $C_{3-4}$cycloalkyl, optionally substituted with one or two $C_{1-3}$alkyl.

6. The compound of claim 1 wherein the compound of formula (I) is a compound of formula (Ib):

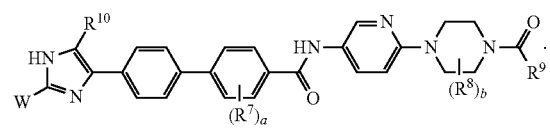

(Ib)

7. A pharmaceutical composition comprising a compound of claim 1 and a pharmaceutically-acceptable carrier.

8. The pharmaceutical composition of claim 7 further comprising one or more other therapeutic agents useful for treating hepatitis C viral infections.

9. The pharmaceutical composition of claim 8 wherein the one or more other therapeutic agents is selected from HCV NS3 protease inhibitors, and HCV NS5B nucleoside and non-nucleoside polymerase inhibitors.

10. A method of treating hepatitis C viral infection in a mammal, the method comprising administering to the mammal a pharmaceutical composition comprising a compound of claim 1 and a pharmaceutically-acceptable carrier.

11. The method of claim 10 wherein the method further comprises administering one or more other therapeutic agents useful for treating hepatitis C viral infections.

12. The method of claim 11 wherein the one or more other therapeutic agents is selected from HCV NS3 protease inhibitors, HCV NS5B nucleoside and non-nucleoside polymerase inhibitors, interferons and pegylated interferons, cyclophilin inhibitors, HCV NS5A inhibitors, and ribavirin.

13. A method of inhibiting replication of the hepatitis C virus in a mammal, the method comprising administering to the mammal a pharmaceutical composition comprising a compound of claim 1 and a pharmaceutically-acceptable carrier.

14. The method of claim 13 wherein the method further comprises administering to the mammal one or more other therapeutic agents useful for inhibiting replication of the hepatitis C virus in a mammal.

15. The method of claim 14 wherein the one or more other therapeutic agents is selected from HCV NS3 protease inhibitors, HCV NS5B nucleoside and non-nucleoside polymerase inhibitors, interferons and pegylated interferons, cyclophilin inhibitors, HCV NS5A inhibitors, and ribavirin.

* * * * *